US011155483B1

(12) United States Patent
Tong et al.

(10) Patent No.: US 11,155,483 B1
(45) Date of Patent: Oct. 26, 2021

(54) METHOD FOR EFFICIENTLY PRODUCING PHA

(71) Applicants: Nutrition & Health Research Institute, COFCO Corporation, Beijing (CN); COFCO (jilin) Bio-Chemical Technology CO., Ltd, Changchun (CN); COFCO BIOTECHNOLOGY CO., LTD., Bengbu (CN); Tsinghua University, Beijing (CN)

(72) Inventors: Yi Tong, Beijing (CN); Yi Li, Beijing (CN); Fang Tian, Beijing (CN); Weiqiang Zhou, Beijing (CN); Yuanheng Guo, Beijing (CN); Guoqiang Chen, Beijing (CN); Dayong Li, Changchun (CN); Haijun Liu, Changchun (CN); Kejia Xu, Beijing (CN); Anni Liu, Beijing (CN); Bo Chen, Beijing (CN); Tai An, Beijing (CN); Xiaoyan Wang, Beijing (CN); Chao Peng, Beijing (CN); Xuemei Shen, Beijing (CN); Jin Tao, Changchun (CN); Lida Wu, Changchun (CN); Kai Yang, Beijing (CN); Qiong Wu, Beijing (CN)

(73) Assignees: Nutrition & Health Research Institute, COFCO Corporation, Beijing (CN); COFCO (jilin) Bio-Chemical Technology CO., Ltd, Changchun (CN); COFCO Biotechnology Co., Ltd., Bengbu (CN); Tsinghua University, Beijing (CN)

( * ) Notice: Subject to any disclaimer, the term of this patent is extended or adjusted under 35 U.S.C. 154(b) by 0 days.

(21) Appl. No.: 17/135,984

(22) Filed: Dec. 28, 2020

(30) Foreign Application Priority Data

Jun. 30, 2020 (CN) .......................... 202010607208.5

(51) Int. Cl.
C02F 3/12 (2006.01)
C02F 3/34 (2006.01)
(Continued)

(52) U.S. Cl.
CPC ............ *C02F 3/1221* (2013.01); *B01D 37/02* (2013.01); *B01D 39/08* (2013.01); *B01D 61/00* (2013.01); *C02F 1/28* (2013.01); *C02F 1/72* (2013.01); *C02F 3/1263* (2013.01); *C02F 3/34* (2013.01); *C08G 63/90* (2013.01); *C12M 29/00* (2013.01); *C12M 33/14* (2013.01); *C12N 1/02* (2013.01); *C12N 1/06* (2013.01); *C12N 1/066* (2013.01); *C12P 7/62* (2013.01);
(Continued)

(58) Field of Classification Search
CPC .... C12N 9/2437; C12N 9/0065; C12N 15/80; C12N 9/2434; C12N 9/2445; C12N 9/2477; C12N 15/1137; C12N 2310/14; C12N 2310/141; C12N 15/01; C12N 1/14; C12N 9/0061; C07K 1/00; C07K 2319/00; C07K 2319/036; C12P 19/02; C12P 19/14; C12P 21/02; C12P 7/24; C12P 13/008; C12P 7/04; C12P 7/18; C12P 7/26; C12P 7/22; C12P 7/42; C12P 7/64; C12P 11/00; C12P 13/02; C12P 21/00; C12P 7/40; C12P 7/62; C12P 7/66; C12P 17/00; C12P 7/00; C12Y 302/01004; C12Y 111/02001; C12Y 111/02004; C11D 3/38636; C11D 3/38654; Y02P 20/52; C08G 63/06; C08G 63/88; C12R 1/885; C01B 25/45; C02F 101/30; C02F 11/18
See application file for complete search history.

(56) References Cited

U.S. PATENT DOCUMENTS

| 7,582,456 B2* | 9/2009 | Chen ...................... C08G 63/88 435/135 |
| 2007/0072276 A1* | 3/2007 | Chen ...................... C08G 63/88 435/135 |

FOREIGN PATENT DOCUMENTS

| CN | 1328160 A | 12/2001 |
| CN | 1464063 A | 12/2003 |

(Continued)

OTHER PUBLICATIONS

Yokaryo et al., PHB production from molasses by alkaliphilic *Halomonas* sp, 2012.
(Continued)

*Primary Examiner* — Deborah K Ware
(74) *Attorney, Agent, or Firm* — Volpe Koenig

(57) ABSTRACT

A method for efficiently producing PHA comprising: inoculating PHA fermentation strains into a fermentation medium for fermentation under the condition of being capable of producing PHA through fermentation; subjecting the fermentation broth to a solid-liquid separation to obtain fermentation supernatant and thallus precipitate; breaking the cell walls of the thallus precipitate, and subjecting the wall-broken products to a plate and frame filtration to prepare PHA; pre-coating a filter cloth for the plate and frame filtration with a PHA layer; at least part of the water of the fermentation medium is PHA process wastewater. The method utilizes the PHA process wastewater as at least part of the water of the fermentation medium, and filters and separates the broken thallus with the plate and frame filtration equipment pre-coated with PHA layer to prepare PHA, thereby recycling the high-salt wastewater, reducing costs, and potentially separating PHA on a large scale for industrial production.

10 Claims, No Drawings

(51) Int. Cl.
- *C12M 1/00* (2006.01)
- *C12N 1/02* (2006.01)
- *C12N 1/06* (2006.01)
- *C12P 7/62* (2006.01)
- *C12M 1/26* (2006.01)
- *C08G 63/90* (2006.01)
- *B01D 37/02* (2006.01)
- *B01D 39/08* (2006.01)
- *B01D 61/00* (2006.01)
- *C02F 1/28* (2006.01)
- *C02F 1/72* (2006.01)

(52) U.S. Cl.
CPC ............... *B01D 2239/0471* (2013.01); *C02F 2209/001* (2013.01); *C02F 2209/105* (2013.01); *C12N 2500/05* (2013.01); *C12N 2500/12* (2013.01); *C12N 2500/16* (2013.01); *C12N 2500/34* (2013.01)

(56) References Cited

FOREIGN PATENT DOCUMENTS

| | | |
|---|---|---|
| CN | 1211489 C | 7/2005 |
| CN | 1844185 A | 10/2006 |
| CN | 100448911 C | 1/2009 |
| CN | 101892271 A | 11/2010 |
| CN | 101096651 B | 12/2010 |
| CN | 102120973 A | 7/2011 |
| CN | 102492737 A | 6/2012 |
| CN | 102952774 B | 9/2015 |
| CN | 106687502 A | 5/2017 |
| CN | 108821467 A | 11/2018 |
| CN | 109504714 A | 3/2019 |
| CN | 109504715 A | 3/2019 |
| CN | 109517156 A | 3/2019 |
| CN | 110004182 A | 7/2019 |
| CN | 111019108 A | 4/2020 |
| CN | 111333822 A | 6/2020 |
| JP | 2005192401 A | 7/2005 |
| KR | 970001829 B1 | 2/1997 |

OTHER PUBLICATIONS

Gouda et al., Production of PHB by a Bacillus megaterium strain using surgance molasses and corn steep liquor as sole carbon and nitrogen sources, Microbiological Research, pp. 201-207, 2001.

Xirong, Theoretical analysis on recycling of fermentation waste liquid, Chemical Engineering (China), vol. 16, No. 5, Oct. 1988.

"Methods and Techniques for water conservation and emission reduction in industrial processes—Vitamin C production as an example" and its machine translation.

Koller, Recycling of Waste Streams of the Biotechnological Poly(hydroxyalkanoate) Production by Haloferax mediterranei on Whey, Hindawi Publishing Co., International Journal of Polymer Sciences, pp. 1-8, 2015.

Ying, Fermentation Engineering, China Agricultural University Press, 1991.

* cited by examiner

METHOD FOR EFFICIENTLY PRODUCING PHA

PRIORITY CLAIM & CROSS REFERENCE

The application claims priority to Chinese Application No. 202010607208.5, filed on Jun. 30, 2020, entitled "Method for Efficiently Producing PHA", which is herein specifically and entirely incorporated by reference.

FIELD OF INVENTION

The present disclosure relates to the technical field of producing bio-based material Polyhydroxyalkanoate (PHA), in particular to a method for efficiently producing PHA.

BACKGROUND

Polyhydroxyalkanoate (PHA) is a generic name for a kind of high molecular polyesters which are entirely synthesized by microorganisms. PHA has biodegradability and biocompatibility, thus the PHA is considered as an environment-friendly material, which is conducive for solving the problem of increasingly serious environmental pollution, and has a rosy application prospect. Although the basic and applicative researches have been comprehensively performed recently on the PHA, the PHA has not been put into large-scale industrial production in the People's Republic of China (PRC) at present, thus there is an urgent need to carry out research on processes and methods of the PHA industrial production.

Halophilic bacteria is the high-yield strain with excellent properties which has been selected and cultured in recent years, but its fermentation process requires a high-concentration salt environment; the use of a large amount of inorganic salt may on one hand, causes high production costs, and on the other hand, the treatment of the generated high-salt wastewater needs high costs.

Moreover, the patents with respect to the industrial production of PHA are mainly focused on the engineered strains, such as CN110004182A, CN102952774B, CN102120973B and CN101096651B. Some patents are associated with the PHA separation methods, for instance, CN100448911C, CN109517156A, CN1211489C, CN109504715A, etc., most of the patents adopt a multiple centrifugal separation method, but the centrifugal separation method has the disadvantages such as low separation efficiency for a standalone machine, large energy consumption, high operative difficulty, and limited separation capability; it requires a plurality of centrifuges to operate simultaneously for large-scale industrialization, which results in the large amount of one-off investment on facilities and devices.

SUMMARY

The present disclosure aims to overcome the problems in the prior art and provide a method for efficiently producing PHA, the method uses PHA process wastewater as at least part of water of a fermentation medium, and separates the broken thallus with the plate and frame filtration equipment pre-coated with a PHA layer to prepare PHA, thereby perform recycling of the high-salt wastewater, reduce the costs and lower the one-off investment, and the method may be used for separating PHA in a large scale and implementing the industrial production.

In order to fulfill the above purposes, the present disclosure provides a method for producing polyhydroxyalkanoate (PHA) through fermentation, the method comprises the following steps:

(1) inoculating PHA fermentation strains into a fermentation medium for fermentation under the condition of being capable of producing PHA through fermentation to obtain a fermentation broth;

(2) subjecting the fermentation broth to a first solid-liquid separation to obtain a fermentation supernatant and a thallus precipitate;

(3) breaking cell walls of the thallus precipitate, and subjecting obtained wall-broken products to a plate and frame filtration to obtain PHA;

wherein a filter cloth for the plate and frame filtration is pre-coated with a PHA layer;

wherein at least part of the water of the fermentation medium is PHA process wastewater, and the PHA process wastewater comprises the fermentation supernatant.

In regard to the technical problem that the PHA has not been put into large-scale industrial production in China at present, the present disclosure provides a high-efficiency industrialized PHA production method, wherein the PHA fermentation broth is obtained through fermentation of PHA fermentation strains, high-purity PHA products are obtained through a series of unit operations which includes subjecting the fermentation broth to a solid-liquid separation, breaking the cell walls of the thallus precipitate, performing separation and purification of the wall-broken products with the plate and frame filtration equipment pre-coated with a PHA layer; the high-salt PHA process wastewater after separating out the target cells and target products is subject to simple treatment and subsequently recycled to the next batch of fermentation and production, the method can save resources and reduce discharge of the wastewater. The method in the present disclosure has simple and convenient operations and high resource utilization efficiency, and can be used for industrial production.

The method can realize the repeated recycling of the PHA process wastewater for the PHA fermentation process under the condition of ensuring the PHA fermentation effect, given that the wastewater contains a large amount of salts and other unused nutrient components, the recycling of the PHA process wastewater can decrease the addition amount of salts in the culture medium ingredients, and effectively reduce the production costs of PHA.

The method adopts a plate and frame separation of PHA to replace the traditional centrifugal separation of PHA, and the PHA layer is pre-coated on the filter cloth for the plate and frame filtration, thereby overcome the defects in the prior art such as high cost and operational difficulty caused by adopting multiple centrifugal separations; in addition, the method of the present disclosure also exhibits the advantages of high recovery rate of PHA and high purity of the prepared PHA product.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure provides a method for producing polyhydroxyalkanoate (PHA) through fermentation, the method comprises the following steps:

(1) inoculating PHA fermentation strains into a fermentation medium for fermentation under the condition of being capable of producing PHA through fermentation to obtain a fermentation broth;

(2) subjecting the fermentation broth to a first solid-liquid separation to obtain a fermentation supernatant and a thallus precipitate;

(3) breaking cell walls of the thallus precipitate, and subjecting obtained wall-broken products to a plate and frame filtration to obtain PHA;

wherein a filter cloth for the plate and frame filtration is pre-coated with a PHA layer;

wherein at least part of the water of the fermentation medium is PHA process wastewater, and the PHA process wastewater includes the fermentation supernatant.

Step (1)

According to the present disclosure, although the object of the present disclosure can be achieved as long as the PHA fermentation process wastewater is recycled to the fermentation process and reused as a water of a culture medium, it is preferable that the PHA process wastewater has a viscosity lower than 20 CPS, a chemical oxygen demand (COD) value lower than 10,000 mg/L, and a chroma lower than 80, so as to further improve the fermentation efficiency.

Wherein the viscosity can be measured by using a viscometer.

Wherein the chroma may be determined by using a platinum cobalt standard method.

According to the present disclosure, when the indicators of the wastewater generated by the PHA fermentation process exceed the above thresholds, the wastewater can be further treated, for example, the wastewater may be concentrated for use in biofertilizers, or be purified to meet the requirements of the aforementioned indicators and then used as at least part of the water of the fermentation medium. It shall be noted even if the indicators of the wastewater generated in the PHA fermentation process are within the above ranges, the wastewater may subject to a purification treatment to improve the fermentation efficiency. The methods for the purification treatment will be described below in detail.

According to the present disclosure, it is further preferred that the PHA process wastewater is clear in color, free of significant suspension and precipitation, and has a solid content within a range of 2-5 wt %.

According to the present disclosure, the PHA process wastewater which is supplemented with pure water or not, is preferably used as the water of the fermentation medium.

According to a preferred embodiment of the present disclosure, the fermentation medium uses a PHA process wastewater supplemented with pure water as the water, the volume ratio of PHA process wastewater to pure water is 3-10:1, for example 3:1, 4:1, 5:1, 6:1, 7:1, 8:1, 9:1, 10:1.

According to the present disclosure, the fermentation medium preferably contains a carbon source, a nitrogen source, a phosphate, a magnesium salt and a sodium salt.

According to the present disclosure, it is preferable that the carbon source is at least one selected from the group consisting of glucose, a starch saccharification liquid and high-salt molasses.

According to the present disclosure, the amount of the carbon source can be selected within a wide range, preferably 10-100 g of carbon source per 1 L fermentation medium.

According to a specific embodiment of the present disclosure, the carbon source is glucose, preferably, the content of glucose is 10-35 g, 10 g, 15 g, 20 g, 25 g, 30 g, 35 g, and more preferably 15-30 g, relative to 1 L fermentation medium.

According to another preferred embodiment of the present disclosure, the carbon source is high-salt molasses. Wherein the high-salt molasses refers to molasses with salt content of 8-11 wt % and sugar content of 40-70 wt % based on dry weight of the high-salt molasses.

In the present disclosure, the "salt" in the "high-salt molasses" refers to sodium chloride.

According to the present disclosure, the high-salt molasses may be any molasses meeting the above requirements in terms of salt content and sugar content, for example, high-salt cane molasses and/or high-salt beet molasses.

According to a preferred embodiment of the present disclosure, the high-salt molasses is high salt cane molasses having a salt content above 9 wt %, such as 9-11 wt %, and a sugar content above 50 wt %, such as 50-70 wt %, based on dry weight; the sugar includes glucose, sucrose and fructose, wherein the glucose is 5-15 wt %, the sucrose is 75-85 wt % and the fructose is 5-12 wt %, based on total amount of sugar.

According to the present disclosure, the high-salt molasses can be crude high-salt molasses, or refined high-salt molasses, or a syrup obtained by decolorizing and diluting the refined high-salt molasses.

According to a preferred embodiment of the present disclosure, in order to further improve the fermentation efficiency, the high-salt molasses before its use as a carbon source is subjected to acid hydrolysis, for example, the acid hydrolysis is performed by using dilute hydrochloric acid having a concentration not more than 20 wt %, and the conditions of the acid hydrolysis may comprise: the temperature is within a range of 15–45° C., the time is 0.5-1.5 h, and the dosage of dilute hydrochloric acid is 2-10 ml relative to 100 g of high-salt molasses.

Preferably, the content of high-salt molasses is 10-60 mL, for example, 10 mL, 15 mL, 20 mL, 25 mL, 30 mL, 35 mL, 40 mL, 45 mL, 50 mL, 55 mL, 60 mL, more preferably 15-35 mL, relative to 1 L fermentation medium.

According to a specific embodiment of the present disclosure, the carbon source is a saccharified starch solution, and the saccharified starch solution is contained in an amount of 10-60 mL, for example, 10 mL, 15 mL, 20 mL, 25 mL, 30 mL, 35 mL, 40 mL, 45 mL, 50 mL, 55 mL, or 60 mL, more preferably 15 to 35 mL, relative to 1 L fermentation medium.

According to the present disclosure, the species of the nitrogen source is not particularly limited as long as it can provide a necessary nitrogen source for the PHA fermentation broth, it may be an organic nitrogen source, for example, a natural complex nitrogen source such as corn steep liquor, corn steep liquor powder, soybean meal and yeast powder, or an inorganic nitrogen source, for instance, urea, ammonium sulfate and the like.

According to the present disclosure, the content of the nitrogen source can be selected within a wide range, preferably within a range of 5-50 g relative to 1 L fermentation medium.

According to a preferred embodiment of the present disclosure, the nitrogen source is corn steep liquor.

Corn steep liquor is one of byproducts in the corn in-depth processing industry, and the corn steep liquor is obtained by concentrating the corn soaking water. The corn steep liquor is an extremely nutritious substance, when the corn steep liquor is concentrated to a solid content of 40-50 wt %, the protein content will exceed 40 wt %. In addition, the corn steep liquor further contains various amino acids, vitamins, inorganic salts, phosphorus, potassium and other nutrient components.

The corn steep liquor has extensive use, the corn steep liquor and the corn bran are mixed and processed into the corn flakes to be used as feedstuff raw material, but the corn steep liquor is used in a small amount, most of the residual corn steep liquor is directly discharged to a sewage treatment plant for treatment; the cheap corn steep liquor is subjected to a series of operations consisting of a bag type filtration, evaporation concentration for several times, a secondary filtration and a low-temperature centrifugal spray drying to prepare corn steep liquor dry powder for sale, but the operation process for preparing dry powder is complicated, the energy resource consumption is huge, and the commercially added value is low.

The source of corn steep liquor is not particularly limited, for example, it is derived from the COFCO Biotechnology Co., Ltd. of the China Oil and Foodstuffs Corporation (COFCO), as a technologically advanced corn deep processing enterprise with largest scale in China, the COFCO Biotechnology has 7 million tons of corn processing capacity. The corn steep liquor used in the present disclosure can be obtained from COFCO Biochemical Energy (Yushu) Co., Ltd., which processes and transforms 600,000 tons of corn per year, produces a large amount of the waste corn steep liquor, and the waste corn steep liquor discharge and treatment requires a large amount of investment. The PHA is produced by using cheap byproducts produced in the traditional corn deep processing industry as a matrix and utilizing the fermentation strains *Halomonas* sp., it not only solves the problem associated with high cost of fermentation raw materials in the industrial production process of PHA, but also addresses the problem of resources and energy consumed by enterprises in treating waste corn steep liquor.

Wherein the corn steep liquor may have a solid content within a range of 10-50 wt % (e.g., 10 wt %, 15 wt %, 20 wt %, 25 wt %, 30 wt %, 35 wt %, 40 wt %, 45 wt %, 50 wt %, or any value therebetween), more preferably within a range of 40-50 wt %.

According to the present disclosure, the corn steep liquor may be any corn steep liquor that meets the above requirements in terms of solid content.

According to the present disclosure, the corn steep liquor may be the corn steep liquor after removing impurities or the corn steep liquor without removing impurities, and preferably, the corn steep liquor is the corn steep liquor after removing impurities.

According to the present disclosure, it is preferable that the method for removing impurities is filtration.

More preferably, the filtration includes, but is not limited to, at least one of the group consisting of gauze filtration, plate and frame filtration, vacuum filtration and membrane filtration treatment.

According to the present disclosure, preferably, the corn steep liquor is enzymolyzed corn steep liquor. According to the present disclosure, the corn steep liquor is subjected to enzymolysis, the insoluble substances such as cellulose, protein and starch in the corn steep liquor are hydrolyzed into micromolecular saccharides and amino acids which are used as nutrient substances to be utilized by microorganisms, such that the utilization rate of raw materials is increased, and the PHA yield is improved.

According to the present disclosure, there is no particular limitation on the enzyme used for enzymolysis of the corn steep liquor, and preferably, the enzyme is selected from the group consisting of cellulase, hemicellulase, amylase and acid protease, and more preferably, the enzyme is cellulase, hemicellulase, amylase and acid protease.

According to the present disclosure, the used amount of the enzyme may be selected from a wide range, and preferably, the cellulase is used in an amount of 0.01-0.15 parts by weight (e.g., may be 0.01 parts by weight, 0.03 parts by weight, 0.05 parts by weight, 0.07 parts by weight, 0.09 parts by weight, 0.11 parts by weight, 0.13 parts by weight, 0.15 parts by weight, or any value therebetween), and more preferably 0.08-0.1 parts by weight, relative to 1,000 parts by weight of the corn steep liquor; the hemicellulase is used in an amount of 0.01-0.15 parts by weight (e.g., 0.01 parts by weight, 0.03 parts by weight, 0.05 parts by weight, 0.07 parts by weight, 0.09 parts by weight, 0.11 parts by weight, 0.13 parts by weight, 0.15 parts by weight, or any value therebetween), more preferably 0.08-0.1 parts by weight, relative to 1,000 parts by weight of the corn steep liquor; the amylase is used in an amount of 0.01-0.06 parts by weight (e.g., may be 0.01 parts by weight, 0.02 parts by weight, 0.03 parts by weight, 0.04 parts by weight, 0.05 parts by weight, 0.06 parts by weight, or any value therebetween), more preferably 0.02-0.05 parts by weight, relative to 1,000 parts by weight of the corn steep liquor; the acidic protease is used in an amount of 0.08-0.2 parts by weight (e.g., 0.08 parts by weight, 0.1 parts by weight, 0.12 parts by weight, 0.14 parts by weight, 0.16 parts by weight, 0.18 parts by weight, 0.2 parts by weight, or any value therebetween), and more preferably 0.12-0.18 parts by weight, relative to 1,000 parts by weight of the corn steep liquor.

According to the present disclosure, the conditions of the enzymolysis can be selected within a wide range, and preferably, the conditions of the enzymolysis comprise: the temperature is within a range of 40-55° C. (such as 40° C., 43° C., 46° C., 49° C., 52° C., 55° C., or any value therebetween), and more preferably 45-50° C.; the time is within a range of 20-50 min (such as 20 min, 25 min, 30 min, 35 min, 40 min, 45 min, 50 min, or any value therebetween), more preferably 30-40 min; the pH of the enzymolysis is within a range of 4-6 (e.g., 4, 4.5, 5, 5.5, 6, or any value therebetween), more preferably 5-5.5.

According to the present disclosure, it is preferable that the enzymolysis is performed under a stirring condition, and the rotation speed of stirring is within a range of 200-1,000 rpm (such as 200 rpm, 300 rpm, 400 rpm, 500 rpm, 600 rpm, 700 rpm, 800 rpm, 900 rpm, 1,000 rpm, or any value therebetween), and more preferably 500-800 rpm.

According to the present disclosure, the enzymolyzed corn steep liquor is preferably the enzymolyzed corn steep liquor after subjecting to a solid-liquid separation, and the solid-liquid separation can be implemented with a variety of conventional solid-liquid separation methods, for example, the methods include but are not limited to, centrifugation, membrane separation, plate and frame filtration and the like, and preferably membrane filtration, and the pore diameter of the membrane is within a range of 100-600 nm.

More preferably, the membrane is a ceramic membrane.

According to the present disclosure, the content of the corn steep liquor in the fermentation medium may be selected from a wide range, and preferably, the content of the corn steep liquor is within a range of 5-45 mL, for example, 5 mL, 10 mL, 15 mL, 20 mL, 25 mL, 30 mL, 35 mL, 40 mL, 45 mL, more preferably 10-40 mL, and further preferably 32-36 mL, relative to 1 L of the fermentation medium.

According to a specific embodiment of the present disclosure, the nitrogen source is urea and corn starch, the content of corn steep liquor powder is within a range of 15-21 g, for example 15 g, 16 g, 17 g, 18 g, 19 g, 20 g, 21 g, relative to 1 L of fermentation medium; the urea content may be within a range of 1.5-2.5 g, for example, 1.5 g, 1.7 g, 1.9 g, 2.1 g, 2.3 g, 2.5 g, relative to 1 L of fermentation medium.

According to a specific embodiment of the present disclosure, the nitrogen source is yeast powder, preferably, the content of the yeast powder is within a range of 13-18 g, for example, 13 g, 14 g, 15 g, 16 g, 17 g, 18 g, preferably 15-17 g, relative to 1 L of the fermentation medium.

The phosphate content can be selected from a wide range, and preferably, the phosphate content is within a range of 5-20 g, for example, 5 g, 7 g, 9 g, 1 g, 13 g, 15 g, 16 g, 17 g, 18 g, 19 g, 20 g, relative to 1 L of the fermentation medium.

According to the present disclosure, the phosphate may be a phosphate conventionally used in PHA fermentation processes, for example, sodium salts of phosphoric acid, potassium salts of phosphoric acid, preferably, the phosphate is dipotassium hydrogen phosphate and disodium hydrogen phosphate; more preferably, the content of dipotassium hydrogen phosphate is 2-5 g, preferably 2.5-4 g, for example, 2.5 g, 2.6 g, 2.7 g, 2.8 g, 2.9 g, 3 g, 3.1 g, 3.2 g, 3.3 g, 3.4 g, 3.5 g, or 4 g, relative to 1 L of the fermentation medium; the content of disodium hydrogen phosphate is 5-8 g, preferably 5.5-7.5 g, and for example, may be 5.5 g, 6 g, 6.5 g, 7 g or 7.5 g.

According to the present disclosure, the magnesium salt may be a variety of conventional magnesium salts excluding the magnesium salt of phosphoric acid, preferably, the magnesium salt is magnesium sulfate and/or magnesium chloride.

The content of the magnesium salt may be selected from a wide range, and is preferably 0.1-0.5 g, for example, 0.1 g, 0.15 g, 0.2 g, 0.25 g, 0.3 g, 0.35 g, 0.4 g, 0.45 g, 0.5 g, and more preferably 0.2-0.3 g, relative to 1 L of the fermentation medium.

According to the present disclosure, the sodium salt may be any conventional sodium salt excluding the sodium salt of phosphoric acid, preferably, the sodium salt is sodium chloride.

The content of sodium salt can be selected from a wide range, and preferably, the content of sodium salt is within a range of 40-70 g, for example, 40 g, 45 g, 50 g, 55 g, 60 g, 65 g, 70 g, and more preferably 45-55 g, relative to 1 L of the fermentation medium.

According to a preferred embodiment of the present disclosure, the fermentation medium is 1 #fermentation medium comprising high-salt molasses, yeast powder, dipotassium hydrogen phosphate, disodium hydrogen phosphate, magnesium sulfate and sodium chloride; relative to 1 L of fermentation medium, the high-salt molasses content is 15-35 ml, the yeast powder content is 15-17 g, the dipotassium hydrogen phosphate content is 2-5 g, the disodium hydrogen phosphate content is 5-8 g, the magnesium sulfate content is 0.2-0.3 g, and the sodium chloride content is 45-55 g.

According to a preferred embodiment of the present disclosure, the fermentation medium is 2 #fermentation medium comprising corn steep liquor, glucose, dipotassium hydrogen phosphate, disodium hydrogen phosphate, magnesium sulfate and sodium chloride; relative to 1 L of the fermentation medium; the corn steep liquor content is 32-36 ml, the glucose content is 15-30 g, the dipotassium hydrogen phosphate content is 2-5 g, the disodium hydrogen phosphate content is 5-8 g, the magnesium sulfate content is 0.2-0.3 g, and the sodium chloride content is 45-55 g.

According to a preferred embodiment of the present disclosure, the fermentation medium is 3 #fermentation medium comprising glucose, corn steep liquor powder (enzymolysis), urea, dipotassium hydrogen phosphate, disodium hydrogen phosphate, magnesium sulfate and sodium chloride; relative to 1 L of fermentation medium, the content of glucose is 15-30 g, the content of corn steep liquor powder is 15-21 g, the content of urea is 1.5-2.5 g, the content of dipotassium hydrogen phosphate is 2-5 g, the content of disodium hydrogen phosphate is 5-8 g, the content of magnesium sulfate is 0.2-0.3 g, and the content of sodium chloride is 45-55 g.

The content of each substance mentioned above refers to the content of each substance in the medium, instead of the total feed amount of each substance.

According to the present disclosure, preferably, the above components are subjected to the treatment of removing impurities before being used for preparing the culture medium, or the fermentation medium is preferably subjected to the treatment of removing impurities before inoculating PHA fermentation strains into the fermentation medium; the methods of removing impurities may include but are not limited to one or more selected from the group consisting of gauze filtration, plate and frame filtration, vacuum filtration and membrane filtration.

According to the present disclosure, the temperature of PHA fermentation may be the conventional fermentation temperature, the temperature is preferably within a range of 30–45° C. and may be, for example, 30° C., 31° C., 32° C., 33° C., 34° C., 35° C., 35.5° C., 36° C., 36.5° C., 37° C., 37.5° C., 38° C., 38.5° C., 39° C., 40° C., 41° C., 42° C., 43° C., 44° C. and 45° C. More preferably, the temperature is within a range of 35-39° C.

The pH of PHA fermentation according to the present disclosure may be at its conventional fermentation pH, preferably, the pH is between 7 and 9, and may be, for example, 7, 7.5, 8, 8.3, 8.4, 8.5, 8.6, 8.7, 8.8, 9. More preferably, the pH is within a range of 8.3-8.7. The pH can be adjusted by using the customary alkali, for example, sodium hydroxide solution with a concentration of 8-12 mol/L.

According to the present disclosure, the amount of dissolved oxygen in PHA fermentation may be within the range of the conventional amount of dissolved oxygen in fermentation, preferably, the amount of dissolved oxygen is within a range of 1-40%, for example 1%, 2%, 3%, 4%, 5%, 10%, 15%, 20%, 25%, 30%, 35%, 40%. More preferably, the amount of dissolved oxygen is within a range of 1-30%.

According to the present disclosure, it is preferable that the conditions for the PHA fermentation further comprise a control of the ventilation quantity, which is preferably within a range of 0.5-1.5 vvm, and may be, for example, 0.5 vvm, 0.6 vvm, 0.7 vvm, 0.8 vvm, 0.9 vvm, 1 vvm, 1.1 vvm, 1.2 vvm, 1.3 vvm, 1.4 vvm, 1.5 vvm, preferably 1-1.2 vvm.

In accordance with the present disclosure, it is preferable that the conditions of PHA fermentation further comprises stirring, wherein the rotation speed of the stirring can be selected within a wide range, and preferably, the rotation speed of the stirring is within a range of 400-1,000 rpm, for example, 400 rpm, 450 rpm, 500 rpm, 550 rpm, 600 rpm, 650 rpm, 700 rpm, 750 rpm, 800 rpm, 850 rpm, 900 rpm, 950 rpm, 1,000 rpm, in terms of a 2-7 L fermentor.

The inventors of the present disclosure have discovered in the research course that the final fermentation effect can be further improved by controlling different rotation speeds of stirring in different fermentation stages. Preferably, the fermentation is performed under the stirring conditions, from 0 h to 8-12 h (for example, 0-8 h, 0-9 h, 0-10 h, 0-11 h, 0-12 h) and preferably to 9-11 h, and the rotation speed of stirring is within a range of 400-600 rpm;

From 8-12 h (preferably 9-11 h) to 16-20 h (for example, 8-16 h, 9-17 h, 10-18 h, 11-19 h, 12-20 h, 9-20 h, 10-20 h and the like, preferably 17-19 h, the specific starting time is determined according to the ending time of the last stage) of fermentation, the rotation speed of stirring is within a range of 600-1,000 rpm;

From 16-20 h (preferably 17-19 h) to the end (e.g., from 16 h to the end, from 17 h to the end, from 18 h to the end, from e 19 h to the end, from 20 h to the end, with the start time being determined by the end time of the last stage) of fermentation, the rotation speed of stirring is within a range of 400-600 rpm.

According to the present disclosure, the PHA fermentation can be carried out in a circumstance of without replenishing the feed material, or in a circumstance of replenishing the feed materials. According to a preferred embodiment of the present disclosure, the PHA fermentation is a fed-batch fermentation, i.e. replenishing the nutrient substances during the fermentation process.

According to the present disclosure, the timing of adding the nutrient substances can be determined based on the demand of the PHA fermentation species for sugar, preferably, the replenishment of the nutrient substances is started when the sugar content in the fermentation medium drops below 12 g/L, preferably below 10 g/L, more preferably below 5-8 g/L (e.g., 5 g/L, 6 g/L, 7 g/L, 8 g/L).

Wherein the amount of the nutrient substances to be replenished is preferably such that the sugar content in the fermentation medium is controlled to be within a range of 5-20 g/L, for example, 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, preferably 8-15 g/L.

Wherein the sugar content refers to the sugar content in the fermentation centrifugation supernatant measured by using the SBA-90 biological sensing analyzer.

Wherein, the sugar content in the fermentation system is preferably monitored in real time during the fermentation process.

Preferably, the fermentation may be terminated when the increase in $OD_{600}$ of the fermentation broth is less than 5/h, and according to the inventors' fermentation experience, the increase in $OD_{600}$ may be reduced to the above level when the fermentation is performed for 36-60 hours, preferably 39-42 hours.

Wherein, $OD_{600}$ refers to the light absorption value of the fermentation broth in a spectrophotometer at a wavelength of 600 nm.

Among them, it is preferable to monitor the $OD_{600}$ in the fermentation system in real time during the fermentation process.

According to the present disclosure, the nutrient substance may be a feed material in a conventional fermentation process, as long as the above requirements are met.

The inventors of the present disclosure have further discovered that the fermentation effect can be further improved by adding different nutrient substances at different stages of the fermentation process, and preferably, the method of replenishing nutrient substances comprises the following steps:

(1) replenishing a first nutrient substance when the sugar content in the fermentation medium drops below 12 g/L, preferably below 10 g/L, more preferably below 5-8 g/L for the first time, the first nutrient substance has a carbon-nitrogen ratio of 10-20:1; the replenishment amount of the first nutrient substance is 8-12% by volume of the fermentation medium.

According to a preferred embodiment of the present disclosure, the first nutrient substance comprises high-salt molasses and yeast powder. Preferably, the content of the high-salt molasses is 550-830 ml and the content of the yeast powder is 80-120 g relative to 1 L of the first nutrient substance.

According to a preferred embodiment of the present disclosure, the first nutrient substance comprises corn steep liquor and glucose. Preferably, the content of corn steep liquor is 480-690 ml, preferably 480-552 ml, and the content of glucose is 480-720 g, preferably 540-600 g, relative to 1 L of the first nutrient substance.

According to a preferred embodiment of the present disclosure, the first nutrient substance comprises glucose, corn steep liquor, urea, dipotassium hydrogen phosphate, disodium hydrogen phosphate, and magnesium sulfate. Preferably, the content of glucose is 400-500 g, the content of corn steep liquor is 42-50 g, the content of urea is 15-25 g, the content of dipotassium hydrogen phosphate is 2-3 g, the content of disodium hydrogen phosphate is 5-10 g, and the content of magnesium sulfate is 0.2-0.4 g, relative to 1 L of the first nutrient substance.

(2) After the first nutrient substance has been replenished, supplementing a second nutrient substance, wherein the second nutrient substance has a carbon-nitrogen ratio of 30-50:1; the replenishment amount of the second nutrient substance is 5-10% by volume of the fermentation medium.

According to a preferred embodiment of the present disclosure, the second nutrient substance comprises high-salt molasses and yeast powder. Preferably, the content of high-salt molasses is 830-980 ml and the content of yeast powder is 40-80 g relative to 1 L of the second nutrient.

According to a preferred embodiment of the present disclosure, the second nutrient substance comprises corn steep liquor and glucose. Preferably, the content of corn steep liquor is 272-326 ml, preferably 272-282 ml, and the content of glucose is 680-1,000 g, preferably 765-850 g, relative to 1 L of the second nutrient substance.

According to a preferred embodiment of the present disclosure, the second nutrient substance comprises glucose, corn steep liquor and urea. Preferably, the content of glucose is 400-500 g, the content of corn steep liquor is 35-40 g and the content of urea is 5-10 g relative to 1 L of the second nutrient substance.

Wherein the second nutrient substance can be replenished immediately after the first nutrient substance is supplemented, or at a certain time interval, but the time intervals shall enable that the sugar content in the fermentation medium is within a range of 5-20 g/L, preferably 8-15 g/L.

(3) After the replenishment of the second nutrient substance has been finished, a third nutrient substance is supplemented, wherein the third nutrient substance is a carbon source, and the replenishment amount of the third nutrient substance is 20-30% by volume of the fermentation medium.

According to a preferred embodiment of the present disclosure, the third nutrient is high-salt molasses.

According to a preferred embodiment of the present disclosure, the third nutrient substance is glucose, the content of glucose is within a range of 700-900 g, preferably 750-850 g, relative to 1 L of the third nutrient substance.

According to a preferred embodiment of the present disclosure, the third nutrient substance is glucose, and the content of glucose is 600-700 g relative to 1 L of the third nutrient substance.

Wherein the third nutrient substance can be replenished immediately after the second nutrient substance is supplemented, or at a certain time interval, but the time interval shall enable that the sugar content in the fermentation medium is within a range of 5-20 g/L, preferably 8-15 g/L.

Preferably, the fermentation process is terminated at 1-3 hours after completing the replenishment of the third nutrient substance.

According to the present disclosure, the nutrient substances can be replenished in an intermittent or fed-batch manner, and the skilled person in the art can determine the mode according to the practical condition.

According to the present disclosure, the fermentation process for producing PHA may be continuous fermentation or intermittent fermentation.

According to the present disclosure, the PHA fermentation strains can be various conventional halophilic fermentation strains being capable of producing PHA through fermentation, and preferably, the PHA fermentation strain is Halobacteriaceae or *Halomonas* sp.; more preferably, the PHA fermentation strain is *Halomonas* sp. TD01 with the preservation number of CGMCC NO. 4353 (CN 201010578858.8).

According to the present disclosure, the inoculated amount of the fermentation strains may not be particularly limited, and preferably, the inoculated amount of the fermentation strains is within a range of 5-15 vol %; for example, may be 5 vol %, 7 vol %, 9 vol %, 11 vol %, 13 vol %, 15 vol %, relative to 1 L of the fermentation medium.

According to the present disclosure, the fermentation strains inoculated into the fermentation medium is preferably the activated fermentation seed solution, and the $OD_{600}$ value of the fermentation seed solution is preferably 3-5.

Wherein the activation can be performed by means of conventional technical means in the art, such as inoculating a cryopreserved strain into a seed culture medium for activation culture. The seed culture medium may contain 5-10 g/L yeast powder, 10-15 g/L peptone and 50-60 g/L sodium chloride, and is obtained by high-temperature high-pressure sterilization.

Wherein, the conditions of the activation culture preferably comprise: the temperature is within a range of 30–40° C., the rotation speed is 150-250 rpm, and the cultivation is carried out until the $OD_{600}$ reaches 3-5.

Among them, the activation culture is preferably a multistage activation culture, for example, 2 to 3 stages, so that a sufficiently activated seed solution is obtained.

Step (2)

According to the present disclosure, the first solid-liquid separation method may be performed according to a conventional operation in the art, for example, the method may be at least one of the group consisting of a natural sedimentation method, a membrane filtration method, a centrifugal separation method, and a plate and frame filtration method.

According to a preferred embodiment of the present disclosure, the first solid-liquid separation is a plate and frame filtration separation, and the filter cloth of the plate and frame filtration is pre-coated with a polyhydroxyalkanoate layer.

According to the present disclosure, in the first solid-liquid separation, it is also preferable to remove the fermentation liquid remaining in the thallus precipitate (filter cake), for example, blowing out the residual fermentation liquid in the filter cake by a compressed air purge method, and the pressure of the compressed air may be within a range of 0.05-0.8 MPa, preferably 0.1 to 0.6 MPa, and more preferably 0.3-0.6 MPa.

According to the present disclosure, preferably, before breaking the cell walls of the thallus, the method further comprises washing the thallus precipitate obtained by the first solid-liquid separation with water to further remove the residual fermentation liquid. The water washing method may comprise immersing the resulting thallus in washing water for 10-120 min, preferably 30-90 min, more preferably 40-60 min. The washing water is preferably used in an amount capable of soaking the thallus precipitate.

Wherein the washing water may be purified water.

According to the present disclosure, the number of water washing may be 2-5 times.

The water washing is preferably countercurrent water washing or rotational flow washing, more preferably countercurrent washing, that is, the water washing liquid separated from the $n+1^{th}$ of washing is used as the water for washing the $n^{th}$ time.

According to the present disclosure, after the completion of the washing with water, a thallus precipitate can be obtained with the same method as the first solid-liquid separation.

According to the present disclosure, the water wash liquid separated after termination of the washing step can also be used as the PHA process wastewater, which is at least part of the water of the fermentation medium.

Step (3)

According to the present disclosure, the method for breaking cell walls may be a conventional method for breaking cell walls in the art, such as, but not limited to, at least one of the group consisting of an organic solvent method, a physical mechanical crushing method, a surfactant method, an enzymatic method, an alkaline method, and a pressurizing and heating method.

In accordance with a preferred embodiment of the present disclosure, the method of breaking the cell walls comprises a pressurizing and heating method, which does not introduce a third component, thereby effectively increasing purity of the final PHA product. Preferably, the conditions for breaking the cell walls by the boiling method preferably comprise that the temperature is within a range of 60-200° C., the pressure is 0.1-0.3 MPa, the rotation speed of stirring is 50-450 rpm, and the time is 10-240 min; more preferably, the temperature is 90-135° C., the pressure is 0.1-0.25 MPa, the rotation speed of stirring is 80-400 rpm, and the time is 20-150 min. if the method is performed within the preferred ranges, the recovery rate and purity of the finally obtained PHA can be further improved.

According to a preferred embodiment of the present disclosure, the method of breaking cell walls comprises an enzymatic method (e.g., may be at least one of lysozyme, protease, and lipase) and an organic solvent method (e.g., SDS method, i.e., sodium dodecyl sulfate method) sequentially performed. Preferably, (1) in the presence of lysozyme, performing a first cell wall breaking on the thallus precipitate to obtain first slurry containing polyhydroxyalkanoate; (2) carrying out solid-liquid separation in regard to the first slurry to obtain a precipitate containing polyhydroxyalkanoate; (3) in the presence of SDS, performing a second cell wall breaking on the precipitate containing the polyhydroxyalkanoate to obtain a wall-broken product.

Wherein the thallus precipitate can exist in the form of bacterial suspension, wherein the content of lysozyme in the bacterial suspension may be within a range of 0.05-1 g/L (for example, 0.05 g/L, 0.10 g/L, 0.15 g/L, 0.2 g/L, 0.25 g/L, 0.3 g/L, 0.35 g/L, 0.4 g/L, 0.45 g/L, 0.5 g/L, 0.6 g/L, 0.7 g/L, 0.8 g/L, 0.9 g/L, 1 g/L, or any value therebetween), and further preferably 0.1-0.5 g/L.

Preferably, the volume ratio of the water used for preparing the bacterial suspension relative to the thallus precipitate is within a range of 0.5-5:1 (for example, it may be 0.5:1, 0.6:1, 0.7:1, 0.8:1, 0.9:1, 1:1, 1.5:1, 2:1, 2.5:1, 3:1, 3.5:1, 4:1, 5:1, or any value therebetween), more preferably 0.8-2:1.

Preferably, the first cell wall breaking is performed under a condition including a pH of 4-9.

In the present disclosure, the time for the first cell wall breaking is not particularly limited and may be selected from a wide range, and preferably, the time for the first cell wall breaking is within a range of 60-240 min (for example, 60 min, 80 min, 100 min, 120 min, 150 min, 180 min, 200 min, 220 min, 240 min, or any value therebetween), and preferably 90-150 min.

In the present disclosure, the temperature of the first cell wall breaking is not particularly restrained and may be selected from a wide range, and preferably, the temperature of the first cell wall breaking is within a range of 20-50° C. (for example, 20° C., 25° C., 30° C., 35° C., 40° C., 45° C., 50° C., or any value therebetween), and preferably 30-40° C.

In the present disclosure, it is preferable that the first cell wall breaking is performed while stirring, the rotation speed of stirring is within a range of 50-350 rpm (for example, 50 rpm, it may be 50 rpm, 55 rpm, 60 rpm, 80 rpm, 100 rpm, 120 rpm, 150 rpm, 180 rpm, 200 rpm, 250 rpm, 300 rpm, 350 rpm, or any value therebetween), preferably 200-300 rpm.

In the present disclosure, it is preferable that before performing cell wall breaking with SDS, the method further comprises initially mixing the obtained precipitate containing polyhydroxyalkanoate with water to obtain a turbid liquid.

More preferably, the volume ratio of water used for preparing the turbid liquid relative to the precipitate is within a range of 0.5-5:1 (e.g., it may be 0.5:1, 0.6:1, 0.7:1, 0.8:1, 0.9:1, 1:1, 1.5:1, 2:1, 2.5:1, 3:1, 3.5:1, 4:1, 5:1, or any value therebetween), more preferably 0.8-2:1.

In the present disclosure, it is preferable that the weight ratio of the SDS relative to the precipitate containing polyhydroxyalkanoate is within a range of 0.05-0.3:1000, and more preferably 0.08-0.1:1000.

Preferably, the second cell wall breaking is performed at a pH of 8-11.5.

In the present disclosure, the time for the second cell wall breaking is not particularly limited and may be selected from a wide range, and the time for the second cell wall breaking is within a range of 20-180 min (for example, the time may be 20 min, 30 min, 40 min, 50 min, 60 min, 80 min, 100 min, 120 min, 150 min, 180 min, or any value therebetween), preferably 60-90 min.

In the present disclosure, the temperature of the second cell wall breaking is not particularly limited and may be selected from a wide range, it is preferable that the temperature of the second cell wall breaking is within a range of 60–90° C. (for example, 60° C., 65° C., 70° C., 75° C., 80° C., 85° C., 90° C., or any value therebetween), and more preferably 70-80° C.

In the present disclosure, in order to further improve the effect of breaking the thallus cells, it is preferable that the second cell-wall breaking is performed while stirring, the rotation speed of stirring is within a range of 50-350 rpm (50 rpm, 55 rpm, 60 rpm, 80 rpm, 100 rpm, 120 rpm, 150 rpm, 180 rpm, 200 rpm, 250 rpm, 300 rpm, 350 rpm, or any value therebetween), more preferably 100-300 rpm.

According to a preferred embodiment of the present disclosure, the method of cell wall breaking comprises an alkaline process, for example, the cell wall breaking is performed in the presence of ammonia. For example, the thallus precipitate may be re-suspended according to the aforementioned method to obtain a bacterial suspension, the ammonia liquor is then added into the bacterial suspension to break the cell wall.

The concentration of ammonia, calculated in terms of $NH_4OH$, in the bacterial suspension is within a range of 0.1-1 mol/L (e.g., the concentration may be 0.1 mol/L, 0.2 mol/L, 0.3 mol/L, 0.4 mol/L, 0.5 mol/L, 0.6 mol/L, 0.7 mol/L, 0.8 mol/L, 0.9 mol/L, 1.0 mol/L, or any value therebetween), preferably 0.2-0.5 mol/L.

The time for breaking the cell wall with the ammonia liquor is not particularly limited, and may be selected from a wide range, it is preferable that the time is within a range of 20-180 min (for example, 20 min, 30 min, 40 min, 50 min, 60 min, 80 min, 100 min, 120 min, 150 min, 180 min, or any value therebetween), and more preferably 60 to 90 min.

In the present disclosure, the temperature for breaking the cell wall with the ammonia liquor is not particularly limited and may be selected from a wide range, the temperature is preferably within a range of 60–90° C. (for example, 60° C., 65° C., 70° C., 75° C., 80° C., 85° C., 90° C., or any value therebetween), and more preferably 70-80° C.

In the present disclosure, it is preferable that the stirring is performed while breaking cell walls with ammonia liquor, and the rotation speed of stirring is within a range of 50-350 rpm (50 rpm, 55 rpm, 60 rpm, 80 rpm, 100 rpm, 120 rpm, 150 rpm, 180 rpm, 200 rpm, 250 rpm, 300 rpm, 350 rpm, or any value therebetween), more preferably 200-300 rpm.

According to the present disclosure, in order to further improve the effect of breaking cell wall thereby increasing the PHA yield, it is preferable to perform non-physical mechanical crushing method in combination with physical mechanical crushing method for breaking cell wall, for example, the ultrasonic and/or homogenization method.

The inventors of the present disclosure have discovered that the degradation of PHA can be remarkably relieved by using ultrasonic wave for auxiliary extraction, so that the obtained PHA has higher polymerization degree. In the present disclosure, the polymerization degree of polyhydroxyalkanoate (i.e., the average polymerization degree) refers to the number of hydroxy fatty acid monomers in a polymer molecule, and is characterized by the weight average molecular weight. It is understood that the polymerization degree of the polyhydroxyalkanoate has a positive correlation with its weight average molecular weight.

In the present disclosure, the power of the ultrasound is not particularly limited and may be selected in a wide range, it is preferable that the power of the ultrasound is within a range of 200-2,000 $W/m^3$ material (for example, it can be 200 $W/m^3$ material, 300 $W/m^3$ material, 500 $W/m^3$ material, 800 $W/m^3$ material, 1,000 $W/m^3$ material, 1,500 $W/m^3$ material, 2,000 $W/m^3$ material, or any value therebetween), more preferably 300-1,000 $W/m^3$ material.

The inventors of the present disclosure finds out in research that the polymerization degree and the molecular uniformity of PHA can be more remarkably preserved by controlling the power of ultrasound in a staged manner during the process of carrying out ultrasonication, that is, the obtained PHA has higher polymerization degree and molecular weight, thereby improving the product quality of the PHA.

Preferably, the control mode of the ultrasound comprises: the first ultrasonic treatment is initially carried out, and then the second ultrasonic treatment is performed, wherein the power of the second ultrasonic treatment is 100-200 W/m$^3$ bacteria suspension higher than that of the first ultrasonic treatment. More preferably, the power of the first ultrasonic treatment is within a range of 300-800 W/m$^3$ bacterial suspension. Preferably, the time of the first ultrasonic treatment is 1/5-1/2 of the total time of breaking cell wall (i.e., the total time of ultrasonic treatment).

According to the present disclosure, the homogenization conditions may vary within a wide range, the homogenization pressure is within a range of 0.5-2.5 MPa, preferably 1 to 2 MPa.

According to the present disclosure, the physical mechanical crushing method may be incorporated into the pressurizing and heating method, may be incorporated into any one stage of a combined cell wall breaking process of an organic solvent method (e.g., SDS method) and an enzymatic method, e.g., a stage of breaking cell wall with an enzymatic method or a stage of breaking cell wall with SDS, and may also be incorporated into a process of breaking cell wall with ammonia liquor.

According to the present disclosure, it is preferable that before breaking cell wall of the thallus precipitate, the method further comprises adjusting pH of the cell precipitate to be within a range of 6-11, more preferably 7-10.

According to the present disclosure, before performing the plate and frame filtration in regard to the obtained product of breaking cell wall, it is preferable that the method further comprises subjecting the product of breaking cell wall to the treatment of removing impurities and purification. The inventors have discovered that the product of breaking cell wall mainly comprises PHA, thallus cell walls and a variety of intracellular components in various bacteria, however, the PHA and the cell walls are substantially insoluble in water. According to a preferred embodiment of the present disclosure, the centrifugation method is used for removing impurities in the product of breaking cell wall, the centrifugation condition causes that the impurities such as cell walls are in the upper layer and the PHA is located at the lower layer. In such a way, the upper layer not only contains most of insoluble impurities such as macromolecules, but also contains all of soluble impurities, and the lower layer is mainly consisting of the PHA insoluble matter. Wherein the centrifugation preferably uses a disk-type centrifuge.

Further preferably, the method further comprises washing the obtained PHA precipitate with water to further remove the residual liquid phase prior to the plate and frame filtration. The water washing method may comprise immersing the obtained PHA precipitate in washing water for 10-120 min, preferably 30-90 min, more preferably 40-60 min. Wherein the washing water is preferably used in an amount capable of soaking the PHA precipitate.

Wherein the washing water may be purified water.

According to the present disclosure, the number of the water washing may be 2-5 times.

The water washing is preferably countercurrent water washing or rotational flow washing, more preferably countercurrent washing, that is, the water washing liquid separated from the n+1$^{th}$ of washing is used as the water for washing the n$^{th}$ time.

According to the present disclosure, the water wash liquid separated after termination of the washing step can also be used as the PHA process wastewater, which is at least part of the water of the fermentation medium.

In the present disclosure, preferably, the particle size of the polyhydroxyalkanoate coated on the surface of the filter cloth used for the plate and frame filtration is larger than the particle size of the polyhydroxyalkanoate in the slurry. It shall be noted that the phrase "the particle size of the polyhydroxyalkanoate coated on the surface of the filter cloth used for the plate and frame filtration is larger than the particle size of the polyhydroxyalkanoate in the slurry" does not mean that the particle size of each polyhydroxyalkanoate particle of the polyhydroxyalkanoate coated on the filter cloth is larger than the particle size of each polyhydroxyalkanoate particle of the polyhydroxyalkanoate in the slurry, but means that the average particle size of the polyhydroxyalkanoate coated on the filter cloth is larger than the average particle size of the polyhydroxyalkanoate in the slurry.

Preferably, the polyhydroxyalkanoate coated on the surface of the filter cloth for the plate and frame filtration separation has a particle size within the range of 1-200 μm.

In the present disclosure, in order to further increase purity of the polyhydroxyalkanoate, the polyhydroxyalkanoate coated on the surface of the filter cloth used for the plate and frame filtration separation preferably has a thickness within a range of 1-30 mm, preferably 5-10 mm.

Preferably, the filter cloth pre-coated with the polyhydroxyalkanoate layer has a pore size within a range of 1-25 μm, more preferably 2-23 μm.

In the present disclosure, the method of coating the filter cloth surface with polyhydroxyalkanoate preferably includes: initially mixing the polyhydroxyalkanoate with water to prepare a suspension, and subsequently coating the obtained suspension on the filter cloth surface to obtain the filter cloth coated with polyhydroxyalkanoate.

In the present disclosure, the obtained polyhydroxyalkanoate may be dried as needed, the drying method may be spray drying, vacuum drying, fluidized bed drying, or pneumatic drying, preferably spray drying, the air inlet temperature is within a range of 80-200° C., preferably 100-180° C., and more preferably 120-180° C.

PHA Process Wastewater Reuse

According to the present disclosure, in order to utilize resources more effectively and ensure PHA fermentation efficiency, the present disclosure further includes performing a treatment of removing impurities of PHA process waste water obtained in each of the aforementioned stages, such as fermentation supernatant, thallus precipitate washing water and PHA precipitate washing water, and the methods of removing impurities include, but are not limited to, adsorption method, oxidation method, membrane separation method, chromatographic separation method and boiling method. The treated fermentation process wastewater is recycled and reused in the fermentation process.

Adsorption Method

The adsorption method may specifically comprise that an adsorbent is added into the PHA process wastewater to adsorb and treat impurities therein to obtain a recycled clear solution.

It is clear that the present disclosure aims to recycle the inorganic salts in the PHA process wastewater, thus the selection of the adsorbent shall be based on its capability of efficiently adsorbing the organic substances harmful to the PHA fermenting bacteria in the PHA process wastewater without substantially adsorbing the inorganic salts in the PHA process wastewater. Therefore, when the treated supernatant is recycled, the process of preparing the PHA fermentation medium may produce the favorable effects that the used amount of the water is saved, the used amount of inorganic salts is decreased, the discharge amount and treatment pressure of three wastes (waste water, waste gas and solid waste) are reduced. According to a preferred embodiment of the present disclosure, the adsorbent is one or more selected from the group consisting of carbonaceous adsorbent material, resin, bauxite, diatomaceous earth, non-metal oxide adsorbent material and metal oxide adsorbent material, and more preferably, the adsorbent is carbonaceous adsorbent material, preferably a carbon column and/or activated carbon.

According to a more preferred embodiment of the present disclosure, the adsorbent is a mixed adsorbent of activated carbon and carbon column, wherein the used amount ratio of activated carbon relative to carbon column is 1:0.5-2, more preferably 1:0.8-1.5, and for example, the ratio may be 1:0.8, 1:0.9, 1:1, 1:1.1, 1:1.2, 1:1.3, 1:1.4, 1:1.5.

According to the present disclosure, the used amount of the adsorbent can be selected from a wide range, and preferably, in order to improve the efficiency of treating the PHA process wastewater, thereby reducing the PHA production cost and ensure the subsequent PHA fermentation efficiency, the amount of the adsorbent is within a range of 2-200 g, for example, 2 g, 5 g, 12 g, 22 g, 35 g, 55 g, 90 g, 120 g, 150 g, 180 g, 200 g, more preferably within a range of 10-50 g, for example, 10 g, 12 g, 15 g, 20 g, 22 g, 25 g, 30 g, 35 g, 40 g, 45 g, 50 g, relative to 1 L of the PHA process wastewater.

According to the present disclosure, the adsorption conditions can be selected within a wide range, and preferably, in order to improve the efficiency of the treatment of the fermentation broth, thereby reducing the PHA production cost and ensure the subsequent PHA fermentation efficiency, the adsorption is performed under the stirring condition, and the adsorption temperature is within a range of 0–40° C., for example, it may be 0° C., 5° C., 10° C., 15° C., 20° C., 25° C., 30° C., 35° C., 40° C., more preferably 15-30° C.; the adsorption time is within a range of 5-120 min, for instance, the adsorption time may be 5 min, 10 min, 15 min, 20 min, 25 min, 30 min, 35 min, 40 min, 45 min, 50 min, 55 min, 60 min, 70 min, 80 min, 90 min, 100 min, 110 min, 120 min, more preferably 20-40 min; the rotation speed of stirring is within a range of 50-1,000 rpm, and for example, it may be 50 rpm, 80 rpm, 100 rpm, 120 rpm, 150 rpm, 180 rpm, 200 rpm, 300 rpm, 400 rpm, 500 rpm, 600 rpm, 700 rpm, 800 rpm, 900 rpm, 1,000 rpm, and more preferably 100-150 rpm.

According to the present disclosure, it is preferable that the method further comprises subjecting the treated supernatant to a solid-liquid separation to obtain recycled supernatant and adsorbent waste; and then circulating the recycled supernatant to a fermentation stage of the polyhydroxyalkanoate for preparing a fermentation medium of the polyhydroxyalkanoate, and enabling the solid adsorbent waste to enter an adsorbent regeneration treatment stage.

The method for subjecting the treated supernatant to a solid-liquid separation may be a conventional solid-liquid separation method, as long as the solid-phase and liquid-phase generated after adsorption can be effectively separated, and for example, a method of standing still, a method of filtration, or a method of centrifugation may be used. According to a preferred treatment mode in the present disclosure, in order to further reduce the production cost of PHA and ensure the fermentation efficiency of PHA fermentation strains after the salt-containing fermentation waste liquid is recycled, the solid-liquid separation mode is filtration; preferably, the filtration is performed by plate and frame filtration; the filtering conditions comprise: the temperature is within a range of 0-40° C., the pressure is 0.1-0.6 MPa, and the time is 0.5-5 hours; preferably, the temperature is within a range of 15-25° C., the pressure is 0.2-0.3 MPa, and the time is 2-3 hours.

According to the present disclosure, the method for regenerating the adsorbent waste may be an adsorbent regeneration method commonly used in the art, for example, the method may include high-temperature heating and desalting treatment. Wherein the high-temperature heating can be performed in a high-temperature regeneration furnace, and the temperature of the high-temperature heating is preferably selected to remove the organic matters adsorbed on the adsorbent through volatilization or decomposition. The desalting process may be performed by water washing, for example, the adsorbent following the high-temperature heating process is subjected to cooling and the cooled adsorbent is delivered to a pumped into a water washing tank for water washing and desalting.

According to the present disclosure, it is preferable that the method further comprises subjecting the adsorbent after water washing to a solid-liquid separation, wherein the separated solid phase can be used as solid adsorbent for next adsorption separation, and the obtained liquid phase can be used as the PHA process wastewater. The solid-liquid separation is preferably carried out through filtration by using a plate and frame filter.

Oxidation Method

In the oxidation method, specifically, the method may comprise: adding an oxidant into the PHA process wastewater to oxidize the PHA process wastewater in order to obtain a recycled clear solution.

According to the present disclosure, the oxidant may be various conventional oxidants, but the inventors of the present disclosure have found in their researches that the effect of the present disclosure can be further improved by using at least one of hydrogen peroxide, hypochlorous acid and sodium hypochlorite as the oxidant. Therefore, the oxidant is preferably at least one selected from the group consisting of hydrogen peroxide, hypochlorous acid and sodium hypochlorite.

According to a more preferred embodiment of the present disclosure, the oxidant is hydrogen peroxide or sodium hypochlorite.

According to the present disclosure, the used amount of the oxidant can be selected within a wide range, and preferably, in order to increase the treatment efficiency of the PHA process wastewater, thereby reducing the PHA production cost and securing the subsequent PHA fermentation efficiency, the used amount of the oxidant may cause that the concentration of the oxidant in the PHA process wastewater is 0.5-30 wt %, for example, 0.5 wt %, 1.5 wt %, 2.5 wt %, 5 wt %, 8 wt %, 12 wt %, 15 wt %, 18 wt %, 20 wt %, 25 wt %, 30 wt %, more preferably 5-18 wt %.

According to the present disclosure, the conditions of the oxidation treatment can be selected within a wide range, and preferably, in order to increase the treatment efficiency of the PHA process wastewater, thereby reducing the PHA production cost and ensuring the subsequent PHA fermentation efficiency, the oxidation treatment is carried out under the stirring condition, and the temperature of the oxidation treatment is within a range of 15-45° C., for example, 15° C., 20° C., 25° C., 30° C., 35° C., 40° C., 45° C., more preferably 20-30° C.; the time of the oxidation treatment is within a range of 10-300 min, for example, the time may be 10 min, 15 min, 20 min, 25 min, 30 min, 35 min, 40 min, 45 min, 50 min, 75 min, 100 min, 125 min, 150 min, 175 min, 200 min, 225 min, 250 min, 275 min, 300 min, more preferably 120-240 min; the rotation speed of stirring is within a range of 200-1,500 rpm, for instance, it may be 200 rpm, 300 rpm, 500 rpm, 700 rpm, 1,000 rpm, 1,300 rpm, 1,500 rpm, and more preferably 800-1,200 rpm.

According to the present disclosure, for the sake of further enhancing the effect of the present disclosure, it is preferable that the method further comprises subjecting the liquid phase after the oxidation treatment to manganese dioxide post-treatment, light irradiation post-treatment or acid post-treatment.

When the oxidant therein is hydrogen peroxide, manganese dioxide post-treatment is preferably carried out; when the oxidant is hypochlorous acid, the light irradiation post-treatment is preferably performed; when the oxidant is sodium hypochlorite, it is preferable to perform an acid post-treatment, and the acid may be hydrochloric acid.

Further preferably, the aforementioned post-treatments relate to contact under the stirring conditions, the temperature is within a range of 15-45° C., for example, it can be 15° C., 20° C., 25° C., 30° C., 35° C., 40° C., 45° C., more preferably 15-35° C.; the time is within a range of 10-300 min, for example, 10 min, 15 min, 20 min, 25 min, 30 min, 35 min, 40 min, 45 min, 50 min, 75 min, 100 min, 125 min, 150 min, 175 min, 200 min, 225 min, 250 min, 275 min, 300 min, more preferably 20-40 min; the rotation speed of stirring is within a range of 200-1,500 rpm, and may be 200 rpm, 300 rpm, 500 rpm, 700 rpm, 1,000 rpm, 1,300 rpm, 1,500 rpm, and more preferably 500-1,000 rpm.

According to the present disclosure, it is preferable that the method further comprises subjecting the liquid phase after oxidation treatment to a solid-liquid separation, so as to obtain recycled supernatant and solid particles; wherein the recycled supernatant can be recycled to the fermentation stage of the polyhydroxyalkanoate for preparing a fermentation medium of the polyhydroxyalkanoate, and the solid particles may be further treated according to requirements.

Membrane Separation Process

The membrane separation method may specifically comprise: subjecting the PHA process wastewater to the membrane filtration to remove impurities in the PHA process wastewater so as to obtain a recycled clear solution.

According to a preferred embodiment of the present disclosure, in order to further enhance the treatment effect of PHA process wastewater, the membrane filtration comprises a ceramic membrane filtration and an ultrafiltration membrane filtration sequentially performed. In the preferred case, the residual small-molecule solid suspended substances in the PHA process wastewater can be removed in one step by ceramic membrane filtration, and then the smaller suspended substances and insoluble thallus debris, denatured proteins, cytotoxins, pigments, and other substances that are difficult to be utilized can be removed by ultrafiltration membrane filtration, thereby obtaining a recyclable saline solution. According to the present disclosure, the pore size of the ceramic membrane (inorganic ceramic membrane) is preferably selected, as described above, such that the small molecule solid suspended substances remaining in the PHA process wastewater is further removed. The ceramic film preferably has a pore diameter within a range of 10-60 nm, more preferably 20-50 nm (for example, it may be 20 nm, 25 nm, 30 nm, 35 nm, 40 nm, 45 nm, or 50 nm); the pressure for the ceramic membrane filtration may be within a range of 0.1-0.5 MPa (for example, 0.1 MPa, 0.15 MPa, 0.2 MPa, 0.25 MPa, 0.3 MPa, 0.35 MPa, 0.4 MPa, 0.45 MPa, 0.5 MPa), preferably 0.2-0.4 MPa. The ceramic membrane is commercially available, for example, from the supplier Jiangsu JiuWu Hi-Tech Co., Ltd.

According to the present disclosure, the pore size of the ultrafiltration membrane is preferably selected, as described above, such that smaller suspended substance and large molecular organic matter in the PHA process wastewater are removed. Preferably, the interception weight average molecular weight of the ultrafiltration membrane is more than 800 daltons, preferably within a range of 800-6,000 Da, and further preferably within a range of 1,000-5,000 Da (for example, it may be 1,000 Da, 1,500 Da, 2,000 Da, 2,500 Da, 3,000 Da, 3,500 Da, 4,000 Da, 4,500 Da, 5,000 Da); the pressure for the ultrafiltration membrane filtration may be within a range of 0.2-1 MPa (for example, 0.2 MPa, 0.3 MPa, 0.4 MPa, 0.5 MPa, 0.6 MPa, 0.8 MPa or 1 MPa), preferably 0.3-0.6 MPa. The ultrafiltration membrane is commercially available, for example, from Shanghai Sai-ao Separation Technology Engineering Co., Ltd.

Chromatographic Separation Method

The chromatographic separation method may specifically include subjecting the fermentation supernatant to chromatographic adsorption treatment in a chromatographic column in order to obtain a recycled supernatant.

According to the present disclosure, the chromatographic separation medium used in the chromatographic adsorption treatment can be a variety of conventional chromatographic adsorption media, and for example, it may be one or more selected from the group consisting of a nonpolar macroporous adsorption resin, a weak polar macroporous adsorption resin, a strong polar macroporous adsorption resin and an ion exchange resin. According to a particularly preferred embodiment of the present disclosure, the chromatographic adsorption medium is an ion exchange resin, more preferably an anion exchange resin, e.g. a strongly alkaline anion exchange resin or a weakly alkaline anion exchange resin, for example, LX-98, LSA-700 or LSA-700B, which are commercially available from the Xi'an Sunresin Technology New Materials Stock Co., Ltd., or DA201A, DA201B, DA201M, 201*7, which are available from the Jiangsu Suqing Water Treatment Engineering Group Co., Ltd., or D201, which is commercially available from Langfang Nanda Resin Co., Ltd.

The category of the anion exchange resin is not particularly limited in the present disclosure, and may be various strongly alkaline anion exchange resins and/or weakly alkaline anion exchange resins generally known among the skilled person in the art. The strongly alkaline anion exchange resin may be a strongly alkaline styrene-based anion exchange resin and/or a strongly alkaline phenylenediene-based anion exchange resin. The weakly alkaline anion exchange resin may be weakly alkaline styrene anion exchange resin and/or weakly alkaline phenylenediene anion exchange resin.

In the present disclosure, it is preferable that the anion exchange resin is a strongly alkaline anion exchange resin, for example, a strongly alkaline styrene-based anion exchange resin and/or a strongly alkaline phenylenediene-based anion exchange resin. Most preferably, the strongly alkaline anion exchange resin is D201, which is commercially available from Langfang Nanda Resin Co., Ltd.

According to the present disclosure, the chromatographic adsorption conditions may be the conventional chromatographic adsorption condition. Preferably, in order to further enhance the effect of the present disclosure, the temperature of the chromatographic adsorption treatment is within a range of 0-40° C., for example, 0° C., 5° C., 10° C., 15° C., 20° C., 25° C., 30° C., 35° C., 40° C., more preferably 15-25° C.

According to the present disclosure, the flowing speed of the PHA process waste water in the chromatographic column can be selected in a wide range, preferably, for the sake of further enhancing the effect of the chromatographic adsorption treatment, the temperature of the chromatographic adsorption treatment is within a range of 0-40° C., and the flowing speed of the PHA process waste water in the chromatographic column is within a range of 1-3 BV/h, for example, it may be 1 BV/h, 1.5 BV/h, 2 BV/h, 2.5 BV/h, 3 BV/h, more preferably 1.5-2.5 BV/h.

According to the present disclosure, the volume of the chromatography column may be the conventional volume of a chromatography column in the art, and preferably, the volume of the chromatography column is within a range of 5-100 ml.

The method of the present disclosure may also comprise regenerating the chromatography column, the regeneration method may be conventional method of regenerating the chromatography column in the art, and for example, may comprise alkaline treatment and water washing. Specifically, the regeneration method may comprise: regenerating the resin column with sodium hydroxide solution having a concentration of 2-4 wt % in an amount of several times (e.g., 2-5 times) of the column volume at a flow rate of 1-3 BV/h and the temperature of 15-25° C. After termination of the regeneration process with the sodium hydroxide solution, the purified water elutes till the outlet liquid has a pH of 6-8.

The present disclosure will be described in detail below with reference to examples.

I. The Influence of PHA Fermentation Process on Fermentation Properties

The volume of the fermentation tank is 5 L, in addition, the method is also suitable for large-scale fermentation, for example, 10,000 L fermentation equipment.

Example 1—High-Salt Molasses Used as a Carbon Source

The high-salt cane molasses 1 is a waste material generated in a cane sugar refining process for producing sugar, it is in a thick liquid state, has a salt content about 10 wt %, and a sugar content about 51 wt % in terms of dry solids; it comprises glucose, sucrose and fructose, wherein the glucose content is 11 wt %, the sucrose content is 81 wt % and the fructose content is 8 wt % in terms of total sugar.

The high-salt cane molasses 2 is a waste material generated in a cane sugar refining process for producing sugar, it is in a thick liquid state, has a salt content about 9 wt %, and a sugar content about 60 wt % in terms of dry solids; it comprises glucose, sucrose and fructose, wherein the glucose content is 15 wt %, the sucrose content is 75 wt % and the fructose content is 10 wt % in terms of total sugar.

The high-salt cane molasses 3 is a waste material generated in a cane sugar refining process for producing sugar, it is in a thick liquid state, has a salt content about 11 wt %, and a sugar content about 70 wt % in terms of dry solids; it comprises glucose, sucrose and fructose, wherein the glucose content is 10 wt %, the sucrose content is 85 wt % and the fructose content is 5 wt % in terms of total sugar.

The high-salt beet molasses 4 is a waste material generated in a cane sugar refining process for producing sugar, it is in a thick liquid state, has a salt content about 8 wt %, and a sugar content about 40 wt % in terms of dry solids; it comprises glucose, sucrose and fructose, wherein the glucose content is 5 wt %, the sucrose content is 83 wt % and the fructose content is 12 wt % in terms of total sugar.

The sugar content is measured according to a method of the SBA-90 biological sensing analyzer.

The method for measuring the biomass of *Halomonas* sp. in the fermentation broth comprises the following steps: taking 25-45 ml of the fermentation broth and centrifuging (8,000 rpm, 10 min), retaining the precipitate, washing the precipitate with sterile water for 2 times, drying the washed precipitate for 48 hours by using a vacuum freeze dryer, and weighing the dried precipitate.

Reference literature: Chung A, Liu Q, Ouyang S P, et al, Microbial production of 3-hydroxydecanoic acid by Phaoperon and fadBA knock out mutant of *Pseudomonas putida* KT2442 harboring tesB gene [J]. *Applied Microbial & Biotechnology*, 2009, 83(3): 513-519. Extraction of PHA from fermentation broth.

Preparation Example 1-1

The Preparation Example was used for illustrating the activation of the fermentation broth.

Seed culture medium: comprising 8 g/L yeast powder, 12 g/L peptone and 55 g/L sodium chloride.

The *Halomonas* sp. was inoculated into a seed culture medium to perform primary activation culture under the conditions consisting of a temperature of 37° C. and a rotation speed of 200 rpm until $OD_{600}$ reached about 4 so as to obtain a primary seed solution;

The primary seed solution was noculated into a seed culture medium according to the inoculation amount of 10 vol %, the secondary activation culture was performed under the conditions consisting of a temperature of 37° C. and a rotation speed of 200 rpm until $OD_{600}$ reached about 4 so as to obtain a secondary seed solution and a fermented seed solution.

Example 1-1

The example served to explain the method of preparing PHA through fermentation provided by the present disclosure.

Fermentation medium: the content of the high-salt molasses 1 was 25 mL, the content of yeast powder was 17 g, the content of dipotassium hydrogen phosphate was 3.5 g, the content of disodium hydrogen phosphate was 6.2 g, the content of magnesium sulfate was 0.25 g, and the content of sodium chloride was 55 g, relative to 1 L of the fermentation medium. The pH was adjusted to 8.5.

Replenishment material I: the high-salt molasses 1 and the yeast powder were taken as a carbon source and a nitrogen source respectively; the carbon/nitrogen ratio was 16:1. Wherein 640 mL of high-salt molasses 1 and 108 g of the yeast powder were replenished relative to 1 L of first nutrient substances; the volume ratio of the used amount of the replenishment material I relative to the fermentation medium was 9:100;

Replenishment material II: the high-salt molasses 1 and the yeast powder were taken as a carbon source and a nitrogen source respectively; the carbon/nitrogen ratio was 40:1. Wherein 900 mL of high-salt molasses 1 and 69.4 g of the yeast powder were replenished relative to 1 L of second nutrient substances; the volume ratio of the used amount of the replenishment material II relative to the fermentation medium was 6:100;

Replenishment material III: the high-salt molasses 1 was taken as a carbon source, the volume ratio of the used amount of the replenishment material III relative to the fermentation medium was 23:100.

The seed solution prepared in the Preparation Example was inoculated into a fermentation medium with an inoculation amount of 10 vol %, and the fermentation culture was performed under the conditions consisting of a temperature of 37° C. and a ventilation quantity of 1 vvm, wherein the pH in the fermentation process was controlled to be about 8.5, and the dissolved oxygen amount was controlled to be within a range of 10-30%. In addition, the rotation speed of stirring was controlled in stages during the fermentation process, wherein the rotation speed of stirring was 400 rpm during the fermentation time period of 0-10 h; the rotation speed of stirring was 800 rpm during the fermentation time period of 10-18 h; the rotation speed of stirring was 400 rpm during the fermentation time period starting from the 18 h to the termination of fermentation process.

The sugar content and pH of the fermentation system were monitored in real time during the fermentation process.

The replenishment material I was fed in batch when the sugar content in the fermentation system was reduced to below 6 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 10 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 1.

Example 1-2

The example served to explain the method of preparing PHA through fermentation provided by the present disclosure.

Fermentation medium: the content of the high-salt molasses 1 was 35 mL, the content of yeast powder was 15 g, the content of dipotassium hydrogen phosphate was 2.5 g, the content of disodium hydrogen phosphate was 6.5 g, the content of magnesium sulfate was 0.3 g, and the content of sodium chloride was 45 g, relative to 1 L of the fermentation medium. The pH was adjusted to 8.3.

Replenishment material I: the high-salt molasses 1 and the yeast powder were taken as a carbon source and a nitrogen source respectively; the carbon/nitrogen ratio was 15:1. Wherein 783 mL of high-salt molasses 1 and 120 g of the yeast powder were replenished relative to 1 L of first nutrient substances; the volume ratio of the used amount of the replenishment material I relative to the fermentation medium was 10:100.

Replenishment material II: the high-salt molasses 1 and the yeast powder were taken as a carbon source and a nitrogen source respectively; the carbon/nitrogen ratio was 38:1. Wherein 830 mL of high-salt molasses 1 and 80 g of the yeast powder were replenished relative to 1 L of second nutrient substances; the volume ratio of the used amount of the replenishment material II relative to the fermentation medium was 7:100.

Replenishment material III: the high-salt molasses 1 was taken as a carbon source, the volume ratio of the used amount of the replenishment material III relative to the fermentation medium was 25:100.

The seed solution prepared in the Preparation Example was inoculated into a fermentation medium with an inoculation amount of 12 vol %, and the fermentation culture was performed under the conditions consisting of a temperature of 35° C. and a ventilation quantity of 1.1 vvm, wherein the pH in the fermentation process was controlled to be about 8.3, and the dissolved oxygen amount was controlled to be within a range of 10-30%. In addition, the rotation speed of stirring was controlled in stages during the fermentation process, wherein the rotation speed of stirring was 500 rpm during the fermentation time period of 0-9 h; the rotation speed of stirring was 900 rpm during the fermentation time period of 9-17 h; the rotation speed of stirring was 500 rpm during the fermentation time period starting from the 17 h to the termination of fermentation process.

The sugar content and pH of the fermentation system were monitored in real time during the fermentation process.

The replenishment material I was fed in batch when the sugar content in the fermentation system was reduced to below 5 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 8 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 1.

Example 1-3

The example served to explain the method of preparing PHA through fermentation provided by the present disclosure.

Fermentation medium: the content of the high-salt molasses 1 was 15 mL, the content of yeast powder was 16 g, the content of dipotassium hydrogen phosphate was 4 g, the content of disodium hydrogen phosphate was 5.5 g, the content of magnesium sulfate was 0.2 g, and the content of sodium chloride was 50 g, relative to 1 L of the fermentation medium. The pH was adjusted to 8.5.

Replenishment material I: the high-salt molasses 1 and the yeast powder were taken as a carbon source and a nitrogen source respectively; the carbon/nitrogen ratio was 17:1. Wherein 560 mL of high-salt molasses 1 and 91 g of the yeast powder were replenished relative to 1 L of first nutrient substances; the volume ratio of the used amount of the replenishment material I relative to the fermentation medium was 11:100.

Replenishment material II: the high-salt molasses 1 and the yeast powder were taken as a carbon source and a nitrogen source respectively; the carbon/nitrogen ratio was 42:1. Wherein 875 mL of high-salt molasses 1 and 58 g of the yeast powder were replenished relative to 1 L of second nutrient substances; the volume ratio of the used amount of the replenishment material II relative to the fermentation medium was 8:100.

Replenishment material III: the high-salt molasses 1 was taken as a carbon source, the volume ratio of the used amount of the replenishment material III relative to the fermentation medium was 27:100.

The seed solution prepared in the Preparation Example was inoculated into a fermentation medium with an inoculation amount of 15 vol %, and the fermentation culture was performed under the conditions consisting of a temperature of 39° C. and a ventilation quantity of 1.2 vvm, wherein the pH in the fermentation process was controlled to be about 8.7, and the dissolved oxygen amount was controlled to be within a range of 10-30%. In addition, the rotation speed of stirring was controlled in stages during the fermentation process, wherein the rotation speed of stirring was 600 rpm during the fermentation time period of 0-11 h; the rotation speed of stirring was 1,000 rpm during the fermentation time period of 11-19 h; the rotation speed of stirring was 600 rpm during the fermentation time period starting from the 19 h to the termination of fermentation process.

The sugar content and pH of the fermentation system were monitored in real time during the fermentation process.

The replenishment material I was fed in batch when the sugar content in the fermentation system was reduced to below 8 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 15 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 1.

Example 1-4

The example served to explain the method of preparing PHA through fermentation provided by the present disclosure.

Fermentation medium: the content of the high-salt molasses 1 was 40 mL, the content of yeast powder was 10 g, the content of dipotassium hydrogen phosphate was 2.0 g, the content of disodium hydrogen phosphate was 5.0 g, the content of magnesium sulfate was 0.15 g, and the content of sodium chloride was 40 g, relative to 1 L of the fermentation medium. The pH was adjusted to 8.0.

Replenishment material I: the high-salt molasses 1 and the yeast powder were taken as a carbon source and a nitrogen source respectively; the carbon/nitrogen ratio was 18:1. Wherein 750 mL of high-salt molasses 1 and 116 g of the yeast powder were replenished relative to 1 L of first nutrient substances; the volume ratio of the used amount of the replenishment material I relative to the fermentation medium was 8:100.

Replenishment material II: the high-salt molasses 1 and the yeast powder were taken as a carbon source and a nitrogen source respectively; the carbon/nitrogen ratio was 34:1. Wherein 900 mL of high-salt molasses 1 and 74 g of the yeast powder were replenished relative to 1 L of second nutrient substances; the volume ratio of the used amount of the replenishment material II relative to the fermentation medium was 5:100.

Replenishment material III: the high-salt molasses 1 was taken as a carbon source, the volume ratio of the used amount of the replenishment material III relative to the fermentation medium was 20:100.

The seed solution prepared in the Preparation Example was inoculated into a fermentation medium with an inoculation amount of 10 vol %, and the fermentation culture was performed under the conditions consisting of a temperature of 30° C. and a ventilation quantity of 1.5 vvm, wherein the pH in the fermentation process was controlled to be about 8. In addition, the rotation speed of stirring was controlled to be about 800 rpm during the fermentation process.

The sugar content and pH of the fermentation system were monitored in real time during the fermentation process.

The replenishment material I was fed in batch when the sugar content in the fermentation system was reduced to below 10 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 5 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 1.

Example 1-5

The example served to explain the method of preparing PHA through fermentation provided by the present disclosure.

Fermentation medium: the content of the high-salt molasses 1 was 15 mL, the content of yeast powder was 20 g, the content of dipotassium hydrogen phosphate was 5 g, the content of disodium hydrogen phosphate was 8 g, the content of magnesium sulfate was 0.5 g, and the content of sodium chloride was 70 g, relative to 1 L of the fermentation medium. The pH was adjusted to 9.

Replenishment material: the replenishment material in the Example 1 was used. The volume ratio of the used amount of the replenishment material relative to the fermentation medium was 42:100.

The seed solution prepared in the Preparation Example was inoculated into a fermentation medium with an inoculation amount of 10 vol %, and the fermentation culture was performed under the conditions consisting of a temperature of 45° C. and a ventilation quantity of 0.5 vvm, wherein the pH in the fermentation process was controlled to be about 9, and the dissolved oxygen amount was controlled to be within a range of 10-30%. In addition, the rotation speed of stirring was controlled in stages during the fermentation process, wherein the rotation speed of stirring was 400 rpm during the fermentation time period of 0-12 h; the rotation speed of stirring was 800 rpm during the fermentation time period of 12-20 h; the rotation speed of stirring was 400 rpm during the fermentation time period starting from the 20 h to the termination of fermentation process.

The sugar content and pH of the fermentation system were monitored in real time during the fermentation process.

Only the replenishment material I was fed in batch when the sugar content in the fermentation system was reduced to below 12 g/L for the first time.

The feeding rate of the replenishment materials in batch caused that the sugar content in the fermentation broth was maintained at about 20 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 1.

Example 1-6

The example served to explain the method of preparing PHA through fermentation provided by the present disclosure.

The PHA was prepared according to the method of Example 1-1, except that the high-salt molasses 1 was replaced with an equal amount of high-salt cane molasses 2.

The comparisons of biomass of *Halomonas* sp. in the fermentation broth, PHA yield and raw material cost per unit product were shown in Table 1.

Example 1-7

The example served to explain the method of preparing PHA through fermentation provided by the present disclosure.

The PHA was prepared according to the method of Example 1-1, except that the high-salt molasses 1 was replaced with an equal amount of high-salt cane molasses 3.

The comparisons of biomass of *Halomonas* sp. in the fermentation broth, PHA yield and raw material cost per unit product were shown in Table 1.

Example 1-8

The example served to explain the method of preparing PHA through fermentation provided by the present disclosure.

The PHA was prepared according to the method of Example 1-1, except that the high-salt molasses 1 was replaced with an equal amount of high-salt beet molasses 4.

The comparisons of biomass of *Halomonas* sp. in the fermentation broth, PHA yield and raw material cost per unit product were shown in Table 1.

Comparative Example 1-1

The Comparative Example serves to illustrate and compare the method of preparing PHA through fermentation provided by the present disclosure.

The PHA was prepared according to the method of Example 1-4, except that the high-salt molasses 1 was replaced with an equal amount of low-salt molasses, and the sodium chloride content in the fermentation medium was adjusted to be the same as that in the fermentation medium of the Example 1-4.

The comparisons of biomass of *Halomonas* sp. in the fermentation broth, PHA yield and raw material cost per unit product were shown in Table 1.

Comparative Example 1-2

The Comparative Example served to illustrate and compare the method of preparing PHA through fermentation provided by the present disclosure.

The PHA was prepared according to the method of Example 1-4, except that the high-salt molasses 1 was replaced with an equal amount of a mixture consisting of glucose, sucrose and fructose, and the sodium chloride content in the fermentation medium was adjusted to be the same as that in the fermentation medium of the Example 1-4.

The comparisons of biomass of *Halomonas* sp. in the fermentation broth, PHA yield and raw material cost per unit product were shown in Table 1.

Comparative Example 1-3

The Comparative Example serves to illustrate and compare the method of preparing PHA through fermentation provided by the present disclosure.

The PHA was prepared according to the method of Example 1-4, except that the high-salt molasses 1 was replaced with an equal amount of glucose, and the sodium chloride content in the fermentation medium was adjusted to be the same as that in the fermentation medium of the Example 1-4.

The comparisons of biomass of *Halomonas* sp. in the fermentation broth, PHA yield and raw material cost per unit product were shown in Table 1.

TABLE 1

| Numbers | Biomass (g/L) | PHA yield (g/L) | Fermentation raw material cost change (%) |
|---|---|---|---|
| Example 1-1 | 91 | 74 | −32 |
| Example 1-2 | 89 | 75 | −30 |
| Example 1-3 | 90 | 73 | −27 |
| Example 1-4 | 89 | 72 | −23 |
| Example 1-5 | 87 | 70 | −18 |
| Example 1-6 | 91 | 74 | −31 |
| Example 1-7 | 91 | 75 | −30 |
| Example 1-8 | 89 | 74 | −32 |
| Comparative Example 1-1 | 90 | 71 | −15 |
| Comparative Example 1-2 | 91 | 75 | +11 |
| Comparative Example 1-3 | 88 | 70 | 0 |

As can be seen from the results in Table 1, the technical solutions of the present disclosure can effectively reduce the production costs of PHA when the Example 1-4 was compared with the Comparative Examples 1-1 and 1-2; the technical solutions of the present disclosure can not only effectively reduce the production costs of PHA, but also improve the biomass of thallus in the fermentation broth and the yield of PHA when the Example 1-4 was compared with the Comparative Example 1-3. When the Examples 1-1 to 1-3 were compared with the Examples 1-4 to 1-5, it can be seen that the control of the fermentation process in the preferred embodiment of the present disclosure can further reduce the costs and increase the thallus biomass in the fermentation broth and the yield of PHA. If the Examples 1-1, 1-6 and 1-7 were compared with the Example 1-8, it can be seen that the fermentation effect may be further improved by selecting specific high-salt molasses and controlling the salt content and sugar content of the high-salt molasses within the range of the present disclosure.

Example 2—Corn Steep Liquor Used as a Nitrogen Source

The PHA fermentation strains were as described above in the Example 1;

The sugar content, method of measuring biomass of *Halomonas* sp. in the fermentation broth, and the method of extracting PHA from the fermentation broth were as shown in the Example 1;

The corn steep liquor is derived from the COFCO Biochemical Energy (Yushu) Co., Ltd.

Preparation Example 2-1

The preparation example was use for illustrating the activation of the fermentation broth.

The preparation method was same as that in the Preparation Example 1-1.

Preparation Example 2-2

The preparation example was used for illustrating the preparation of enzymatically hydrolyzed corn steep liquor.

1) The cellulase, hemicellulase, amylase and acid protease were added into the corn steep liquor with a solid content of 45 wt %, wherein the dosage of the cellulase was 0.09 part by weight, the dosage of the hemicellulose was 0.09 part by weight, the dosage of the amylase was 0.04 part by weight and the dosage of the acid protease was 0.15 part by weight, relative to 1,000 parts by weight of the corn steep liquor;

2) The enzymolysis was performed for 35 min under the conditions consisting of the rotation speed of stirring of 650 rpm, the temperature of 47° C. and pH of 5.5, the stirring process was then terminated to obtain the enzymolysis product, which was subjected to the ceramic membrane filtration (the filter membrane had a pore size of 250 nm) to prepare the enzymatically hydrolyzed corn steep liquor.

Comparative Preparation Example 2-1

The Example was used for explaining and comparing the preparation of the enzymatically hydrolyzed corn steep liquor.

The enzymatically hydrolyzed corn steep liquor was prepared in accordance with the method of the Preparation Example 2-2, except that the cellulase was replaced with an equal amount of hemicellulase.

Comparative Preparation Example 2-2

The Example was used for explaining and comparing the preparation of the enzymatically hydrolyzed corn steep liquor.

The enzymatically hydrolyzed corn steep liquor was prepared in accordance with the method of the Preparation Example 2-2, except that the cellulase was replaced with an equal amount of protease.

Comparative Preparation Example 2-3

The Example was used for explaining and comparing the preparation of the enzymatically hydrolyzed corn steep liquor.

The enzymatically hydrolyzed corn steep liquor was prepared in accordance with the method of the Preparation Example 2-2, except that the enzymatic product was not filtered after the completion of the enzymolysis.

Comparative Example 2-1

The Comparative Example served to illustrate and compare the method of preparing PHA through fermentation provided by the present disclosure.

Fermentation medium: the content of corn steep liquor (with a solid content of 45 wt %) was 32 mL, the content of glucose was 15 g, the content of dipotassium hydrogen phosphate was 3 g, the content of disodium hydrogen phosphate was 6.8 g, the content of magnesium sulfate was 0.2 g, and the content of sodium chloride was 45 g, relative to 1 L of the fermentation medium.

The pH was adjusted to 8.5.

Replenishment material I: the carbon/nitrogen ratio was 14:1, the content of the corn steep liquor was 552 ml, and the content of the glucose was 540 g relative to 1 L of the first nutrient substance; the volume ratio of the used amount of the replenishment material I relative to the fermentation medium was 9:100;

Replenishment material II: the carbon/nitrogen ratio was 35:1, the content of the corn steep liquor was 315 ml and the content of the glucose was 765 g relative to 1 L of the second nutrient substance; the volume ratio of the used amount of the replenishment material II relative to the fermentation medium was 6:100;

Replenishment material III: the content of glucose was 850 g relative to 1 L of the third nutrient substance; the volume ratio of the used amount of the replenishment material III relative to the fermentation medium was 23:100.

The seed solution prepared in the Preparation Example was inoculated into a fermentation medium with an inoculation amount of 10 vol %, and the fermentation culture was performed under the conditions consisting of a temperature of 37° C. and a ventilation quantity of 1 vvm, the pH in the fermentation process was controlled to be about 8.5, and the dissolved oxygen amount was controlled to be within a range of 10-30%. In addition, the rotation speed of stirring was controlled in stages during the fermentation process, wherein the rotation speed of stirring was 400 rpm during the fermentation time period of 0-10 h; the rotation speed of stirring was 800 rpm during the fermentation time period of 10-18 h; the rotation speed of stirring was 400 rpm during the fermentation time period starting from the 18 h to the termination of fermentation process.

The sugar content and pH of the fermentation system were monitored in real time during the fermentation process.

The replenishment material I was fed in batch when the sugar content in the fermentation system was reduced to below 6 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 10 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 2.

Example 2-1

The Example served to explain the method of preparing PHA through fermentation provided by the present disclosure.

The PHA fermentation was performed according to the method of the Comparative Example 2-1, except for that the corn steep liquor was replaced with the enzymolyzed corn steep liquor prepared in the Preparation Example 2.

The comparisons of biomass of *Halomonas* sp. in the fermentation broth, PHA yield and raw material cost per unit product were shown in Table 2.

Comparative Example 2-2

The Comparative Example served to illustrate and compare the method of preparing PHA through fermentation provided by the present disclosure.

Fermentation medium: the content of corn steep liquor (with a solid content of 40 wt %) was 34 mL, the content of glucose was 25 g, the content of dipotassium hydrogen phosphate was 3.5 g, the content of disodium hydrogen phosphate was 6 g, the content of magnesium sulfate was 0.52 g, and the content of sodium chloride was 50 g, relative to 1 L of the fermentation medium. The pH was adjusted to 8.3.

Replenishment material I: the carbon/nitrogen ratio was 16:1, the content of the corn steep liquor was 504 ml, and the content of the glucose was 560 g relative to 1 L of the first nutrient substance; the volume ratio of the used amount of the replenishment material I relative to the fermentation medium was 10:100;

Replenishment material II: the carbon/nitrogen ratio was 40:1, the content of the corn steep liquor was 282 ml and the content of the glucose was 794 g relative to 1 L of the second nutrient substance; the volume ratio of the used amount of the replenishment material II relative to the fermentation medium was 7:100;

Replenishment material III: the content of glucose was 800 g relative to 1 L of the third nutrient substance; the volume ratio of the used amount of the replenishment material III relative to the fermentation medium was 25:100.

The seed solution prepared in the Preparation Example was inoculated into a fermentation medium with an inoculation amount of 12 vol %, and the fermentation culture was performed under the conditions consisting of a temperature of 35° C. and a ventilation quantity of 1.1 vvm, the pH in the fermentation process was controlled to be about 8.3, and the dissolved oxygen amount was controlled to be within a range of 10-30%. In addition, the rotation speed of stirring was controlled in stages during the fermentation process, wherein the rotation speed of stirring was 500 rpm during the fermentation time period of 0-9 h; the rotation speed of stirring was 900 rpm during the fermentation time period of 9-17 h; the rotation speed of stirring was 500 rpm during the fermentation time period starting from the 17 h to the termination of fermentation process.

The sugar content and pH of the fermentation system were monitored in real time during the fermentation process.

The replenishment material I was fed in batch when the sugar content in the fermentation system was reduced to below 5 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 8 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 2.

Example 2-2

The Example served to explain the method of preparing PHA through fermentation provided by the present disclosure.

The PHA fermentation was performed according to the method of the Comparative Example 2-2, except for that the corn steep liquor was replaced with the enzymolyzed corn steep liquor prepared in the Preparation Example 2.

The comparisons of biomass of *Halomonas* sp. in the fermentation broth, PHA yield and raw material cost per unit product were shown in Table 2.

Comparative Example 2-3

The Comparative Example served to illustrate and compare the method of preparing PHA through fermentation provided by the present disclosure.

Fermentation medium: the content of corn steep liquor (with a solid content of 50 wt %) was 36 mL, the content of glucose was 30 g, the content of dipotassium hydrogen phosphate was 4 g, the content of disodium hydrogen phosphate was 7.5 g, the content of magnesium sulfate was 0.3 g, and the content of sodium chloride was 55 g, relative to 1 L of the fermentation medium. The pH was adjusted to 8.3.

Replenishment material I: the carbon/nitrogen ratio was 18:1, the content of the corn steep liquor was 480 ml, and the content of the glucose was 600 g relative to 1 L of the first nutrient substance; the volume ratio of the used amount of the replenishment material I relative to the fermentation medium was 11:100;

Replenishment material II: the carbon/nitrogen ratio was 45:1, the content of the corn steep liquor was 272 ml and the content of the glucose was 850 g relative to 1 L of the second nutrient substance; the volume ratio of the used amount of the replenishment material II relative to the fermentation medium was 8:100;

Replenishment material III: the content of glucose was 750 g relative to 1 L of the third nutrient substance; the volume ratio of the used amount of the replenishment material III relative to the fermentation medium was 27:100.

The seed solution prepared in the Preparation Example was inoculated into a fermentation medium with an inoculation amount of 15 vol %, and the fermentation culture was performed under the conditions consisting of a temperature of 39° C. and a ventilation quantity of 1.2 vvm, the pH in the fermentation process was controlled to be about 8.7, and the dissolved oxygen amount was controlled to be within a range of 10-30%. In addition, the rotation speed of stirring was controlled in stages during the fermentation process, wherein the rotation speed of stirring was 600 rpm during the fermentation time period of 0-11 h; the rotation speed of stirring was 1,000 rpm during the fermentation time period of 11-19 h; the rotation speed of stirring was 600 rpm during the fermentation time period starting from the 19 h to the termination of fermentation process.

The sugar content and pH of the fermentation system were monitored in real time during the fermentation process.

The replenishment material I was fed in batch when the sugar content in the fermentation system was reduced to below 8 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 15 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 2.

Example 2-3

The Example served to explain the method of preparing PHA through fermentation provided by the present disclosure.

The PHA fermentation was performed according to the method of the Comparative Example 2-3, except for that the corn steep liquor was replaced with the enzymolyzed corn steep liquor prepared in the Preparation Example 2.

The comparisons of biomass of *Halomonas* sp. in the fermentation broth, PHA yield and raw material cost per unit product were shown in Table 2.

Comparative Example 2-4

The Comparative Example served to illustrate and compare the method of preparing PHA through fermentation provided by the present disclosure.

Fermentation medium: the content of corn steep liquor (with a solid content of 10 wt %) was 5 mL, the content of glucose was 10 g, the content of dipotassium hydrogen phosphate was 2 g, the content of disodium hydrogen phosphate was 4 g, the content of magnesium sulfate was 0.1 g, and the content of sodium chloride was 40 g, relative to 1 L of the fermentation medium.

The pH was adjusted to 7.

Replenishment material I: the carbon/nitrogen ratio was 10:1, the content of the corn steep liquor was 690 ml, and the content of the glucose was 480 g relative to 1 L of the first nutrient substance; the volume ratio of the used amount of the replenishment material I relative to the fermentation medium was 8:100;

Replenishment material II: the carbon/nitrogen ratio was 30:1, the content of the corn steep liquor was 326 ml and the content of the glucose was 680 g relative to 1 L of the second nutrient substance; the volume ratio of the used amount of the replenishment material II relative to the fermentation medium was 5:100;

Replenishment material III: the content of glucose was 900 g relative to 1 L of the third nutrient substance; the volume ratio of the used amount of the replenishment material III relative to the fermentation medium was 20:100.

The seed solution prepared in the Preparation Example was inoculated into a fermentation medium with an inoculation amount of 10 vol %, and the fermentation culture was performed under the conditions consisting of a temperature of 30° C. and a ventilation quantity of 1.5 vvm, the pH in the fermentation process was controlled to be about 7. In addition, the rotation speed was controlled to be about 800 rpm during the fermentation process.

The sugar content and pH of the fermentation system were monitored in real time during the fermentation process.

The replenishment material I was fed in batch when the sugar content in the fermentation system was reduced to below 10 g/L for the first time; the replenishment material II was fed in batch when the feeding of the replenishment material I was finished; the replenishment material III was fed in batch when the feeding of the replenishment material II was finished.

The feeding rate of the replenishment materials in batch caused that the sugar content in the fermentation broth was maintained at about 5 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 2.

Example 2-4

The Example served to explain the method of preparing PHA through fermentation provided by the present disclosure.

The PHA fermentation was performed according to the method of the Comparative Example 2-4, except for that the corn steep liquor was replaced with the enzymolyzed corn steep liquor prepared in the Preparation Example 2.

The comparisons of biomass of *Halomonas* sp. in the fermentation broth, PHA yield and raw material cost per unit product were shown in Table 2.

Comparative Example 2-5

The Comparative Example served to illustrate and compare the method of preparing PHA through fermentation provided by the present disclosure.

Fermentation medium: the content of corn steep liquor (with a solid content of 30 wt %) was 45 mL, the content of glucose was 35 g, the content of dipotassium hydrogen phosphate was 5 g, the content of disodium hydrogen phosphate was 11 g, the content of magnesium sulfate was 0.4 g, and the content of sodium chloride was 70 g, relative to 1 L of the fermentation medium. The pH was adjusted to 9.

Replenishment material: the carbon/nitrogen ratio was 20:1, the content of the corn steep liquor was 516 ml and the content of the glucose was 720 g relative to 1 L of the first nutrient substance; the volume ratio of the used amount of the replenishment material relative to the fermentation medium was 42:100.

The seed solution prepared in the Preparation Example was inoculated into a fermentation medium with an inoculation amount of 10 vol %, and the fermentation culture was performed under the conditions consisting of a temperature of 45° C. and a ventilation quantity of 0.5 vvm, the pH in the fermentation process was controlled to be about 9, and the dissolved oxygen amount was controlled to be within a range of 10-30%. In addition, the rotation speed of stirring was controlled in stages during the fermentation process, wherein the rotation speed of stirring was 400 rpm during the fermentation time period of 0-12 h; the rotation speed of stirring was 800 rpm during the fermentation time period of 12-20 h; the rotation speed of stirring was 400 rpm during the fermentation time period starting from the 20 h to the termination of fermentation process.

The sugar content and pH of the fermentation system were monitored in real time during the fermentation process.

Only the replenishment material I was fed in batch when the sugar content in the fermentation system was reduced to below 12 g/L for the first time.

The feeding rate of the replenishment materials in batch caused that the sugar content in the fermentation broth was maintained at about 20 g/L, and after completing the feeding of the replenishment material III in batch, the fermentation process was continued for 2 hours, then the fermentation process was finished.

The comparisons of biomass of *Halomonas* sp. in the fermentation broth, PHA yield and raw material cost per unit product were shown in Table 2.

Example 2-5

The Example served to explain the method of preparing PHA through fermentation provided by the present disclosure.

The PHA fermentation was performed according to the method of the Comparative Example 2-5, except for that the corn steep liquor was replaced with the enzymolyzed corn steep liquor prepared in the Preparation Example 2.

The comparisons of biomass of *Halomonas* sp. in the fermentation broth, PHA yield and raw material cost per unit product were shown in Table 2.

Comparative Example 2-6

The Example served to illustrate and compare the method of preparing PHA through fermentation provided by the present disclosure.

The PHA was prepared according to the method of Example 2-4, except for that the enzymolyzed corn steep liquor was replaced with an equal amount of urea in terms of the nitrogen element.

The comparisons of biomass of *Halomonas* sp. in the fermentation broth, PHA yield and raw material cost per unit product were shown in Table 2.

Comparative Example 2-7

The Example served to illustrate and compare the method of preparing PHA through fermentation provided by the present disclosure.

The PHA was prepared according to the method of Example 2-4, except for that the enzymolyzed corn steep liquor was replaced with an equal amount of yeast powder in terms of the nitrogen element.

The comparisons of biomass of *Halomonas* sp. in the fermentation broth, PHA yield and raw material cost per unit product were shown in Table 2.

Comparative Example 2-8

The Example served to illustrate and compare the method of preparing PHA through fermentation provided by the present disclosure.

The PHA was prepared according to the method of Example 2-4, except for that the enzymolyzed corn steep liquor was replaced with an equal amount of the enzymolyzed corn steep liquor in the Comparative Preparation Example 2-1 in terms of the nitrogen element.

The comparisons of biomass of *Halomonas* sp. in the fermentation broth, PHA yield and raw material cost per unit product were shown in Table 2.

Comparative Example 2-9

The Example served to illustrate and compare the method of preparing PHA through fermentation provided by the present disclosure.

The PHA was prepared according to the method of Example 2-4, except for that the enzymolyzed corn steep liquor was replaced with an equal amount of the enzymolyzed corn steep liquor in the Comparative Preparation Example 2-2 in terms of the nitrogen element.

The comparisons of biomass of *Halomonas* sp. in the fermentation broth, PHA yield and raw material cost per unit product were shown in Table 2.

Comparative Example 2-10

The Example served to illustrate and compare the method of preparing PHA through fermentation provided by the present disclosure.

The PHA was prepared according to the method of Example 2-4, except for that the enzymolyzed corn steep liquor was replaced with an equal amount of the enzymolyzed corn steep liquor in the Comparative Preparation Example 2-3 in terms of the nitrogen element.

The comparisons of biomass of *Halomonas* sp. in the fermentation broth, PHA yield and raw material cost per unit product were shown in Table 2.

TABLE 2

| Numbers | Biomass (g/L) | PHA yield (g/L) | Fermentation raw material cost change (%) |
|---|---|---|---|
| Comparative Example 2-1 | 94 | 74 | −15 |
| Example 2-1 | 100 | 79 | −12 |
| Comparative Example 2-2 | 95 | 75 | −16 |
| Example 2-2 | 98 | 78 | −17 |
| Comparative Example 2-3 | 97 | 77 | −18 |
| Example 2-3 | 99 | 80 | −19 |
| Comparative Example 2-4 | 92 | 73 | −17 |
| Example 2-4 | 97 | 82 | −19 |
| Comparative Example 2-5 | 89 | 65 | −11 |
| Example 2-5 | 91 | 70 | −13 |
| Comparative Example 2-6 | 89 | 70 | 0 |
| Comparative Example 2-7 | 91 | 72 | +13 |
| Comparative Example 2-8 | 93 | 77 | −18 |
| Comparative Example 2-9 | 93 | 75 | −17 |
| Comparative Example 2-10 | 94 | 81 | −19 |

As can be seen from the results in Table 2, when the Example 2-4 was compared with the Comparative Examples 2-6 and 2-7, the technical solution of the present disclosure can not only effectively reduce the production cost of PHA, but also improve the biomass of the thallus in the fermentation broth and the yield of PHA. As can be seen from comparison of the Examples 2-1 to 2-3 with Examples 2-4 and 2-5, the biomass of the thallus in the fermentation broth and the yield of PHA can be further improved by controlling the fermentation process in the preferred embodiment of the present disclosure. When comparing the Examples 2-1 to 2-6 with the Comparative Examples 2-1 to 2-6, the enzymolyzed corn steep liquor used for PHA fermentation can significantly improve the biomass of thallus in the fermentation broth and the yield of PHA. It can be seen by comparing the Examples 2-4 with the Comparative Examples 2-8 and 2-9 that the enzymolysis method of the present disclosure can increase biomass of the thallus in the fermentation broth and the yield of PHA. Moreover, the color and luster of the fermentation broth may be faded after the enzymolyzed corn steep liquor was subjected to solid-liquid separation.

II. Treatment of PHA Process Wastewater

The disk-type centrifuge was purchased from Nanjing Huasheng Separation Machinery Technology Co., Ltd., the model was DR 203;

The ribbon-type vacuum filter was purchased from Huzhou Nuclear Industry Huineng Environmental Protection Filtration Technology Co., Ltd., and the model was DY-500;

The plate and frame filter was purchased from Haining Yunfei Filter Equipment Co., Ltd., and the model was YF-100-1;

The polyhydroxyalkanoate with a particle size of 1-50 m was purchased from the Langene Biotechnology Co., Ltd., and was used for coating on a filter cloth of a plate and frame filter to form a polyhydroxyalkanoate layer.

As for the methods for measuring recovery rate and purity of PHA, please refer to the reference literature (Engineering Self—flocculating *Halomonas campaniensis* for Wastewaterless Open and Continuous Fermentation [J], *Biotechnology and Bioengineering*, 2019, 116: 805-815);

The biomass of *Halomonas* sp. in the fermentation broth is represented with $OD_{600}$;

Fermentation Strain

*Halomonas* sp. TD01 with the preservation number CGMCC NO. 4353 (CN 201010578858.8).

Seed Culture Medium

It is consisting of 5 g/L of yeast powder, 10 g/L of peptone and 60 g/L of sodium chloride.

Initial Fermentation Medium

It comprises 50 g/L of sodium chloride, 50 g/L of glucose, 15 g/L of corn steep liquor powder, 2 g/L of urea, 0.2 g/L of magnesium sulfate, 5 g/L of monopotassium phosphate, 10 mL/L of microelement mother liquor I and 3 mL/L of microelement mother liquor II. In regard to the microelement mother liquids I and II, please refer to the cited patent CN201010578858.8.

Replenishment Culture Medium

The concentration of glucose is 600 g/L, and the concentration of corn steep liquor is 40 g/L.

Preparation of Fermentation Broth

The Preparation Example served to explain the preparation of a polyhydroxyalkanoate fermentation broth The *Halomonas* sp. was inoculated into a seed culture medium to perform primary activation culture under the conditions consisting of a temperature of 37° C. and 200 rpm until $OD_{600}$ reached about 4, so as to obtain a primary seed solution;

The primary seed solution was inoculated into a seed culture medium with an inoculation amount of 10 vol %, the secondary activation culture was performed under the conditions consisting of a temperature of 37° C. and 200 rpm until $OD_{600}$ reached about 4, so as to obtain a secondary seed solution and a fermented seed solution.

The secondary seed solution was inoculated into an initial fermentation medium with an inoculation amount of 10 vol %, the fermentation system was directly fermented without subjecting to sterilization. The control was performed such that the temperature was 37° C., the rotating speed was within a range of 600-1,000 rpm, the ventilation quantity was 0.5-2.0 vvm, and the initial dissolved oxygen was 30% or more; the sugar concentration during the fermentation process was controlled to be between 5 and 20 g/L through the replenishment material, the fermentation pH was controlled to be 8-9 by using NaOH, and the fermentation was carried out for 48 hours.

Example 3—Adsorption Method for Treatment of PHA Process Wastewater

The adsorbent activated carbon and carbon column, which were commercially available from Jiangsu Zhuxi Activated Carbon Co., Ltd.;

The adsorbent diatomaceous earth was purchased from Jilin Yuantong Mining Co., Ltd.;

The adsorbent bauxite was purchased from Lingshou County Giant Stone Mineral Product Processing Plant.

Example 3-1

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow (for entering an extraction tank) which was rich in fermentation thalli and a fermentation raffinate top flow (with a solid content of 7 wt %), wherein the fermentation raffinate top flow entered into a fermentation raffinate temporary storage tank for further treatment.

(2) the fermentation raffinate top flow obtained in the step (1) was pumped into a high-efficiency precision filter, the residual thalli in the top flow was subjected to another filtering process, the filtered thalli entered the extraction tank in step (1) for further treatment, the filtrate entered into a temporary storage tank for the fermentation residual liquid (with the solid content of 5 wt %) for further treatment.

(3) the fermentation supernatant in the fermentation residual liquid temporary storage tank was pumped into an adsorption separation tank, several carbon columns were added into the adsorption separation tank, wherein the adsorbent was used in an amount of 15 g relative to 1 L of fermentation supernatant. The adsorption was performed under the stirring condition, the adsorption temperature was 20° C., the adsorption time was 40 min, and the rotation speed of stirring was 120 rpm. After the adsorption process, the materials in the adsorption separation tank were pumped into a plate and frame separator (20° C., 0.25 MPa, 2.5 h) while stirring, the solids in the materials were filtered out, the obtained supernatant entered into a storage tank and used as an ingredient for the next fermentation.

(4) the filter cake discharged from the plate and frame separator in the step (3) was fed into a high-temperature regeneration furnace, such that the organic matters adsorbed on the adsorbent was removed by volatilization or decomposition through high-temperature treatment; the partially regenerated adsorbent obtained by removing the organic matters through high-temperature treatment was subjected to cooling down, and subsequently delivered to a washing tank for washing with water and desalting; the material after desalting in the washing tank passed through a plate and frame separator for carrying out a solid-liquid separation, the solid adsorbent obtained through separation was used for next adsorption and separation.

Example 3-2

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow (for entering an extraction tank) which was rich in fermentation thalli and a fermentation raffinate top flow (with a solid content of 10 wt %), wherein the fermentation raffinate top flow entered into a fermentation raffinate temporary storage tank for further treatment.

(2) the fermentation raffinate top flow obtained in the step (1) was pumped into a high-efficiency precision filter, the residual thalli in the top flow was subjected to another filtering process, the filtered thalli entered the extraction tank in step (1) for further treatment, the filtrate entered into a temporary storage tank for the fermentation residual liquid (with the solid content of 8 wt %) for further treatment.

(3) the fermentation supernatant in the fermentation residual liquid temporary storage tank was pumped into an adsorption separation tank, several carbon columns were added into the adsorption separation tank, wherein the adsorbent was used in an amount of 40 g relative to 1 L of fermentation supernatant. The adsorption was performed under the stirring condition, the adsorption temperature was 15° C., the adsorption time was 60 min, and the rotation speed of stirring was 110 rpm. After the adsorption process, the materials in the adsorption separation tank were pumped into a plate and frame separator (15° C., 0.3 MPa, 3 h) while stirring, the solids in the materials were filtered out, the obtained supernatant entered into a storage tank and used as an ingredient for the next fermentation.

(4) the filter cake discharged from the plate and frame separator in the step (3) was fed into a high-temperature regeneration furnace, such that the organic matters adsorbed on the adsorbent was removed by volatilization or decomposition through high-temperature treatment; the partially regenerated adsorbent obtained by removing the organic matters through high-temperature treatment was subjected to cooling down, and subsequently delivered to a washing tank for washing with water and desalting; the material after desalting in the washing tank passed through a plate and frame separator for carrying out a solid-liquid separation, the solid adsorbent obtained through separation was used for next adsorption and separation.

Example 3-3

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow (for entering an extraction tank) which was rich in fermentation thalli and a fermentation raffinate top flow (with a solid content of 15 wt %), wherein the fermentation raffinate top flow entered into a fermentation raffinate temporary storage tank for further treatment.

(2) the fermentation raffinate top flow obtained in the step (1) was pumped into a high-efficiency precision filter, the residual thalli in the top flow was subjected to another filtering process, the filtered thalli entered the extraction tank in step (1) for further treatment, the filtrate entered into a temporary storage tank for the fermentation residual liquid (with the solid content of 10 wt %) for further treatment.

(3) the fermentation supernatant in the fermentation residual liquid temporary storage tank was pumped into an adsorption separation tank, several carbon columns were added into the adsorption separation tank, wherein the adsorbent was used in an amount of 10 g relative to 1 L of fermentation supernatant. The adsorption was performed under the stirring condition, the adsorption temperature was 25° C., the adsorption time was 20 min, and the rotation speed of stirring was 150 rpm. After the adsorption process, the materials in the adsorption separation tank were pumped into a plate and frame separator (25° C., 0.2 MPa, 2 h) while stirring, the solids in the materials were filtered out, the obtained supernatant entered into a storage tank and used as an ingredient for the next fermentation.

(4) the filter cake discharged from the plate and frame separator in the step (3) was fed into a high-temperature regeneration furnace, such that the organic matters adsorbed on the adsorbent was removed by volatilization or decomposition through high-temperature treatment; the partially regenerated adsorbent obtained by removing the organic matters through high-temperature treatment was subjected to cooling down, and subsequently delivered to a washing tank for washing with water and desalting; the material after desalting in the washing tank passed through a plate and frame separator for carrying out a solid-liquid separation, the solid adsorbent obtained through separation was used for next adsorption and separation.

Example 3-4

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow (for entering an extraction tank) which was rich in fermentation thalli and a fermentation raffinate top flow (with a solid content of 15 wt %), wherein the fermentation raffinate top flow entered into a fermentation raffinate temporary storage tank for further treatment.

(2) the fermentation raffinate top flow obtained in the step (1) was pumped into a high-efficiency precision filter, the residual thalli in the top flow was subjected to another filtering process, the filtered thalli entered the extraction tank in step (1) for further treatment, the filtrate entered into a temporary storage tank for the fermentation residual liquid (with the solid content of 10 wt %) for further treatment.

(3) the fermentation supernatant in the fermentation residual liquid temporary storage tank was pumped into an adsorption separation tank, diatomite was added into the adsorption separation tank, wherein the adsorbent was used in an amount of 18 g relative to 1 L of fermentation supernatant. The adsorption was performed under the stirring condition, the adsorption temperature was 40° C., the adsorption time was 10 min, and the rotation speed of stirring was 150 rpm. After the adsorption process, the materials in the adsorption separation tank were pumped into a plate and frame separator (40° C., 0.1 MPa, 1 h) while stirring, the solids in the materials were filtered out, the obtained supernatant entered into a storage tank and used as an ingredient for the next fermentation.

(4) the filter cake discharged from the plate and frame separator in the step (3) was fed into a high-temperature regeneration furnace, such that the organic matters adsorbed on the adsorbent was removed by volatilization or decomposition through high-temperature treatment; the partially regenerated adsorbent obtained by removing the organic matters through high-temperature treatment was subjected to cooling down, and subsequently delivered to a washing tank for washing with water and desalting; the material after desalting in the washing tank passed through a plate and frame separator for carrying out a solid-liquid separation, the solid adsorbent obtained through separation was used for next adsorption and separation.

Example 3-5

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow (for entering an extraction tank) which was rich in fermentation thalli and a fermentation raffinate top flow (with a solid content of 5 wt %), wherein the fermentation raffinate top flow entered into a fermentation raffinate temporary storage tank for further treatment.

(2) the fermentation raffinate top flow obtained in the step (1) was pumped into a high-efficiency precision filter, the residual thalli in the top flow was subjected to another filtering process, the filtered thalli entered the extraction tank in step (1) for further treatment, the filtrate entered into a temporary storage tank for the fermentation residual liquid (with the solid content of 3 wt %) for further treatment.

(3) the fermentation supernatant in the fermentation residual liquid temporary storage tank was pumped into an adsorption separation tank, bauxite was added into the adsorption separation tank, wherein the adsorbent was used in an amount of 60 g relative to 1 L of fermentation supernatant. The adsorption was performed under the stirring condition, the adsorption temperature was 10° C., the adsorption time was 60 min, and the rotation speed of stirring was 50 rpm. After the adsorption process, the materials in the adsorption separation tank were pumped into a plate and frame separator (10° C., 0.5 MPa, 4 h) while stirring, the solids in the materials were filtered out, the obtained supernatant entered into a storage tank and used as an ingredient for the next fermentation.

(4) the filter cake discharged from the plate and frame separator in the step (3) was fed into a high-temperature regeneration furnace, such that the organic matters adsorbed on the adsorbent was removed by volatilization or decomposition through high-temperature treatment; the partially regenerated adsorbent obtained by removing the organic matters through high-temperature treatment was subjected to cooling down, and subsequently delivered to a washing tank for washing with water and desalting; the material after desalting in the washing tank passed through a plate and frame separator for carrying out a solid-liquid separation, the solid adsorbent obtained through separation was used for next adsorption and separation.

Example 3-6

The example served to illustrate the treatment method of a polyhydroxyalkanoate fermentation broth provided by the present disclosure.

The treatment of the polyhydroxyalkanoate fermentation broth was carried out in the same manner as in the Example 3-1, except that the filtration with a plate and frame filter in step (3) was replaced by the filtration with a ribbon-type vacuum filter.

Example 3-7

The example served to illustrate the treatment method of a polyhydroxyalkanoate fermentation broth provided by the present disclosure.

The treatment of the polyhydroxyalkanoate fermentation broth was carried out in the same manner as in the Example 3-1, except that the filtration in step (1) was performed by using a plate and frame filter, and the centrifugal separation in step (2) was performed with a disk-type centrifuge.

Example 3-8

The example served to illustrate the treatment method of a polyhydroxyalkanoate fermentation broth provided by the present disclosure.

The treatment of the polyhydroxyalkanoate fermentation broth was carried out in the same manner as in the Example 3-1, except that the carbon column in step (4) was replaced with an equal amount of mixed adsorbent of activated carbon particles and carbon column, wherein the dosage ratio of the activated carbon particles to the carbon column was 1:1.

Test Examples 3-1 to 3-9

The supernatants separated and obtained in step (3) of Examples 3-1 to 3-8 were respectively used for the preparation of the fermentation medium, and an appropriate inorganic salt was supplemented such that the prepared fermentation medium was the same as the initial fermentation medium, and the initial fermentation medium was used as a control group. The preparation of the fermentation broth of polyhydroxyalkanoates was then carried out according to the same method of "preparation of the fermentation broth", the biomass in the fermentation broth and the effect of PHA fermentation on the reduction of PHA production costs by using the medium with the supernatant of Examples 3-1 to 3-8 as the water relative to the use of the initial fermentation medium were recorded, the results were shown in Table 3.

TABLE 3

| | The corresponding supernatant | Biomass $OD_{600}$ | Cost reduction percentage % |
|---|---|---|---|
| Test Example 3-1 | Example 3-1 | 480 | 29 |
| Test Example 3-2 | Example 3-2 | 460 | 22 |
| Test Example 3-3 | Example 3-3 | 470 | 26 |
| Test Example 3-4 | Example 3-4 | 440 | 18 |
| Test Example 3-5 | Example 3-5 | 400 | 21 |
| Test Example 3-6 | Example 3-6 | 440 | 17 |
| Test Example 3-7 | Example 3-7 | 420 | 16 |
| Test Example 3-8 | Example 3-8 | 500 | 30 |
| Test Example 3-9 | Initial fermentation medium | 500 | — |

As can be seen, the method can significantly reduce the production cost without obviously influencing the PHA fermentation efficiency.

Example 4—Treatment of PHA Process Wastewater with an Oxidation Method hydrogen peroxide with a concentration of 30%, was purchased from Sinopharm Group Chemical Reagent Beijing Co., Ltd.;

hypochlorous acid, was purchased from Sinopharm Group Chemical Reagent Beijing Co., Ltd.;

sodium hypochlorite with a concentration of 10%, was purchased from Sinopharm Group Chemical Reagent Beijing Co., Ltd.

Fermentation Strain

*Halomonas* sp. TD01 with the preservation number of CGMCC NO. 4353 (CN 201010578858.8).

Example 4-1

The example served to illustrate the treatment method of a polyhydroxyalkanoate fermentation broth provided by the present disclosure.

(1) The polyhydroxyalkanoate fermentation broth (fermented for 55 h) prepared in the Preparation Example was subjected to centrifugal separation through a disk-type centrifuge under the separation condition such that the fermentation broth may be divided into a bottom flow which was rich in fermentation thalli (with a water content of 75 wt %) and a fermentation raffinate top flow, wherein the fermentation raffinate top flow entered into a fermentation raffinate temporary storage tank for further treatment.

(2) the bottom flow which was rich in fermentation thalli and obtained in the step (1) was pumped into a ribbon-type vacuum filter, the thalli in the bottom flow were filtered and dried under the condition that the filtered and dried thalli (with the water content of 70 wt %) entered an extraction tank for the further treatment, and the filtrate entered a fermentation raffinate temporary storage tank for the treatment in the next step.

(3) the liquid phase in the fermentation residual liquid temporary storage tank was pumped into a plate and frame filter for performing filtration, wherein the filtering conditions comprised that the pressure was 0.3 MPa, the pore size of filter cloth was 20 μm; the residual thalli and the suspended solids were further separated, the filtered solid phase was fed into an extraction tank and subjected to the next PHA extraction treatment along with the thalli in the step (2), and the liquid phase (fermentation supernatant) was fed into an oxidation decoloration tank to perform an oxidation treatment.

(4) hydrogen peroxide was added into the oxidation treatment separating tank obtained in the step (3), wherein the used amount of the hydrogen peroxide was 18 parts by weight relative to 100 parts by weight of the fermentation supernatant. The oxidation treatment was carried out under the stirring condition, the temperature of the oxidation treatment was 20° C., the time of the oxidation treatment was 120 min, and the rotation speed of stirring was 1,000 rpm. After the completion of the oxidation treatment, an excess amount of solid manganese dioxide was added into the oxidation decoloration tank while stirring, and the treatment was continued under the same conditions as the oxidation treatment, and the generated gas was collected by a gas collecting device. Subsequently, the materials in the oxidation decoloration tank were pumped into a plate and frame separator (20° C., 0.25 MPa, 2.5 h) while stirring, the solid particles in the materials were filtered out, and the obtained supernatant entered a storage tank and used as an ingredient for the next fermentation.

Example 4-2

The example served to illustrate the treatment method of a polyhydroxyalkanoate fermentation broth provided by the present disclosure.

(1) The polyhydroxyalkanoate fermentation broth (fermented for 55 h) prepared in the Preparation Example was subjected to centrifugal separation through a disk-type centrifuge under the separation condition such that the fermentation broth may be divided into a bottom flow which was rich in fermentation thalli (with a water content of 85 wt %) and a fermentation raffinate top flow, wherein the fermentation raffinate top flow entered into a fermentation raffinate temporary storage tank for further treatment.

(2) the bottom flow which was rich in fermentation thalli and obtained in the step (1) was pumped into a ribbon-type vacuum filter, the thalli in the bottom flow were filtered and dried under the condition that the filtered and dried thalli (with the water content of 80 wt %) entered an extraction tank for the further treatment, and the filtrate entered a fermentation raffinate temporary storage tank for the treatment in the next step.

(3) the liquid phase in the fermentation residual liquid temporary storage tank was pumped into a plate and frame filter for performing filtration, wherein the filtering conditions comprised that the pressure was 0.2 MPa, the pore size of filter cloth was 23 μm; the residual thalli and the suspended solids were further separated, the filtered solid phase was fed into an extraction tank and subjected to the next PHA extraction treatment along with the thalli in the step (2), and the liquid phase (fermentation supernatant) was fed into an oxidation decoloration tank to perform an oxidation treatment.

(4) the sodium hypochlorite solution was added into the oxidation treatment separating tank obtained in the step (3), wherein the used amount of the sodium hypochlorite solution was 5 parts by weight relative to 100 parts by weight of the fermentation supernatant. The oxidation treatment was carried out under the stirring condition, the temperature of the oxidation treatment was 25° C., the time of the oxidation treatment was 240 min, and the rotation speed of stirring was 800 rpm. After the completion of the oxidation treatment, an excess amount of dilute hydrochloric acid was added into the oxidation decoloration tank while stirring, and the treatment was continued under the same conditions as the oxidation treatment, and the generated gas was collected by a gas collecting device. Subsequently, the materials in the oxidation decoloration tank were pumped into a plate and frame separator (25° C., 0.3 MPa, 3 h) while stirring, the solid particles in the materials were filtered out, and the obtained supernatant entered a storage tank and used as an ingredient for the next fermentation.

Example 4-3

The example served to illustrate the treatment method of a polyhydroxyalkanoate fermentation broth provided by the present disclosure.

(1) The polyhydroxyalkanoate fermentation broth (fermented for 55 h) prepared in the Preparation Example was subjected to centrifugal separation through a disk-type centrifuge under the separation condition such that the fermentation broth may be divided into a bottom flow which was rich in fermentation thalli (with a water content of 70 wt %)

and a fermentation raffinate top flow, wherein the fermentation raffinate top flow entered into a fermentation raffinate temporary storage tank for further treatment.

(2) the bottom flow which was rich in fermentation thalli and obtained in the step (1) was pumped into a ribbon-type vacuum filter, the thalli in the bottom flow were filtered and dried under the condition that the filtered and dried thalli (with the water content of 60 wt %) entered an extraction tank for the further treatment, and the filtrate entered a fermentation raffinate temporary storage tank for the treatment in the next step.

(3) the liquid phase in the fermentation residual liquid temporary storage tank was pumped into a plate and frame filter for performing filtration, wherein the filtering conditions comprised that the pressure was 0.6 MPa, the pore size of filter cloth was 13 μm; the residual thalli and the suspended solids were further separated, the filtered solid phase was fed into an extraction tank and subjected to the next PHA extraction treatment along with the thalli in the step (2), and the liquid phase (fermentation supernatant) was fed into an oxidation decoloration tank to perform an oxidation treatment.

(4) the sodium hypochlorite solution was added into the oxidation treatment separating tank obtained in the step (3), wherein the used amount of the sodium hypochlorite solution was 10 parts by weight relative to 100 parts by weight of the fermentation supernatant. The oxidation treatment was carried out under the stirring condition, the temperature of the oxidation treatment was 30° C., the time of the oxidation treatment was 180 min, and the rotation speed of stirring was 1,200 rpm. After the completion of the oxidation treatment, an excess amount of dilute hydrochloric acid was added into the oxidation decoloration tank while stirring, and the treatment was continued under the same conditions as the oxidation treatment, and the generated gas was collected by a gas collecting device. Subsequently, the materials in the oxidation decoloration tank were pumped into a plate and frame separator (15° C., 0.2 MPa, 2 h) while stirring, the solid particles in the materials were filtered out, and the obtained supernatant entered a storage tank and used as an ingredient for the next fermentation.

Example 4-4

The example served to illustrate the treatment method of a polyhydroxyalkanoate fermentation broth provided by the present disclosure.

The steps (1)-(3) were identical with those in the Example 4-3.

(4) hydrogen peroxide was added into the oxidation treatment separating tank obtained in the step (3), wherein the used amount of the hydrogen peroxide was 4 parts by weight relative to 100 parts by weight of the fermentation supernatant. The oxidation treatment was carried out under the stirring condition, the temperature of the oxidation treatment was 40° C., the time of the oxidation treatment was 80 min, and the rotation speed of stirring was 1,500 rpm. After the completion of the oxidation treatment, an excess amount of solid manganese dioxide was added into the oxidation decoloration tank while stirring, and the treatment was continued under the same conditions as the oxidation treatment, and the generated gas was collected by a gas collecting device. Subsequently, the materials in the oxidation decoloration tank were pumped into a plate and frame separator (40° C., 0.1 MPa, 1 h) while stirring, the solid particles in the materials were filtered out, and the obtained supernatant entered a storage tank and used as an ingredient for the next fermentation.

Example 4-5

The example served to illustrate the treatment method of a polyhydroxyalkanoate fermentation broth provided by the present disclosure.

The steps (1)-(3) were identical with those in the Example 4-3.

(4) the hypochlorous acid solution was added into the oxidation treatment separating tank obtained in the step (3), wherein the used amount of the hypochlorous acid solution was 25 parts by weight relative to 100 parts by weight of the fermentation supernatant in terms of the active ingredient. The oxidation treatment was carried out under the stirring condition, the temperature of the oxidation treatment was 15° C., the time of the oxidation treatment was 300 min, and the rotation speed of stirring was 500 rpm. After the completion of the oxidation treatment, an excess amount of solid manganese dioxide was added into the oxidation decoloration tank while stirring, and the treatment was continued under the same conditions as the oxidation treatment, and the generated gas was collected by a gas collecting device. Subsequently, the materials in the oxidation decoloration tank were pumped into a plate and frame separator (10° C., 0.5 MPa, 4 h) while stirring, the solid particles in the materials were filtered out, and the obtained supernatant entered a storage tank and used as an ingredient for the next fermentation.

Example 4-6

The example served to illustrate the treatment method of a polyhydroxyalkanoate fermentation broth provided by the present disclosure.

The treatment of the polyhydroxyalkanoate fermentation broth was carried out in the same manner as in the Example 4-1, except that the filtration with the plate and frame filter in step (4) was replaced with the filtration with a ribbon-type vacuum filter.

Example 4-7

The example served to illustrate the treatment method of a polyhydroxyalkanoate fermentation broth provided by the present disclosure.

The polyhydroxyalkanoate fermentation broth was treated in the same manner as in Example 4-1, except that the filtration in step (1) was performed using a plate and frame filter, the centrifugal separation in step (2) was performed with a disk-type centrifuge, and the filtration in step (3) was performed by using a ribbon-type vacuum filter.

Test Examples 4-1 to 4-8

The supernatants separated and obtained in step (4) of Examples 4-1 to 4-7 were respectively used for the preparation of the fermentation medium, and an appropriate inorganic salt was supplemented such that the prepared fermentation medium was the same as the initial fermentation medium, and the initial fermentation medium was used as a control group. The preparation of the fermentation broth of polyhydroxyalkanoates was then carried out according to the same method of the Preparation Example, the biomass in the fermentation broth, the recovery rate of PHA, and the effect of PHA fermentation on the reduction of PHA production costs by using the medium with the supernatant of Examples 4-1 to 4-7 as the water relative to the use of the initial fermentation medium were recorded, the results were shown in Table 4.

|  | The corresponding supernatant | Biomass $OD_{600}$ | Cost reduction percentage % |
| --- | --- | --- | --- |
| Test Example 4-1 | Example 4-1 | 480 | 30 |
| Test Example 4-2 | Example 4-2 | 465 | 29 |
| Test Example 4-3 | Example 4-3 | 450 | 25 |
| Test Example 4-4 | Example 4-4 | 440 | 23 |
| Test Example 4-5 | Example 4-5 | 423 | 20 |
| Test Example 4-6 | Example 4-6 | 380 | 15 |
| Test Example 4-7 | Example 4-7 | 405 | 18 |
| Test Example 4-8 | Initial fermentation medium | 500 | — |

As can be seen, the method can significantly reduce the production cost without obviously influencing the PHA fermentation efficiency.

Example 5—Membrane Separation Method for Treating PHA Process Wastewater

The polyhydroxyalkanoate with a particle size of 20-200 m was purchased from Langene Biotechnology Co., Ltd., and was used for coating on a filter cloth of a plate and frame filter to form a polyhydroxyalkanoate layer.

As for the methods for measuring recovery rate and purity of PHA, please refer to the reference literature (Engineering Self—flocculating *Halomonas campaniensis* for Wastewaterless Open and Continuous Fermentation [J], *Biotechnology and Bioengineering*, 2019, 116: 805-815);

The ceramic membranes were purchased from Jiangsu JiuWu Hi-Tech Co., Ltd.;

The ultrafiltration membrane was purchased from Shanghai Sai-ao Separation Technology Engineering Co., Ltd.

Example 5-1

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow which was rich in fermentation thalli and a fermentation raffinate top flow (with a solid content of 7 wt %), the fermentation raffinate top flow entered into a fermentation raffinate temporary storage tank for further treatment, the bottom flow which was rich in fermentation thalli entered into an extraction tank for PHA extraction.

(2) the liquid phase in the fermentation residual liquid temporary storage tank was pumped into a plate and frame filter for performing filtration, the residual thalli and suspended solids were further separated, the filtered solid phase was fed into an extraction tank and subjected to the PHA extraction and treatment in the next step along with the thalli in the step (1), the liquid phase (i.e., the fermentation supernatant with a solid content of 5 wt %) was subjected to the subsequent membrane separation.

(3) the liquid phase obtained in the step (2) was filtered with a ceramic membrane, wherein the filtering conditions comprised that the pressure was 0.2 MPa, and the pore size of said membrane was 50 nm; the filtrate obtained after the ceramic membrane filtration was subsequently filtered by using an ultrafiltration membrane, wherein the filtering conditions included that the pressure was 0.3 MPa, and the cutoff weight average molecular weight was 5,000 Da. Thus the treated fermentation supernatant was obtained, the treated fermentation supernatant was fed into a storage tank and used as an ingredient for the next fermentation.

Example 5-2

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow which was rich in fermentation thalli and a fermentation raffinate top flow (with a solid content of 10 wt %), the fermentation raffinate top flow entered into a fermentation raffinate temporary storage tank for further treatment, the bottom flow which was rich in fermentation thalli entered into an extraction tank for PHA extraction.

(2) the liquid phase in the fermentation residual liquid temporary storage tank was pumped into a plate and frame filter for performing filtration, the residual thalli and suspended solids were further separated, the filtered solid phase was fed into an extraction tank and subjected to the PHA extraction and treatment in the next step along with the thalli in the step (1), the liquid phase (i.e., the fermentation supernatant with a solid content of 8 wt %) was subjected to the subsequent membrane separation.

(3) the liquid phase obtained in the step (2) was filtered with a ceramic membrane, wherein the filtering conditions comprised that the pressure was 0.3 MPa and the pore size was 20 nm; the filtrate obtained after the ceramic membrane filtration was subsequently filtered by using an ultrafiltration membrane, wherein the filtering conditions included that the pressure was 0.6 MPa, and the cutoff weight average molecular weight was 1,000 Da. Thus the treated fermentation supernatant was obtained, the treated fermentation supernatant was fed into a storage tank and used as an ingredient for the next fermentation.

Example 5-3

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow which was rich in fermentation thalli and a fermentation raffinate top flow (with a solid content of 15 wt %), the fermentation raffinate top flow entered into a fermentation raffinate temporary storage tank for further treatment, the bottom flow which was rich in fermentation thalli entered into an extraction tank for PHA extraction.

(2) the liquid phase in the fermentation residual liquid temporary storage tank was pumped into a plate and frame filter for performing filtration, the residual thalli and suspended solids were further separated, the filtered solid phase was fed into an extraction tank and subjected to the PHA extraction and treatment in the next step along with the thalli in the step (1), the liquid phase (i.e., the fermentation supernatant with a solid content of 10 wt %) was subjected to the subsequent membrane separation.

(3) the liquid phase obtained in the step (2) was filtered with a ceramic membrane, wherein the filtering conditions comprised that the pressure was 0.4 MPa and the pore size was 30 nm; the filtrate obtained after the ceramic membrane filtration was subsequently filtered by using an ultrafiltration membrane, wherein the filtering conditions included that the pressure was 0.4 MPa, and the cutoff weight average molecular weight was 3,000 Da. Thus the treated fermentation supernatant was obtained, the treated fermentation supernatant was fed into a storage tank and used as an ingredient for the next fermentation.

Example 5-4

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow which was rich in fermentation thalli and a fermentation raffinate top flow (with a solid content of 15 wt %), the fermentation raffinate top flow entered into a fermentation raffinate temporary storage tank for further treatment, the bottom flow which was rich in fermentation thalli entered into an extraction tank for PHA extraction.

(2) the liquid phase in the fermentation residual liquid temporary storage tank was pumped into a plate and frame filter for performing filtration, the residual thalli and suspended solids were further separated, the filtered solid phase was fed into an extraction tank and subjected to the PHA extraction and treatment in the next step along with the thalli in the step (1), the liquid phase (i.e., the fermentation supernatant with a solid content of 10 wt %) was subjected to the subsequent membrane separation.

(3) the liquid phase obtained in the step (2) was filtered with a ceramic membrane, wherein the filtering conditions comprised that the pressure was 0.1 MPa and the pore size was 10 nm; the filtrate obtained after the ceramic membrane filtration was subsequently filtered by using an ultrafiltration membrane, wherein the filtering conditions included that the pressure was 0.9 MPa, and the cutoff weight average molecular weight was 800 Da. Thus the treated fermentation supernatant was obtained, the treated fermentation supernatant was fed into a storage tank and used as an ingredient for the next fermentation.

Example 5-5

The example served to illustrate the treatment method of a polyhydroxyalkanoate fermentation broth provided by the present disclosure.

(1) The polyhydroxyalkanoate fermentation broth prepared in the Preparation Example was subjected to centrifugal separation through a disk-type centrifuge, and the fermentation broth may be divided into a bottom flow which was rich in fermentation thalli and a fermentation raffinate top flow (with a solid content of 5 wt %), the fermentation raffinate top flow entered into a fermentation raffinate temporary storage tank for further treatment, the bottom flow which was rich in fermentation thalli entered into an extraction tank for PHA extraction.

(2) the liquid phase in the fermentation residual liquid temporary storage tank was pumped into a plate and frame filter for performing filtration, the residual thalli and suspended solids were further separated, the filtered solid phase was fed into an extraction tank and subjected to the PHA extraction and treatment in the next step along with the thalli in the step (1), the liquid phase (i.e., the fermentation supernatant with a solid content of 3 wt %) was subjected to the subsequent membrane separation.

(3) the liquid phase obtained in the step (2) was filtered with a ceramic membrane, wherein the filtering conditions comprised that the pressure was 0.5 MPa and the pore size was 60 nm; the filtrate obtained after the ceramic membrane filtration was subsequently filtered by using an ultrafiltration membrane, wherein the filtering conditions included that the pressure was 0.2 MPa, and the cutoff weight average molecular weight was 6,000 Da. Thus the treated fermentation supernatant was obtained, the treated fermentation supernatant was fed into a storage tank and used as an ingredient for the next fermentation.

Example 5-6

The example served to illustrate the treatment method of a polyhydroxyalkanoate fermentation broth provided by the present disclosure.

The treatment of the polyhydroxyalkanoate fermentation broth was performed according to the method in the Example 5-1, except that the ceramic membrane was replaced with a spirally wound membrane.

Example 5-7

The example served to illustrate the treatment method of a polyhydroxyalkanoate fermentation broth provided by the present disclosure.

The polyhydroxyalkanoate fermentation broth was treated according to the method in the Example 5-1, except that the filtration in step (1) was performed by using a plate and frame filter, and the centrifugation in step (2) was performed with a disk-type centrifuge.

Example 5-8

The example served to illustrate the treatment method of a polyhydroxyalkanoate fermentation broth provided by the present disclosure.

The treatment of the polyhydroxyalkanoate fermentation broth was performed according to the method in the Example 5-1, except that the separation in step (2) was carried out by using a ribbon-type vacuum filter.

Test Examples 5-1 to 5-9

The supernatants separated and obtained in step (3) of Examples 5-1 to 5-8 were respectively used for the preparation of the fermentation medium, and an appropriate inorganic salt was supplemented such that the prepared fermentation medium was the same as the initial fermentation medium, and the initial fermentation medium was used as a control group. The preparation of the fermentation broth of polyhydroxyalkanoates was then carried out according to the same method of "preparation of the fermentation broth", the biomass in the fermentation broth and the effect of PHA fermentation on the reduction of PHA production costs by using the medium with the supernatant of Examples 5-1 to 5-8 as the water relative to the use of the initial fermentation medium were recorded, the results were shown in Table 5.

TABLE 5

| | The corresponding supernatant | Biomass $OD_{600}$ | Cost reduction percentage % |
|---|---|---|---|
| Test Example 5-1 | Example5-1 | 470 | 20 |
| Test Example 5-2 | Example5-2 | 500 | 25 |
| Test Example 5-3 | Example5-3 | 480 | 23 |
| Test Example 5-4 | Example5-4 | 435 | 18 |
| Test Example 5-5 | Example5-5 | 390 | 20 |
| Test Example 5-6 | Example5-6 | 410 | 15 |
| Test Example 5-7 | Example5-7 | 400 | 21 |
| Test Example 5-8 | Example5-8 | 395 | 20 |
| Test Example 5-9 | Initial fermentation medium | 500 | — |

As can be seen, the method can significantly reduce the production cost without obviously influencing the PHA fermentation efficiency.

Example 6—Chromatographic Method for Treatment of PHA Process Wastewater

Ion exchange resins respectively with the model numbers LSA-700 and LSA-700B were purchased from the Xi'an Sunresin Technology New Materials Stock Co., Ltd.

The ion exchange resins with a model number DA201B were purchased from the Jiangsu Suqing Water Treatment Engineering Group Co., Ltd.;

The ion exchange resins with a model number D201 was purchased from the Langfang Nanda Resin Co., Ltd.

Example 6-1

The example served to illustrate the treatment of a polyhydroxyalkanoate fermentation broth provided by the present disclosure.

(1) The polyhydroxyalkanoate fermentation broth prepared in the Preparation Example was subjected to centrifugal separation through a disk-type centrifuge under the separation condition such that the fermentation broth may be divided into a bottom flow which was rich in fermentation thalli (with a water content of 75 wt %) and a fermentation raffinate top flow, wherein the fermentation raffinate top flow entered into a fermentation raffinate temporary storage tank for further treatment.

(2) The bottom flow which was rich in fermentation thalli and obtained in the step (1) was pumped into a ribbon-type vacuum filter, the thalli in the bottom flow were filtered and dried under the condition that the filtered and dried thalli (with the water content of 70 wt %) entered an extraction tank for the further treatment, and the filtrate entered a fermentation raffinate temporary storage tank for the treatment in the next step.

(3) The liquid phase in the fermentation residual liquid temporary storage tank was pumped into a plate and frame filter for performing filtration, wherein the filtering conditions comprised that the pressure was 0.3 MPa, the filter cloth was 1,000 meshes; the residual thalli and the suspended solids were further separated, the filtered solid phase was fed into an extraction tank and subjected to the next PHA extraction treatment along with the thalli in the step (2), and the liquid phase (i.e., fermentation supernatant) was fed into a chromatographic adsorption column for performing adsorption treatment.

(4) The fermentation supernatant obtained in the step (3) was introduced into the anion exchange adsorption resin D201 at an introduction speed of 2 BV/h and the adsorption temperature of 20° C. The effluent liquid was collected and fed into a storage tank and used as an ingredient for the next fermentation.

(5) The chromatographic column was subjected to a regeneration process.

Example 6-2

The example served to illustrate the treatment of a polyhydroxyalkanoate fermentation broth provided by the present disclosure.

(1) The polyhydroxyalkanoate fermentation broth prepared in the Preparation Example was subjected to centrifugal separation through a disk-type centrifuge under the separation condition such that the fermentation broth may be divided into a bottom flow which was rich in fermentation thalli (with a water content of 85 wt %) and a fermentation raffinate top flow, wherein the fermentation raffinate top flow entered into a fermentation raffinate temporary storage tank for further treatment.

(2) The bottom flow which was rich in fermentation thalli and obtained in the step (1) was pumped into a ribbon-type vacuum filter, the thalli in the bottom flow were filtered and dried under the condition that the filtered and dried thalli (with the water content of 80 wt %) entered an extraction tank for the further treatment, and the filtrate entered a fermentation raffinate temporary storage tank for the treatment in the next step.

(3) The liquid phase in the fermentation residual liquid temporary storage tank was pumped into a plate and frame filter for performing filtration, wherein the filtering conditions comprised that the pressure was 0.2 MPa, the filter cloth was 800 meshes; the residual thalli and the suspended solids were further separated, the filtered solid phase was fed into an extraction tank and subjected to the next PHA extraction treatment along with the thalli in the step (2), and the liquid phase (i.e., fermentation supernatant) was fed into a chromatographic adsorption column for performing adsorption treatment.

(4) The fermentation supernatant obtained in the step (3) was introduced into the anion exchange adsorption resin D201 at an introduction speed of 1.5 BV/h and the adsorption temperature of 15° C. The effluent liquid was collected and fed into a storage tank and used as an ingredient for the next fermentation.

(5) The chromatographic column was subjected to a regeneration process.

Example 6-3

The example served to illustrate the treatment of a polyhydroxyalkanoate fermentation broth provided by the present disclosure.

(1) The polyhydroxyalkanoate fermentation broth prepared in the Preparation Example was subjected to centrifugal separation through a disk-type centrifuge under the separation condition such that the fermentation broth may be divided into a bottom flow which was rich in fermentation thalli (with a water content of 70 wt %) and a fermentation raffinate top flow, wherein the fermentation raffinate top flow entered into a fermentation raffinate temporary storage tank for further treatment.

(2) The bottom flow which was rich in fermentation thalli and obtained in the step (1) was pumped into a ribbon-type vacuum filter, the thalli in the bottom flow were filtered and dried under the condition that the filtered and dried thalli (with the water content of 60 wt %) entered an extraction tank for the further treatment, and the filtrate entered a fermentation raffinate temporary storage tank for the treatment in the next step.

(3) The liquid phase in the fermentation residual liquid temporary storage tank was pumped into a plate and frame filter for performing filtration, wherein the filtering conditions comprised that the pressure was 0.6 MPa, the filter cloth was 900 meshes; the residual thalli and the suspended solids were further separated, the filtered solid phase was fed into an extraction tank and subjected to the next PHA extraction treatment along with the thalli in the step (2), and the liquid phase (i.e., fermentation supernatant) was fed into a chromatographic adsorption column for performing adsorption treatment.

(4) The fermentation supernatant obtained in the step (3) was introduced into the anion exchange adsorption resin D201 at an introduction speed of 2.5 BV/h and the adsorption temperature of 25° C. The effluent liquid was collected and fed into a storage tank and used as an ingredient for the next fermentation.

(5) The chromatographic column was subjected to a regeneration process.

Example 6-4

The example served to illustrate the treatment of a polyhydroxyalkanoate fermentation broth provided by the present disclosure.

The steps (1)-(3) were identical with those in the Example 6-3.

(4) The fermentation supernatant obtained in the step (3) was introduced into the anion exchange adsorption resin LSA-700 at an introduction speed of 1 BV/h and the adsorption temperature of 40° C. The effluent liquid was collected and fed into a storage tank and used as an ingredient for the next fermentation.

(5) The chromatographic column was subjected to a regeneration process.

Example 6-5

The example served to illustrate the treatment of a polyhydroxyalkanoate fermentation broth provided by the present disclosure.

The steps (1)-(3) were identical with those in the Example 6-3.

(4) The fermentation supernatant obtained in the step (3) was introduced into the anion exchange adsorption resin LSA-700B at an introduction speed of 3 BV/h and the adsorption temperature of 40° C. The effluent liquid was collected and fed into a storage tank and used as an ingredient for the next fermentation.

(5) The chromatographic column was subjected to a regeneration process.

Example 6-6

The example served to illustrate the treatment of a polyhydroxyalkanoate fermentation broth provided by the present disclosure.

The treatment of the polyhydroxyalkanoate fermentation broth was carried out according to the method in the Example 6-1, except that the resin in use was an AB-8 resin, and filtration with a plate and frame filter in step (4) was replaced by the filtration performed by using a ribbon-type vacuum filter.

Example 6-7

The example served to illustrate the treatment of a polyhydroxyalkanoate fermentation broth provided by the present disclosure.

The polyhydroxyalkanoate fermentation broth was treated according to the method in the Example 6-1, except that the filtration in step (1) was performed by using a plate and frame filter, the centrifugal separation in step (2) was performed with a disk-type centrifuge, and the filtration in step (3) was performed by using a ribbon-type vacuum filter.

Test Examples 6-1 to 6-8

The supernatants separated and obtained in step (4) of Examples 6-1 to 6-7 were respectively used for the preparation of the fermentation medium, and an appropriate inorganic salt was supplemented such that the prepared fermentation medium was the same as the initial fermentation medium, and the initial fermentation medium was used as a control group. The preparation of the fermentation broth of polyhydroxyalkanoates was then carried out according to the same method of the Preparation Example, the biomass in the fermentation broth, the recovery rate of PHA, and the effect of PHA fermentation on the reduction of PHA production costs by using the medium with the supernatant of Example 1-8 as the water relative to the use of the initial fermentation medium were recorded, the results were shown in Table 6.

TABLE 6

| | The corresponding supernatant | Biomass $OD_{600}$ | Cost reduction percentage % |
|---|---|---|---|
| Test Example 6-1 | Example 6-1 | 464 | 26 |
| Test Example 6-2 | Example 6-2 | 453 | 23 |
| Test Example 6-3 | Example 6-3 | 460 | 26 |
| Test Example 6-4 | Example 6-4 | 380 | 15 |
| Test Example 6-5 | Example 6-5 | 395 | 18 |
| Test Example 6-6 | Example 6-6 | 397 | 18 |
| Test Example 6-7 | Example 6-7 | 420 | 21 |
| Test Example 6-8 | Initial fermentation medium | 500 | — |

As can be seen, the method can significantly reduce the production cost without obviously influencing the PHA fermentation efficiency.

III. The Influence of the PHA Extraction Process on the PHA Recovery Rate and Purity The disk-type centrifuge was purchased from Nanjing Huasheng Separation Machinery Technology Co., Ltd., the model was DR 203;

The ribbon-type vacuum filter was purchased from Huzhou Nuclear Industry Huineng Environmental Protection Filtration Technology Co., Ltd., and the model was DY-500;

The plate and frame filter was purchased from Haining Yunfei Filter Equipment Co., Ltd., and the model was YF-100-1;

The surfactant sodium dodecyl sulfate (SDS) was purchased from the Yeyuan Biotechnology Co., Ltd., the product number was S15013;

The polyhydroxyalkanoate with a particle size of 1-200 m was purchased from Langene Biotechnology Co., Ltd., and was used for coating on a filter cloth of a plate and frame filter to form a polyhydroxyalkanoate layer;

As for the methods for measuring recovery rate and purity of PHA, please refer to the reference literature (Engineering self—flocculating *Halomonas campaniensis* for wastewaterless open and continuous fermentation).

Preparation Example

The preparation example served to illustrate the preparation of a fermentation broth of polyhydroxyalkanoate.

The *Halomonas* sp. (TD 01, the preservation number was CGMCC NO. 4353 according to the patent document CN201010578858.8) was inoculated into a seed culture medium (comprising 5 g/L of yeast powder, 10 g/L of peptone and 60 g/L of sodium chloride) to perform primary activation culture under the conditions consisting of a temperature of 37° C. and 200 rpm until $OD_{600}$ reached about 4, so as to obtain a primary seed solution;

The primary seed solution was inoculated into a seed culture medium with an inoculation amount of 10 vol %, the secondary activation culture was performed under the conditions consisting of a temperature of 37° C. and 200 rpm until $OD_{600}$ reached about 4, so as to obtain a secondary seed solution;

The secondary seed solution was subsequently inoculated into an initial fermentation medium (comprising 50 g/L of sodium chloride, 50 g/L of glucose, 15 g/L of corn steep liquor powder, 2 g/L of urea, 0.2 g/L of magnesium sulfate, 5 g/L of potassium dihydrogen phosphate, 10 mL/L of microelement mother liquid I, 3 mL/L of microelement mother liquid II, the microelement mother liquids I and II were referred in the cited patent CN201010578858.8) according to the inoculation amount of 10 vol %, the fermentation system was directly fermented without subjecting to sterilization. The control was performed such that the temperature was 37° C., the rotating speed was within a range of 600-1,000 rpm, the ventilation quantity was 0.5-2.0 vvm, and the initial dissolved oxygen was 30% or more; the sugar concentration during the fermentation process was controlled to be between 5 and 20 g/L through the replenishment material, the fermentation pH was controlled to be 8-9 by using NaOH, and the fermentation was carried out for 48 hours.

Example 7-Coating the Filter Cloth with PHA

Lysozyme CAS: 12650-88-3, which was purchased from Beijing Oriental Rada Biotech Co., Ltd.;

Example 7-1

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 6,000 rpm and a feed rate of 60 L/min; the fermentation broth was divided into a bottom flow which was rich in fermentation thalli (with a water content of 75 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.3 MPa and the treatment capacity was 20 kg/min, the filtered and dried thalli (with the water content of 70 wt %) entered an extraction tank for the further treatment.

(3) The thalli in the extraction tank were washed with water for 3 times, and then centrifuged to remove impurities thereof.

(4) An acid-base regulator was added into the extraction tank in the step (3) to adjust the pH value to 9, the stirring and stewing process was performed for 2 hours at the temperature of 120° C., the pressure of 0.15 MPa and the rotating speed of 100 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 25° C., the pressure was 0.7 MPa, and the time was 5 hours. The solid particles of PHA were separated. The filter cloth of the plate and frame filter was coated with a polyhydroxyalkanoate layer with a thickness of 8 mm, and the filter cloth coated with the polyhydroxyalkanoate layer had a pore size of 2 μm.

(7) The solid PHA separated by the plate and frame filter in step (6) was subjected to the spray drying to obtain PHA dry powder, the recovery rate and purity were shown in Table 7.

Example 7-2

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 5,500 rpm and a feed rate of 55 L/min; the fermentation broth was divided into a bottom flow which was rich in fermentation thalli (with a water content of 85 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.35 MPa and the treatment capacity was 23 kg/min, the filtered and dried thalli (with the water content of 80 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 8, the stirring and stewing process was performed for 2.5 hours at the temperature of 90° C., the pressure of 0.1 MPa and the rotating speed of 120 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 30° C., the pressure was 0.6 MPa, and the time was 4 hours. The solid particles of PHA were separated. The filter cloth of the plate and frame filter was coated with a polyhydroxyalkanoate layer with a thickness of 10 mm, and the filter cloth coated with the polyhydroxyalkanoate layer had a pore size of 5 μm.

(7) The solid PHA separated by the plate and frame filter in step (6) was subjected to the spray drying to obtain PHA dry powder, the recovery rate and purity were shown in Table 7.

Example 7-3

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 5,000 rpm and a feed rate of 50 L/min; the fermentation broth was divided into a bottom flow which was rich in fermentation thalli (with a water content of 70 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.4 MPa and the treatment capacity was 25 kg/min, the filtered and dried thalli (with the water content of 60 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 7, the stirring and stewing process was performed for 1 hours at the temperature of 130° C., the pressure of 0.2 MPa and the rotating speed of 80 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 35° C., the pressure was 0.65 MPa, and the time was 3 hours. The solid particles of PHA were separated. The filter cloth of the plate and frame filter was coated with a polyhydroxyalkanoate layer with a thickness of 12 mm, and the filter cloth coated with the polyhydroxyalkanoate layer had a pore size of 10 μm.

(7) The solid PHA separated by the plate and frame filter in step (6) was subjected to the spray drying to obtain PHA dry powder, the recovery rate and purity were shown in Table 7.

Example 7-4

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 4,000 rpm and a feed rate of 50 L/min; the fermentation broth was divided into a bottom flow which was rich in fermentation thalli (with a water content of 90 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.5 MPa and the treatment capacity was 20 kg/min, the filtered and dried thalli (with the water content of 65 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 6, the stirring and stewing process was performed for 4 hours at the temperature of 50° C., the pressure of 0.1 MPa and the rotating speed of 250 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 40° C., the pressure was 0.8 MPa, and the time was 2 hours. The solid particles of PHA were separated. The filter cloth of the plate and frame filter was coated with a polyhydroxyalkanoate layer with a thickness of 14 mm, and the filter cloth coated with the polyhydroxyalkanoate layer had a pore size of 1 μm.

(7) The solid PHA separated by the plate and frame filter in step (6) was subjected to the spray drying to obtain PHA dry powder, the recovery rate and purity were shown in Table 7.

Example 7-5

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 7,000 rpm and a feed rate of 50 L/min; the fermentation broth was divided into a bottom flow which was rich in fermentation thalli (with a water content of 60 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.5 MPa and the treatment capacity was 20 kg/min, the filtered and dried thalli (with the water content of 50 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 10, the stirring and stewing process was performed for 0.5 hour at the temperature of 200° C., the pressure of 0.3 MPa and the rotating speed of 120 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 15° C., the pressure was 0.2 MPa, and the time was 8 hours. The solid particles of PHA were separated. The filter cloth of the plate and frame filter was coated with a polyhydroxyalkanoate layer with a thickness of 20 mm, and the filter cloth coated with the polyhydroxyalkanoate layer had a pore size of 20 μm.

(7) The solid PHA separated by the plate and frame filter in step (6) was subjected to the spray drying to obtain PHA dry powder, the recovery rate and purity were shown in Table 7.

Example 7-6

The example served to illustrate the separation method of polyhydroxyalkanoate provided by the present disclosure.

The separation of polyhydroxyalkanoate was performed in accordance with the method of the Example 7-2, except that the ribbon-type vacuum filter in step (2) was replaced with a disk-type centrifuge, and the separation was performed in accordance with the conditions of step (1). The recovery rate and purity were shown in Table 7.

Example 7-7

The example served to illustrate the separation method of polyhydroxyalkanoate provided by the present disclosure.

The separation of polyhydroxyalkanoate was performed in accordance with the method of the Example 7-2, except that the sufficient amount of dodecylsulfonic acid was added in step (4) to maintain at room temperature and a pressure of 0.1 MPa for 4 hours, that is, the heating and pressurizing treatment was not performed. The recovery rate and purity were shown in Table 7.

Example 7-8

The example served to illustrate the separation method of polyhydroxyalkanoate provided by the present disclosure.

The separation of polyhydroxyalkanoate was performed according to the method of the Example 7-2, except that, the polyhydroxyalkanoate used for coating the polyhydroxyalkanoate layer in step (6) was the polyhydroxyalkanoate separated from the product after breaking the cell walls. The recovery and purity were shown in Table 7.

Comparative Example 7-1

The Comparative Example served to illustrate and compare the separation method of polyhydroxyalkanoate provided by the present disclosure.

The separation of polyhydroxyalkanoate was performed according to the method in the Example 7-1, except that the filter cloth used in step (6) was not coated with a polyhydroxyalkanoate layer. The recovery rate and purity were shown in Table 7.

Comparative Example 7-2

The Comparative Example served to illustrate and compare the separation method of polyhydroxyalkanoate provided by the present disclosure.

The separation of polyhydroxyalkanoate was performed according to the method in the Example 7-1, except that the filter cloth in step (6) was coated with a layer of diatomaceous earth.

The recovery rate and purity were shown in Table 7.

Comparative Example 7-3

The Comparative Example served to illustrate and compare the separation method of polyhydroxyalkanoate provided by the present disclosure.

The extraction of PHA from the prepared fermentation broth was performed according to the method disclosed in the literature Engineering self—flocculating *Halomonas campaniensis* for wastewaterless open and continuous fermentation, *Biotechnology and Bioengineering* [J]. 2019; 116:805-815. The recovery rate and purity were shown in Table 7.

TABLE 7

| Example Numbers | Recovery rate (%) | Purity (%) |
| --- | --- | --- |
| Example 7-1 | 86 | 94 |
| Example 7-2 | 85 | 93 |
| Example 7-3 | 84 | 92 |
| Example 7-4 | 80 | 91 |
| Example 7-5 | 82 | 90 |
| Example 7-6 | 85 | 92 |
| Example 7-7 | 81 | 90 |
| Example 7-8 | 83 | 92 |
| Comparative Example 7-1 | 70 | 88 |
| Comparative Example 7-2 | 75 | 84 |
| Comparative Example 7-3 | 79 | 90 |

Example 8—High Temperature High Pressure Stewing+Ultrasonic Extraction of PHA

The polymerization degree of the polyhydroxyalkanoate, was exactly the average polymerization degree, it referred to the number of hydroxyalkanoic acid monomers in polymer molecules, and was characterized by the weight average molecular weight of the hydroxyalkanoic acid monomers;

The ultrasonic circulation extractor GCXZ-2B was purchased from Beijing Hongxianglong Biotechnology Corporation Limited;

Example 8-1

(1) The polyhydroxyalkanoate fermentation broth (fermented for 55 h) prepared in the Preparation Example was subjected to centrifugal separation through a disk-type centrifuge, such that the fermentation broth was separated into a bottom flow which was rich in thallus cells (with a water content of 80%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 80 wt %) (the second thallus cells) entered an extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.35 MPa, the pore size of filter cloth was 800 meshes, so as to obtain the third thallus cells and a third fermentation raffinate, the third thallus cells were fed into an extraction tank and mixed with the thallus (the second thallus cells) in the step (2), the third fermentation raffinate was fed into an adsorption separation tank for performing the adsorption treatment.

(4) The thallus cells in the extraction tank was washed for 2 times, and subjected to centrifugal separation to remove impurities therein.

(5) A stirring device of the extraction tank was started and operated at the rotation speed of 300 rpm, and the extraction tank was added with water having an equal volume of the bacterial cells to be crushed to obtain a bacterial suspension (the $OD_{600}$ value of the bacterial suspension was 100); then a heating, pressuring and crushing process was performed, the ultrasonic power relative to the bacterial suspension was controlled to be 500 $W/m^3$ for carrying out ultrasonic treatment for 15 min starting from the time of crushing thallus cells, the ultrasonic power relative to the bacterial suspension was subsequently increased by 150 $W/m^3$ for performing ultrasonic treatment until the time of crushing thallus cells was finished, a slurry containing polyhydroxyalkanoate was obtained; wherein the conditions of heating, pressurizing and crushing were as follows: the temperature of the bacterial suspension was 120° C., the pressure was 0.2 MPa, and the stewing time was 30 min.

(6) The obtained slurry was pumped into a disk-type centrifugal separator for performing solid-liquid separation at the rotation speed of 7,000 rpm, the separation condition caused that the slurry was separated into a top flow (liquid flow) containing impurities such as ammonia and thallus fragments, and a precipitate containing the polyhydroxyalkanoate, the obtained precipitate was subsequently returned to an extraction tank and subjected to washing with water for 2 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 20° C., the pressure was 0.35 MPa, and the time was 2.5 h, wherein the pore size of the filter cloth was 19 μm, and the filter cloth was coated with a polyhydroxyalkanoate layer (having a thickness of 7 mm); the obtained filtrate was used as an ingredient of the fermentation medium.

(8) The obtained polyhydroxyalkanoate was subjected to spray drying in order to prepare the polyhydroxyalkanoate dry powder.

The weight average molecular weight, yield and purity of the obtained polyhydroxyalkanoate were measured, and the measurement results were shown in Table 8.

Example 8-2

(1) The polyhydroxyalkanoate fermentation broth (fermented for 55 h) prepared in the Preparation Example was subjected to centrifugal separation through a disk-type centrifuge, such that the fermentation broth was separated into a bottom flow which was rich in thallus cells (with a water content of 90%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 75 wt %) (the second thallus cells) entered an extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.2 MPa, the pore size of filter cloth was 500 meshes, so as to obtain the third thallus cells and a third fermentation raffinate, the third thallus cells were fed into an extraction tank and mixed with the thallus (the second thallus cells) in the step (2), the third fermentation raffinate was fed into an adsorption separation tank for performing the adsorption treatment.

(4) The thallus cells in the extraction tank was washed for 2 times, and subjected to centrifugal separation to remove impurities therein.

(5) A stirring device of the extraction tank was started and operated at the rotation speed of 300 rpm, and the extraction tank was added with water having 0.8 volume of the bacterial cells to be crushed to obtain a bacterial suspension (the $OD_{600}$ value of the bacterial suspension was 150); then a heating, pressuring and crushing process was performed, the ultrasonic power relative to the bacterial suspension was controlled to be 300 $W/m^3$ for carrying out ultrasonic treatment for 20 min starting from the time of crushing thallus cells, the ultrasonic power relative to the bacterial suspension was subsequently increased by 100 $W/m^3$ for performing ultrasonic treatment until the time of crushing thallus cells was finished, a slurry containing polyhydroxyalkanoate was obtained; wherein the conditions of stewing and crushing were as follows: the temperature of the bacterial suspension was 110° C., the pressure was 0.15 MPa, and the stewing time was 40 min.

(6) The obtained slurry was pumped into a disk-type centrifugal separator for performing solid-liquid separation at the rotation speed of 3,000 rpm, the separation condition caused that the slurry was separated into a top flow (liquid flow) containing impurities such as ammonia and thallus fragments, and a precipitate containing the polyhydroxyalkanoate, the obtained precipitate was subsequently returned to an extraction tank and subjected to washing with water for 2 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 25° C., the pressure was 0.5 MPa, and the time was 3 h, wherein the pore size of the filter cloth was 23 μm, and the filter cloth was coated with a polyhydroxyalkanoate layer (having a thickness of 5 mm); the obtained filtrate was used as an ingredient of the fermentation medium.

(8) The obtained polyhydroxyalkanoate was subjected to spray drying in order to prepare the polyhydroxyalkanoate dry powder.

The weight average molecular weight, yield and purity of the obtained polyhydroxyalkanoate were measured, and the measurement results were shown in Table 8.

Example 8-3

(1) The polyhydroxyalkanoate fermentation broth (fermented for 55 h) prepared in the Preparation Example was subjected to centrifugal separation through a disk-type centrifuge, such that the fermentation broth was separated into a bottom flow which was rich in thallus cells (with a water content of 70%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 85 wt %) (the second thallus cells) entered an extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.5 MPa, the pore size of filter cloth was 1,000 meshes, so as to obtain the third thallus cells and a third fermentation raffinate, the third thallus cells were fed into an extraction tank and mixed with the thallus (the second thallus cells) in the step (2), the third fermentation raffinate was fed into an adsorption separation tank for performing the adsorption treatment.

(4) The thallus cells in the extraction tank was washed for 2 times, and subjected to centrifugal separation to remove impurities therein.

(5) A stirring device of the extraction tank was started and operated at the rotation speed of 400 rpm, and the extraction tank was added with water having an equal volume of the bacterial cells to be crushed to obtain a bacterial suspension (the $OD_{600}$ value of the bacterial suspension was 120); then a heating, pressuring and crushing process was performed, the ultrasonic power relative to the bacterial suspension was controlled to be 800 W/m$^3$ for carrying out ultrasonic treatment for 10 min starting from the time of crushing thallus cells, the ultrasonic power relative to the bacterial suspension was subsequently increased by 200 W/m$^3$ for performing ultrasonic treatment until the time of crushing thallus cells was finished, a slurry containing polyhydroxyalkanoate was obtained; wherein the conditions of stewing and crushing were as follows: the temperature of the bacterial suspension was 125° C., the pressure was 0.25 MPa, and the stewing time was 20 min.

(6) The obtained slurry was pumped into a disk-type centrifugal separator for performing solid-liquid separation at the rotation speed of 10,000 rpm, the separation condition caused that the slurry was separated into a top flow (liquid flow) containing impurities such as ammonia and thallus fragments, and a precipitate containing the polyhydroxyalkanoate, the obtained precipitate was subsequently returned to an extraction tank and subjected to washing with water for 2 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 15° C., the pressure was 0.2 MPa, and the time was 2 h, wherein the pore size of the filter cloth was 13 μm, and the filter cloth was coated with a polyhydroxyalkanoate layer (having a thickness of 10 mm); the obtained filtrate was used as an ingredient of the fermentation medium.

(8) The obtained polyhydroxyalkanoate was subjected to spray drying in order to prepare the polyhydroxyalkanoate dry powder.

The weight average molecular weight, yield and purity of the obtained polyhydroxyalkanoate were measured, and the measurement results were shown in Table 8.

Example 8-4

The polyhydroxyalkanoate fermentation broth was treated according to the method in the Example 8-1, except that the filtration in step (1) was performed by using a plate and frame filter, the centrifugal separation in step (2) was performed with a disk-type centrifuge, and the filtration in step (3) was performed by using a ribbon-type vacuum filter.

The weight average molecular weight, yield and purity of the obtained polyhydroxyalkanoate were measured, and the measurement results were shown in Table 8.

Example 8-5

The polyhydroxyalkanoate was extracted according to the method of the Example 8-1, except that in step (5), the extraction tank was added with water having 5 volumes of the bacterial cells to be crushed; the conditions of stewing and crushing were as follows: the temperature of the bacterial suspension was 135° C., the pressure was 0.35 MPa, and the stewing time was 60 min.

The weight average molecular weight, yield and purity of the obtained polyhydroxyalkanoate were measured, and the measurement results were shown in Table 8.

Example 8-6

The polyhydroxyalkanoate was extracted according to the method of the Example 8-1, except that in step (7), the filter membrane of the plate and frame filter was precoated with the polyhydroxyalkanoate layer having a thickness of 20 mm.

The weight average molecular weight, yield and purity of the obtained polyhydroxyalkanoate were measured, and the measurement results were shown in Table 8.

Example 8-7

The polyhydroxyalkanoate was extracted according to the method of the Example 8-1, except that in step (5), the ultrasonic power relative to the bacterial suspension was 500 W/m³ from the start time of crushing the thallus cells to the time of completing the crushing process.

The weight average molecular weight, yield and purity of the obtained polyhydroxyalkanoate were measured, and the measurement results were shown in Table 8.

Comparative Example 8-1

The PHA extraction from the thallus cells in the extraction tank in step (3) of the Example 8-2 was performed according to the method disclosed in Example 1 of CN 106687502A.

The weight average molecular weight, yield and purity of the obtained polyhydroxyalkanoate were measured, and the measurement results were shown in Table 8.

Comparative Example 8-2

The polyhydroxyalkanoate was extracted according to the method of the Example 8-1, except that the filter membrane of the plate and frame filter in step (7) was not precoated with a polyhydroxyalkanoate layer.

The weight average molecular weight, yield and purity of the obtained polyhydroxyalkanoate were measured, and the measurement results were shown in Table 8.

Comparative Example 8-3

The polyhydroxyalkanoate was extracted according to the method of the Comparative Example 8-2, except that the conditions for the stewing and crushing in step (5) were as follows: the temperature of the bacterial suspension was 100° C., the pressure was normal pressure, and the stewing time was 30 min.

The weight average molecular weight, yield and purity of the obtained polyhydroxyalkanoate were measured, and the measurement results were shown in Table 8.

TABLE 8

| Numbers | Yield (%) | Purity (%) | Weight average molecular weight of PHA |
| --- | --- | --- | --- |
| Example 8-1 | 89 | 96 | 360 KDa |
| Example 8-2 | 89 | 96 | 350 KDa |
| Example 8-3 | 88 | 95 | 350 KDa |
| Example 8-4 | 86 | 94 | 330 KDa |
| Example 8-5 | 85 | 95 | 340 KDa |
| Example 8-6 | 84 | 94 | 310 KDa |
| Example 8-7 | 82 | 93 | 300 KDa |
| Comparative Example 8-1 | 77 | 85 | 260 KDa |
| Comparative Example 8-2 | 75 | 90 | 320 KDa |
| Comparative Example 8-3 | 68 | 85 | 240 KDa |

As can be seen from the results in Table 8, the polyhydroxyalkanoate extracted by using the technical solution of the present disclosure had high yield and purity, and high polymerization degree, and the high PHA yield and purity indirectly lowered the production cost.

Example 9—Ammonia+Ultrasound Extraction of PHA

The polymerization degree of the polyhydroxyalkanoate, was exactly the average polymerization degree, it referred to the number of hydroxyalkanoic acid monomers in polymer molecules, and was characterized by the weight average molecular weight of the hydroxyalkanoic acid monomers;

The ammonia liquor with a concentration of 25 wt % was purchased from Shandong Hengchang Shengcheng Chemical Co., Ltd.;

The ultrasonic circulation extractor GCXZ-2B was purchased from Beijing Hongxianglong Biotechnology Corporation Limited;

Example 9-1

(1) The polyhydroxyalkanoate fermentation broth (fermented for 55 h) prepared in the Preparation Example 9-1 was subjected to centrifugal separation through a disk-type centrifuge, such that the fermentation broth was separated into a bottom flow which was rich in thallus cells (with a water content of 90%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 75 wt %) (the second thallus cells) entered an ultrasonic-assisted extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.2 MPa, the pore size of filter cloth was 500 meshes, so as to obtain the third thallus cells and a third fermentation raffinate, the third thallus cells were fed into an ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank was washed for 2 times, and subjected to centrifugal separation to remove impurities therein.

(5) A stirring device of the ultrasonic extraction tank was started and operated at the rotation speed of 200 rpm, and the extraction tank was added with ammonia liquor and water, such that the concentration of ammonia in terms of $NH_4OH$ in the finally obtained bacterial suspension was 0.2 mol/L, and the $OD_{600}$ value of the bacterial suspension was 200, the ultrasonic crushing was subsequently performed to obtain a slurry containing polyhydroxyalkanoate, wherein the ultrasonic power relative to the bacterial suspension was 300 W/m³, the temperature of the bacterial suspension was 70° C., the time of ultrasonic crushing was 60 min, and the pressure was the normal pressure.

(6) The obtained slurry was pumped into a disk-type centrifugal separator for performing solid-liquid separation, the centrifugal separation condition caused that the slurry was separated into a top flow (liquid flow) containing impurities such as ammonia and thallus fragments, and a precipitate containing the polyhydroxyalkanoate, the obtained precipitate was subsequently returned to an extraction tank and subjected to washing with water for 2 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 25° C., the pressure was 0.5 MPa, and the time was 3 h, wherein the pore size of the filter cloth was 13 μm, and the filter cloth was coated with a polyhydroxyalkanoate layer (having a thickness of 10 mm); the obtained filtrate was used as an ingredient of the fermentation medium.

(8) The obtained polyhydroxyalkanoate was subjected to spray drying in order to prepare the polyhydroxyalkanoate dry powder.

The polymerization degree, yield and purity of the obtained polyhydroxyalkanoate were measured, and the measurement results were shown in Table 9.

Example 9-2

(1) The polyhydroxyalkanoate fermentation broth (fermented for 55 h) prepared in the Preparation Example 9-1 was subjected to centrifugal separation through a disk-type centrifuge, such that the fermentation broth was separated into a bottom flow which was rich in thallus cells (with a water content of 80%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 80 wt %) (the second thallus cells) entered an ultrasonic-assisted extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.4 MPa, the pore size of filter cloth was 400 meshes, so as to obtain the third thallus cells and a third fermentation raffinate, the third thallus cells were fed into an ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank was washed for 2 times, and subjected to centrifugal separation to remove impurities therein.

(5) A stirring device of the ultrasonic extraction tank was started and operated at the rotation speed of 250 rpm, and the extraction tank was added with ammonia liquor and water, such that the concentration of ammonia in terms of $NH_4OH$ in the finally obtained bacterial suspension was 0.35 mol/L, and the $OD_{600}$ value of the bacterial suspension was 400, the ultrasonic crushing was subsequently performed to obtain a slurry containing polyhydroxyalkanoate, wherein the ultrasonic power relative to the bacterial suspension was 500 $W/m^3$, the temperature of the bacterial suspension was 75° C., the time of ultrasonic crushing was 75 min, and the pressure was the normal pressure.

(6) The obtained slurry was pumped into a disk-type centrifugal separator for performing solid-liquid separation, the centrifugal separation condition caused that the slurry was separated into a top flow (liquid flow) containing impurities such as ammonia and thallus fragments, and a precipitate containing the polyhydroxyalkanoate, the obtained precipitate was subsequently returned to an extraction tank and subjected to washing with water for 2 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 25° C., the pressure was 0.35 MPa, and the time was 2.5 h, wherein the pore size of the filter cloth was 19 μm, and the filter cloth was coated with a polyhydroxyalkanoate layer (having a thickness of 7 mm); the obtained filtrate was used as an ingredient of the fermentation medium.

(8) The obtained polyhydroxyalkanoate was subjected to spray drying in order to prepare the polyhydroxyalkanoate dry powder.

The polymerization degree, yield and purity of the obtained polyhydroxyalkanoate were measured, and the measurement results were shown in Table 9.

Example 9-3

(1) The polyhydroxyalkanoate fermentation broth (fermented for 55 h) prepared in the Preparation Example 9-1 was subjected to centrifugal separation through a disk-type centrifuge, such that the fermentation broth was separated into a bottom flow which was rich in thallus cells (with a water content of 70%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 85 wt %) (the second thallus cells) entered an ultrasonic-assisted extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.5 MPa, the pore size of filter cloth was 1,000 meshes, so as to obtain the third thallus cells and a third fermentation raffinate, the third thallus cells were fed into an ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank was washed for 2 times, and subjected to centrifugal separation to remove impurities therein.

(5) A stirring device of the ultrasonic extraction tank was started and operated at the rotation speed of 300 rpm, and the extraction tank was added with ammonia liquor and water, such that the concentration of ammonia in terms of $NH_4OH$ in the finally obtained bacterial suspension was 0.5 mol/L, and the $OD_{600}$ value of the bacterial suspension was 600, the ultrasonic crushing was subsequently performed to obtain a slurry containing polyhydroxyalkanoate, wherein the ultrasonic power relative to the bacterial suspension was 1,000 $W/m^3$, the temperature of the bacterial suspension was 80° C., the time of ultrasonic crushing was 90 min, and the pressure was the normal pressure.

(6) The obtained slurry was pumped into a disk-type centrifugal separator for performing solid-liquid separation, the centrifugal separation condition caused that the slurry was separated into a top flow (liquid flow) containing impurities such as ammonia and thallus fragments, and a precipitate containing the polyhydroxyalkanoate, the obtained precipitate was subsequently returned to an extraction tank and subjected to washing with water for 2 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 15° C., the pressure was 0.2 MPa, and the time was 2 h, wherein the pore size of the filter cloth was 23 μm, and the filter cloth was coated with a polyhydroxyalkanoate layer (having a thickness of 5 mm); the obtained filtrate was used as an ingredient of the fermentation medium.

(8) The obtained polyhydroxyalkanoate was subjected to spray drying in order to prepare the polyhydroxyalkanoate dry powder.

The polymerization degree, yield and purity of the obtained polyhydroxyalkanoate were measured, and the measurement results were shown in Table 9.

Example 9-4

The polyhydroxyalkanoate was extracted according to the method in the Example 9-2, except that the concentration of ammonia in terms of $NH_4OH$ in the finally obtained bacterial suspension in step (5) was 1 mol/L.

The polymerization degree, yield and purity of the obtained polyhydroxyalkanoate were measured, and the measurement results were shown in Table 9.

Example 9-5

The polyhydroxyalkanoate was extracted according to the method in the Example 9-2, except that the filter cloth was coated with a polyhydroxyalkanoate layer having an average thickness of 20 mm.

The polymerization degree, yield and purity of the obtained polyhydroxyalkanoate were measured, and the measurement results were shown in Table 9.

Example 9-6

The polyhydroxyalkanoate was extracted according to the method in the Example 9-2, except that the filtration in step (1) was performed y using a plate and frame filter, the centrifugal separation in step (2) was performed with a disk-type centrifuge, and the filtration in step (3) was performed by using a ribbon-type vacuum filter.

The polymerization degree, yield and purity of the obtained polyhydroxyalkanoate were measured, and the measurement results were shown in Table 9.

Example 9-7

The polyhydroxyalkanoate was extracted according to the method in the Example 9-1, except that, in the step (5), the ultrasonic power relative to the mixed solution was 2,000 $W/m^3$, the temperature was 60° C., the time was 180 min, and the pressure was normal pressure.

The polymerization degree, yield and purity of the obtained polyhydroxyalkanoate were measured, and the measurement results were shown in Table 9.

Example 9-8

The polyhydroxyalkanoate was extracted according to the method in the Example 9-1, except that the filter cloth of the frame filter in step (7) was not precoated with a polyhydroxyalkanoate layer.

The polymerization degree, yield and purity of the obtained polyhydroxyalkanoate were measured, and the measurement results were shown in Table 9.

Example 9-9

The polyhydroxyalkanoate was extracted according to the method in the Example 9-1, except that the pore size of the filter cloth of the plate and frame filter in step (7) was 25 μm.

The polymerization degree, yield and purity of the obtained polyhydroxyalkanoate were measured, and the measurement results were shown in Table 9.

Comparative Example 9-1

The PHA extraction from the thallus cells in the extraction tank in step (3) of the Example 9-1 was performed according to the method disclosed in Example 1 of CN 106687502A.

The polymerization degree, yield and purity of the obtained polyhydroxyalkanoate were measured, and the measurement results were shown in Table 9.

Comparative Example 9-2

The polyhydroxyalkanoate was extracted according to the method in the Example 9-1, except that the ammonia liquor added in step (5) was replaced with an equal volume of water.

The polymerization degree, yield and purity of the obtained polyhydroxyalkanoate were measured, and the measurement results were shown in Table 9.

Comparative Example 9-3

The polyhydroxyalkanoate was extracted according to the method in the Example 9-1, except that the ultrasonic device was not switched on in step (5).

The polymerization degree, yield and purity of the obtained polyhydroxyalkanoate were measured, and the measurement results were shown in Table 9.

Comparative Example 9-4

The polyhydroxyalkanoate was extracted according to the method in the Example 9-1, except that the ammonia liquor was replaced with sodium hydroxide, and the pH of the bacterial suspension was adjusted to be same as in Example 9-1.

The polymerization degree, yield and purity of the obtained polyhydroxyalkanoate were measured, and the measurement results were shown in Table 9.

TABLE 9

| Numbers | Yield (%) | Purity (%) | Weight average molecular weight of PHA |
| --- | --- | --- | --- |
| Example 9-1 | 89 | 96 | 350 KDa |
| Example 9-2 | 89 | 96 | 360 KDa |
| Example 9-3 | 88 | 95 | 340 KDa |
| Example 9-4 | 87 | 94 | 300 KDa |

TABLE 9-continued

| Numbers | Yield (%) | Purity (%) | Weight average molecular weight of PHA |
|---|---|---|---|
| Example 9-5 | 85 | 92 | 310 KDa |
| Example 9-6 | 83 | 93 | 320 KDa |
| Example 9-7 | 85 | 92 | 320 KDa |
| Example 9-8 | 80 | 90 | 310 KDa |
| Example 9-9 | 83 | 93 | 320 KDa |
| Comparative Example 9-1 | 77 | 85 | 260 KDa |
| Comparative Example 9-2 | 77 | 90 | 270 KDa |
| Comparative Example 9-3 | 76 | 90 | 280 KDa |
| Comparative Example 9-4 | 75 | 90 | 230 KDa |

As can be seen from the results in Table 9, the polyhydroxyalkanoate extracted by using the technical solution of the present disclosure had high yield and purity and high polymerization degree (it was characterized by the weight average molecular weight of PHA), and the high PHA yield and purity indirectly lowered the production cost.

Example 10—Extraction of PHA with SDS+Lysozyme

The weight average molecular weight of the polyhydroxyalkanoate was measured by the gel permeation chromatography;

The surfactant sodium dodecyl sulfate (SDS) was purchased from the Yeyuan Biotechnology Co., Ltd., the product number was S15013;

The polyhydroxyalkanoate with a particle size of 1-200 m was purchased from Langene Biotechnology Co., Ltd.;

The ultrasonic circulation extractor GCXZ-2B was purchased from Beijing Hongxianglong Biotechnology Corporation Limited;

lysozyme CAS: 12650-88-3, which was which was purchased from Beijing Oriental Rada Biotech Co., Ltd.;

Example 10-1

(1) The polyhydroxyalkanoate fermentation broth (fermented for 55 h) prepared in the Preparation Example 10-1 was subjected to centrifugal separation through a disk-type centrifuge, such that the fermentation broth was separated into a bottom flow which was rich in thallus cells (with a water content of 80%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 80 wt %) (the second thallus cells) entered a first ultrasonic extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.4 MPa, the pore size of filter cloth was 10 μm, so as to obtain the third thallus cells and a third fermentation raffinate, the third thallus cells were fed into the first ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank were washed with water for 3 times, and subjected to centrifugal separation to obtain the bacterial cells to be crushed and remove impurities therein.

(5) A stirring device of the ultrasonic extraction tank was started and operated at the rotation speed of 250 rpm, the ultrasonic extraction tank was added with water having an equal volume of the thallus cells to be crushed so as to re-suspend the thallus and obtain the bacterial suspension, the lysozyme was subsequently added to obtain a mixed material, such that the content of lysozyme in the mixed material was 0.3 g/L; the ultrasonic crushing was subsequently performed to obtain a slurry containing polyhydroxyalkanoate, the ultrasonic power relative to the mixed material was controlled to be 600 W/m$^3$ for carrying out ultrasonic treatment for 75 min starting from the time of crushing thallus cells, the ultrasonic power relative to the mixed material was subsequently increased by 150 W/m$^3$ for performing ultrasonic treatment until the time of crushing thallus cells was finished; the temperature of the mixed material was 35° C., the time of ultrasonic crushing was 120 min, the pressure was the normal pressure.

(6) The obtained slurry was pumped into a disk-type centrifugal separator for performing solid-liquid separation at the rotation speed of 7,000 rpm, the separation condition caused that the slurry was separated into a top flow (liquid flow) containing impurities such as ammonia and thallus fragments, and a precipitate containing the polyhydroxyalkanoate, the obtained top flow containing impurities such as ammonia and thallus fragments was used as an ingredient of the next batch of the fermentation medium.

(7) The obtained precipitate was fed into a second ultrasonic extraction tank, a stirring device was stared at the rotating speed of 250 rpm, the second ultrasonic extraction tank was added with water having the same weight as the PHA precipitate to re-suspend the precipitate so as to obtain a PHA-containing turbid liquid, the SDS was subsequently added to obtain a mixed material, wherein the mass ratio of the SDS to the PHA in the obtained mixed material was 0.09:1000; the ultrasonic crushing was then performed to obtain a second slurry containing the polyhydroxyalkanoate, wherein the ultrasonic power relative to the mixed material was 600 W/m$^3$, the temperature of the mixed material was 75° C., the time of ultrasonic crushing was 80 min, and the pressure was the normal pressure.

(8) The obtained slurry was pumped into a disk-type centrifugal separator for performing solid-liquid separation at the rotation speed of 7,000 rpm, the separation condition caused that the slurry was separated into a top flow (liquid flow) containing impurities such as ammonia and thallus fragments, and a precipitate containing the polyhydroxyalkanoate, the obtained precipitate was subsequently returned to an extraction tank for washing with water for 3 times.

(9) The precipitate washed with water in the step (8) was fed into a plate and frame filter for performing solid-liquid separation, so as to obtain polyhydroxyalkanoate and filtrate, the filtering conditions were as follows: the temperature was 20° C., the pressure was 0.35 MPa, and the time was 2.5 h, wherein the pore size of the filter cloth was 19 μm, and the filter cloth was coated with a polyhydroxyalkanoate layer (having a thickness of 8 mm); the obtained filtrate was used as an ingredient of the fermentation medium.

(10) The obtained polyhydroxyalkanoate was subjected to spray drying in order to prepare the polyhydroxyalkanoate dry powder.

The yield, purity and average molecular weight of the obtained polyhydroxyalkanoate were measured, and the measurement results were shown in Table 10.

Example 10-2

(1) The polyhydroxyalkanoate fermentation broth (fermented for 55 h) prepared in the Preparation Example 10-1 was subjected to centrifugal separation through a disk-type centrifuge, such that the fermentation broth was separated into a bottom flow which was rich in thallus cells (with a water content of 90%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 75 wt %) (the second thallus cells) entered a first ultrasonic extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.5 MPa, the pore size of filter cloth was 7 μm, so as to obtain the third thallus cells and a third fermentation raffinate, the third thallus cells were fed into the first ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank were washed with water for 2 times, and subjected to centrifugal separation to obtain the bacterial cells to be crushed and remove impurities therein.

(5) A stirring device of the ultrasonic extraction tank was started and operated at the rotation speed of 300 rpm, the ultrasonic extraction tank was added with water having 0.8 volume of the thallus cells to be crushed so as to re-suspend the thallus and obtain the bacterial suspension, the lysozyme was subsequently added to obtain a mixed material, such that the content of lysozyme in the mixed material was 0.5 g/L; the ultrasonic crushing was subsequently performed to obtain a slurry containing polyhydroxyalkanoate, the ultrasonic power relative to the mixed material was controlled to be 800 W/m$^3$ for carrying out ultrasonic treatment for 60 min starting from the time of crushing thallus cells, the ultrasonic power relative to the mixed material was subsequently increased by 100 W/m$^3$ for performing ultrasonic treatment until the time of crushing thallus cells was finished; the temperature of the mixed material was 40° C., the time of ultrasonic crushing was 150 min, the pressure was the normal pressure.

(6) The obtained slurry was pumped into a disk-type centrifugal separator for performing solid-liquid separation at the rotation speed of 7,000 rpm, the separation condition caused that the slurry was separated into a top flow (liquid flow) containing impurities such as ammonia and thallus fragments, and a precipitate containing the polyhydroxyalkanoate, the obtained top flow containing impurities such as ammonia and thallus fragments was used as an ingredient of the next batch of the fermentation medium.

(7) The obtained precipitate was fed into a second ultrasonic extraction tank, a stirring device was stared at the rotating speed of 300 rpm, the ultrasonic extraction tank was added with water having the same weight as the PHA precipitate to re-suspend the precipitate so as to obtain a PHA-containing turbid liquid, the sodium dodecyl sulfate (SDS) was subsequently added to obtain a mixed material, wherein the mass ratio of the SDS to the PHA in the obtained mixed material was 0.1:1000; the ultrasonic crushing was then performed to obtain a second slurry containing the polyhydroxyalkanoate, wherein the ultrasonic power relative to the mixed material was 1,000 W/m$^3$, the temperature of the mixed material was 80° C., the time of ultrasonic crushing was 90 min, and the pressure was the normal pressure.

(8) The obtained slurry was pumped into a disk-type centrifugal separator for performing solid-liquid separation at the rotation speed of 7,000 rpm, the separation condition caused that the slurry was separated into a top flow (liquid flow) containing impurities such as ammonia and thallus fragments, and a precipitate containing the polyhydroxyalkanoate, the obtained precipitate was subsequently returned to an extraction tank for washing with water for 5 times.

(9) The precipitate washed with water in the step (8) was fed into a plate and frame filter for performing solid-liquid separation, so as to obtain polyhydroxyalkanoate and filtrate, the filtering conditions were as follows: the temperature was 40° C., the pressure was 0.5 MPa, and the time was 3 h, wherein the pore size of the filter cloth was 13 μm, and the filter cloth was coated with a polyhydroxyalkanoate layer (having a thickness of 10 mm); the obtained filtrate was used as an ingredient of the fermentation medium.

(10) The obtained polyhydroxyalkanoate was subjected to spray drying in order to prepare the polyhydroxyalkanoate dry powder.

The yield, purity and average molecular weight of the obtained polyhydroxyalkanoate were measured, and the measurement results were shown in Table 10.

Example 10-3

(1) The polyhydroxyalkanoate fermentation broth (fermented for 55 h) prepared in the Preparation Example 10-1 was subjected to centrifugal separation through a disk-type centrifuge, such that the fermentation broth was separated into a bottom flow which was rich in thallus cells (with a water content of 70%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 85 wt %) (the second thallus cells) entered a first ultrasonic extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.2 MPa, the pore size of filter cloth was 25 μm, so as to obtain the third thallus cells and a third fermentation raffinate, the third thallus cells were fed into the first ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank were washed with water for 2 times, and subjected to centrifugal separation to obtain the bacterial cells to be crushed and remove impurities therein.

(5) A stirring device of the ultrasonic extraction tank was started and operated at the rotation speed of 200 rpm, the ultrasonic extraction tank was added with water having 2 volumes of the thallus cells to be crushed so as to re-suspend the thallus and obtain the bacterial suspension, the lysozyme was subsequently added to obtain a mixed material, such that the content of lysozyme in the mixed material was 0.1 g/L; the ultrasonic crushing was subsequently performed to obtain a slurry containing polyhydroxyalkanoate, the ultrasonic power relative to the mixed material was controlled to be 300 W/m$^3$ for carrying out ultrasonic treatment for 60 min starting from the time of crushing thallus cells, the ultrasonic power relative to the mixed material was subsequently increased by 100 W/m$^3$ for performing ultrasonic treatment until the time of crushing thallus cells was finished; the temperature of the mixed material was 30° C., the time of ultrasonic crushing was 90 min, the pressure was the normal pressure.

(6) The obtained slurry was pumped into a disk-type centrifugal separator for performing solid-liquid separation at the rotation speed of 3,000 rpm, the separation condition caused that the slurry was separated into a top flow (liquid flow) containing impurities such as ammonia and thallus fragments, and a precipitate containing the polyhydroxyalkanoate, the obtained top flow containing impurities such as ammonia and thallus fragments was used as an ingredient of the next batch of the fermentation medium.

(7) The obtained precipitate was fed into a second ultrasonic extraction tank, a stirring device was stared at the rotating speed of 100 rpm, the ultrasonic extraction tank was added with water having the same weight as the PHA precipitate to re-suspend the precipitate so as to obtain a PHA-containing turbid liquid, the sodium dodecyl sulfate (SDS) was subsequently added to obtain a mixed material, wherein the mass ratio of the SDS to the PHA in the obtained mixed material was 0.08:1000; the ultrasonic crushing was then performed to obtain a second slurry containing the polyhydroxyalkanoate, wherein the ultrasonic power relative to the mixed material was 300 W/m$^3$, the temperature of the mixed material was 70° C., the time of ultrasonic crushing was 90 min, and the pressure was the normal pressure.

(8) The obtained slurry was pumped into a disk-type centrifugal separator for performing solid-liquid separation at the rotation speed of 3,000 rpm, the separation condition caused that the slurry was separated into a top flow (liquid flow) containing impurities such as ammonia and thallus fragments, and a precipitate containing the polyhydroxyalkanoate, the obtained precipitate was subsequently returned to an extraction tank for washing with water for 3 times.

(9) The precipitate washed with water in the step (8) was fed into a plate and frame filter for performing solid-liquid separation, so as to obtain polyhydroxyalkanoate and filtrate, the filtering conditions were as follows: the temperature was 15° C., the pressure was 0.2 MPa, and the time was 2 h, wherein the pore size of the filter cloth was 23 μm, and the filter cloth was coated with a polyhydroxyalkanoate layer (having a thickness of 5 mm); the obtained filtrate was used as an ingredient of the fermentation medium.

(10) The obtained polyhydroxyalkanoate was subjected to spray drying in order to prepare the polyhydroxyalkanoate dry powder.

The yield, purity and average molecular weight of the obtained polyhydroxyalkanoate were measured, and the measurement results were shown in Table 10.

Example 10-4

The polyhydroxyalkanoate was extracted according to the method of the Example 10-1, except that in step (5), the content of lysozyme in the finally obtained mixed material was 1 g/L.

The yield, purity and average molecular weight of the obtained polyhydroxyalkanoate were measured, and the measurement results were shown in Table 10.

Example 10-5

The polyhydroxyalkanoate was extracted according to the method of the Example 10-1, except that in step (5), the ultrasonic power relative to the mixed solution was 2,000 W/m$^3$, the temperature was 20° C., the time was 240 min, and the pressure was normal pressure.

The yield, purity and average molecular weight of the obtained polyhydroxyalkanoate were measured, and the measurement results were shown in Table 10.

Example 10-6

The polyhydroxyalkanoate was extracted according to the method of the Example 10-1, except that in step (5), the mass ratio of SDS to PHA in the finally obtained mixed material was 0.3:1000.

The yield, purity and average molecular weight of the obtained polyhydroxyalkanoate were measured, and the measurement results were shown in Table 10.

Example 10-7

The polyhydroxyalkanoate was extracted according to the method of the Example 10-1, except that the filter cloth of the plate and frame filter in step (9) was not pre-coated with a polyhydroxyalkanoate layer.

The yield, purity and average molecular weight of the obtained polyhydroxyalkanoate were measured, and the measurement results were shown in Table 10.

Example 10-8

The polyhydroxyalkanoate was extracted according to the method of the Example 10-1, except that the thickness of the polyhydroxyalkanoate layer precoated with the filter cloth of the plate and frame filter in step (9) was 20 mm.

The yield, purity and average molecular weight of the obtained polyhydroxyalkanoate were measured, and the measurement results were shown in Table 10.

Comparative Example 10-1

(1) The polyhydroxyalkanoate fermentation broth prepared in the Preparation Example 10-1 was subjected to centrifugal separation through a disk-type centrifuge, such that the fermentation broth was separated into a bottom flow which was rich in thallus cells (with a water content of 80%) (the first thallus cells), and a fermentation raffinate top flow (the first fermentation raffinate) which was fed into a fermentation raffinate temporary storage tank.

(2) The bottom flow which was obtained in the step (1) and rich in the target thallus cells was washed with an equal volume of water for 2 times, the bottom flow was pumped into a ribbon-type vacuum filter for filtering and drying, the filtered and dried thalli (with the water content of 80 wt %) (the second thallus cells) entered a first ultrasonic extraction tank, the filtrate (the second fermentation raffinate) was fed into the fermentation raffinate temporary storage tank.

(3) The mixed liquid of the fermentation raffinate and the filtrate in the fermentation raffinate temporary storage tank was pumped into a plate and frame filter for performing filtration, wherein the filtering pressure was 0.4 MPa, the pore size of filter cloth was 10 μm, so as to obtain the third thallus cells and a third fermentation raffinate, the third thallus cells were fed into the first ultrasonic extraction tank and mixed with the thallus (the second thallus cells) in the step (2), the third fermentation raffinate was fed into an adsorption separation tank for performing the adsorption treatment.

(4) The thallus cells in the ultrasonic extraction tank were washed with water for 3 times, and subjected to centrifugal separation to obtain the bacterial cells to be crushed and remove impurities therein.

(5) A stirring device of the ultrasonic extraction tank was started and operated at the rotation speed of 250 rpm, the ultrasonic extraction tank was added with water having an equal volume of the thallus cells to be crushed so as to re-suspend the thallus and obtain the bacterial suspension, the lysozyme was subsequently added to obtain a mixed material, such that the content of lysozyme in the mixed material was 0.3 g/L; the ultrasonic crushing was subsequently performed to obtain a slurry containing polyhydroxyalkanoate, the ultrasonic power relative to the mixed material was controlled to be 600 W/m³ for carrying out ultrasonic treatment for 75 min starting from the time of crushing thallus cells, the ultrasonic power relative to the mixed material was subsequently increased by 150 W/m³ for performing ultrasonic treatment until the time of crushing thallus cells was finished; the temperature of the mixed material was 35° C., the time of ultrasonic crushing was 120 min, the pressure was the normal pressure.

(6) The obtained slurry was pumped into a disk-type centrifugal separator for performing solid-liquid separation at the rotation speed of 7,000 rpm, the separation condition caused that the slurry was separated into a top flow (liquid flow) containing impurities such as ammonia and thallus fragments, and a precipitate containing the polyhydroxyalkanoate; the obtained precipitate was then returned to the extraction and washed with water for 3 times, the obtained top flow containing impurities such as ammonia and thallus fragments was used as an ingredient of the next batch of the fermentation medium.

(7) The precipitate washed with water in the step (6) was fed into a plate and frame filter for performing solid-liquid separation, so as to obtain polyhydroxyalkanoate and filtrate, the filtering conditions were as follows: the temperature was 20° C., the pressure was 0.35 MPa, and the time was 2.5 h, wherein the pore size of the filter cloth was 19 μm, and the filter cloth was coated with a polyhydroxyalkanoate layer (having a thickness of 8 mm); the obtained filtrate was used as an ingredient of the fermentation medium.

(8) The obtained polyhydroxyalkanoate was subjected to spray drying in order to prepare the polyhydroxyalkanoate dry powder.

The yield, purity and average molecular weight of the obtained polyhydroxyalkanoate were measured, and the measurement results were shown in Table 10.

Comparative Example 10-2

The polyhydroxyalkanoate was extracted according to the method of the Example 10-1, except that the lysozyme was not added in step (5).

The yield, purity and average molecular weight of the obtained polyhydroxyalkanoate were measured, and the measurement results were shown in Table 10.

Comparative Example 10-3

The polyhydroxyalkanoate was extracted according to the method of the Example 10-1, except that the ultrasonic device in step (5) was not switched on.

The yield, purity and average molecular weight of the obtained polyhydroxyalkanoate were measured, and the measurement results were shown in Table 10.

TABLE 10

| Numbers | Yield (%) | Purity (%) | Weight average molecular weight of PHA |
| --- | --- | --- | --- |
| Example 10-1 | 89 | 97 | 370 kDa |
| Example 10-2 | 88 | 95 | 350 kDa |
| Example 10-3 | 86 | 94 | 360 kDa |
| Example 10-4 | 87 | 93 | 330 kDa |
| Example 10-5 | 85 | 90 | 310 kDa |
| Example 10-6 | 88 | 92 | 270 kDa |
| Example 10-7 | 81 | 90 | 350 kDa |
| Example 10-8 | 86 | 90 | 330 kDa |
| Comparative Example 10-1 | 84 | 88 | 350 kDa |
| Comparative Example 10-2 | 82 | 87 | 280 kDa |
| Comparative Example 10-3 | 83 | 88 | 310 kDa |

As can be seen from the results in Table 10, the polyhydroxyalkanoate extracted by using the technical solution of the present disclosure had high yield and purity and high molecular weight, and the high PHA yield and purity indirectly lowered the production cost.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

What is claimed is:

1. A method for producing PHA through fermentation comprising the following steps:
   (1) inoculating PHA fermentation strains into a fermentation medium for fermentation under the condition of being capable of producing PHA through fermentation to obtain a fermentation broth;
   (2) subjecting the fermentation broth to a first solid-liquid separation to obtain a fermentation supernatant and a thallus precipitate;

(3) breaking cell walls of the thallus precipitate, and subjecting obtained wall-broken products to a plate and frame filtration to obtain PHA;
wherein a filter cloth for the plate and frame filtration is pre-coated with a PHA layer;
wherein at least part of water of the fermentation medium is PHA process wastewater, and the PHA process wastewater comprises the fermentation supernatant.

2. The method of claim 1, wherein in step (1), the PHA process wastewater which is supplemented with pure water or not, is used as the water of the fermentation medium; the fermentation medium comprises a carbon source, a nitrogen source, a phosphate, a magnesium salt and a sodium salt;
wherein the carbon source is selected from the group consisting of glucose, starch saccharification liquid and high-salt molasses, wherein the high-salt molasses comprises 8-11 wt % of salt and 40-70 wt % of sugar based on the dry weight of the high-salt molasses; and/or
the nitrogen source is selected from the group consisting of corn steep liquor, corn steep liquor powder, soybean meal powder, yeast powder, urea and ammonium sulfate; and/or
the phosphate is dipotassium hydrogen phosphate and disodium hydrogen phosphate; and/or
the magnesium salt is magnesium sulfate and/or magnesium chloride; and/or
the sodium salt is sodium chloride.

3. The method of claim 2, wherein in the step (1), the nitrogen source is a natural composite nitrogen source obtained by enzymolysis treatment with cellulase, hemicellulase, amylase and acid protease.

4. The method according to claim 2, wherein in the step (1), the high-salt molasses is acid-hydrolyzed high-salt molasses.

5. The method of claim 1, wherein in step (1), the fermentation is performed under stirring condition, in a 2-7 L fermentation tank, rotation speed of the stirring is within a range of 400-600 rpm from 0 h to 8-12 h of the fermentation;
rotation speed of the stirring is within a range of 600-1,000 rpm from 8-12 h to 16-20 h of the fermentation;
rotation speed of the stirring is within a range of 400-600 rpm from 16-20 h to end of the fermentation; and/or
conditions of the fermentation comprising: temperature is 30-45° C., pH is 7-11, amount of dissolved oxygen is 1-40%, and ventilation quantity is 0.5-1.5 vvm.

6. The method of claim 1, wherein in step (1), the method further comprising that: in fermentation process, replenishing a first nutrient substance when sugar content in the fermentation medium drops below 12 g/L for the first time, wherein the first nutrient substance has a carbon-nitrogen ratio of 10-20:1; amount for a replenishment of the first nutrient substance is 8-12% by volume of the fermentation medium;
after the replenishment of the first nutrient substance has been finished, replenishing a second nutrient substance, wherein the second nutrient substance has a carbon-nitrogen ratio of 30-50:1; amount for a replenishment of the second nutrient substance is 5-10% by volume of the fermentation medium;
after the replenishment of the second nutrient substance has been finished, replenishing a third nutrient substance, wherein the third nutrient substance is glucose, and amount for a replenishment of the third nutrient substance is 20-30% by volume of the fermentation medium;
addition amount of the nutrient substances ensures that the sugar content in the fermentation medium is controlled within a range of 5-20 g/L.

7. The method of claim 1, wherein in step (3), a method for breaking the cell walls is a pressurizing and heating method in combination with a physical mechanical crushing method or not;
wherein in the pressurizing and heating method, temperature is 60-200° C., pressure is 0.1-0.3 MPa, and time is 10-240 min;
the physical mechanical crushing method is ultrasonic and/or homogenization.

8. The method of claim 1, wherein in step (3), the PHA pre-coated on the filter cloth has a particle size within the range of 1-200 μm; and/or
the PHA layer has a thickness of 1-30 mm; and/or
the filter cloth pre-coated with the PHA layer has a pore size of 1-25 μm.

9. The method of claim 1, wherein the method further comprising steps of subjecting the PHA process wastewater to impurities removing and recycling to fermentation process, wherein the PHA process wastewater after removing impurities has a COD value lower than 10,000 mg/L, a chroma lower than 80 and a viscosity lower than 20 CPS;
method for the impurities removing is selected from the group consisting of adsorption method, oxidation method, membrane separation method, chromatographic separation method and stewing method.

10. The method of claim 1, wherein the PHA fermentation strain is Halobacteriaceae or *Halomonas* sp.

* * * * *